US012723272B2

(12) United States Patent
Masakari et al.

(10) Patent No.: US 12,723,272 B2
(45) Date of Patent: Sep. 1, 2026

(54) MEDIATOR

(71) Applicant: KIKKOMAN CORPORATION, Chiba (JP)

(72) Inventors: Yosuke Masakari, Chiba (JP); Naoya Totsuka, Chiba (JP); Yasutomo Shinohara, Chiba (JP)

(73) Assignee: KIKKOMAN CORPORATION, Chiba (JP)

( * ) Notice: Subject to any disclaimer, the term of this patent is extended or adjusted under 35 U.S.C. 154(b) by 1106 days.

(21) Appl. No.: 17/046,610

(22) PCT Filed: Feb. 26, 2019

(86) PCT No.: PCT/JP2019/007373

§ 371 (c)(1),
(2) Date: Oct. 9, 2020

(87) PCT Pub. No.: WO2019/198359

PCT Pub. Date: Oct. 17, 2019

(65) Prior Publication Data

US 2021/0115489 A1 Apr. 22, 2021

(30) Foreign Application Priority Data

Apr. 13, 2018 (JP) ................................ 2018-077593
Apr. 13, 2018 (JP) ................................ 2018-077628

(51) Int. Cl.
*C12Q 1/00* (2006.01)
*C07C 211/55* (2006.01)
*H01M 4/90* (2006.01)
*H01M 8/16* (2006.01)

(52) U.S. Cl.
CPC ............ *C12Q 1/004* (2013.01); *C07C 211/55* (2013.01); *H01M 4/90* (2013.01); *H01M 8/16* (2013.01)

(58) Field of Classification Search
CPC .............................. C12Q 1/004; C07C 211/55
See application file for complete search history.

(56) References Cited

U.S. PATENT DOCUMENTS

| | | | |
|---|---|---|---|
| 5,609,749 A | 3/1997 | Yamauchi et al. | |
| 2003/0113606 A1 | 6/2003 | Ritts et al. | |
| 2006/0054501 A1 | 3/2006 | Jiang et al. | |
| 2008/0035481 A1 | 2/2008 | McCormack et al. | |
| 2010/0062469 A1* | 3/2010 | Umegae ................ | C12Q 1/005 435/25 |
| 2012/0090995 A1 | 4/2012 | Leonard et al. | |
| 2018/0366748 A1 | 12/2018 | Nariyama | |

FOREIGN PATENT DOCUMENTS

| | | | |
|---|---|---|---|
| JP | H7234201 A | 9/1995 | |
| JP | 2007526474 A | 9/2007 | |
| JP | 2008185534 A | 8/2008 | |
| JP | 2012522223 A | 9/2012 | |
| JP | 2016042032 A | 3/2016 | |
| JP | 2019003928 A | 1/2019 | |
| WO | 2004011929 A1 | 2/2004 | |
| WO | 2005085825 A1 | 9/2005 | |
| WO | WO-2007034131 A1 * | 3/2007 | ............ E21B 47/01 |

OTHER PUBLICATIONS

Molecular structure by Molbase (Year: 2024).*
4,4-Bis(dimethylamino)diphenylamine _ C16H21N3 _ CID 69473—PubChem (Year: 2025).*
Y. Masakari, Enzyme electrode for glucose oxidation using low-solubility 4-aminodiphenylamine derivatives as electron mediator, Electrochemical Science Advances, 2022(2), e2100036, pp. 1-6 (Year: 2021).*
Supplementary Partial European Search Report for Corresponding European Application No. 19784987.0, Jan. 11, 2022, 14 pages.
Malingappagari Pandurangappa, et al., "Physical adsorption of N, N'-diphenyl-p-phenylenediamine onto carbon particles: Application to the detection of sulfide", Analyst, vol. 128, No. 5, pp. 473-479, 2003.
Shinji Ando, et al., "Antioxidants", Nippon Gomu Kyokaishi, the Journal of the Society of Rubber Science and Technology, Japan, vol. 82, No. 2, pp. 45-49, 2009.
International Search Report issued in connection with corresponding PCT/JP2019/007373 mailed May 21, 2019 (2 pages) and English Translation.

* cited by examiner

*Primary Examiner* — C. Sun
(74) *Attorney, Agent, or Firm* — Lucas & Mercanti, LLP

(57) ABSTRACT

Provided is a novel mediator. The present invention relates to a novel mediator, and an electrode modifying agent and an electron transfer promoting agent comprising the mediator, an electrode, a battery, a composition, and an enzyme sensor comprising the electrode modifying agent or the electron transfer promoting agent, and a method using any of these.

15 Claims, 24 Drawing Sheets

Specification includes a Sequence Listing.

SEQUENCE LISTING

```
<160> NUMBER OF SEQ ID NOS: 4

<210> SEQ ID NO 1
<211> LENGTH: 641
<212> TYPE: PRT
<213> ORGANISM: Mucor prainii

<400> SEQUENCE: 1

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Ser Thr Asp Thr Tyr
            20                  25                  30

Asp Tyr Val Ile Val Gly Gly Gly Val Ala Gly Leu Ala Leu Ala Ser
        35                  40                  45

Arg Ile Ser Glu Asn Lys Asp Val Thr Val Ala Val Leu Glu Ser Gly
    50                  55                  60

Pro Asn Ala Asn Asp Arg Phe Val Val Tyr Ala Pro Gly Met Tyr Gly
65                  70                  75                  80
```

-continued

```
Gln Ala Val Gly Thr Asp Leu Cys Pro Leu Ile Pro Thr Thr Pro Gln
                85                  90                  95

Glu Asn Met Gly Asn Arg Ser Leu Thr Ile Ala Thr Gly Arg Leu Leu
            100                 105                 110

Gly Gly Gly Ser Ala Ile Asn Gly Leu Val Trp Thr Arg Gly Gly Leu
        115                 120                 125

Lys Asp Tyr Asp Ala Trp Glu Glu Leu Gly Asn Pro Gly Trp Asn Gly
    130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
                165                 170                 175

Gly Lys Lys Gly Pro Ile Asp Val Ser Phe Thr Asn Tyr Glu Phe Ser
            180                 185                 190

Gln Ser Ala Ser Trp Asn Ala Ser Leu Glu Thr Leu Asp Phe Thr Ala
        195                 200                 205

Leu Pro Asp Ile Leu Asn Gly Thr Leu Ala Gly Tyr Ser Thr Thr Pro
    210                 215                 220

Asn Ile Leu Asp Pro Glu Thr Val Gln Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
            260                 265                 270

Leu Lys Ala Thr Gly Val Glu Trp Tyr Pro Thr Gly Asn Lys Asn Gln
        275                 280                 285

Lys Gln Ile Ile Lys Ala Arg Tyr Glu Val Ile Ile Ser Ser Gly Ala
    290                 295                 300

Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
                325                 330                 335

Gly Ser Asn Met Gln Asp His Val His Ala Ile Thr Val Ser Thr Thr
            340                 345                 350

Asn Ile Thr Gly Tyr Thr Thr Asn Ser Val Phe Val Asn Glu Thr Leu
        355                 360                 365

Ala Gln Glu Gln Arg Glu Glu Tyr Glu Ala Asn Lys Thr Gly Ile Trp
    370                 375                 380

Ala Thr Thr Pro Asn Asn Leu Gly Tyr Pro Thr Pro Glu Gln Leu Phe
385                 390                 395                 400

Asn Gly Thr Glu Phe Val Ser Gly Lys Glu Phe Ala Asp Lys Ile Arg
                405                 410                 415

Asn Ser Thr Asp Glu Trp Ala Asn Tyr Tyr Ala Ser Thr Asn Ala Ser
            420                 425                 430

Asn Val Glu Leu Leu Lys Lys Gln Tyr Ala Ile Val Ala Ser Arg Tyr
        435                 440                 445

Glu Glu Asn Tyr Leu Ser Pro Ile Glu Ile Asn Phe Thr Pro Gly Tyr
    450                 455                 460

Glu Gly Ser Gly Asn Val Asp Leu Gln Asn Asn Lys Tyr Gln Thr Val
465                 470                 475                 480

Asn His Val Leu Ile Ala Pro Leu Ser Arg Gly Tyr Thr His Ile Asn
                485                 490                 495
```

-continued

```
Ser Ser Asp Val Glu Asp His Ser Val Ile Asn Pro Gln Tyr Tyr Ser
            500                 505                 510

His Pro Met Asp Ile Asp Val His Ile Ala Ser Thr Lys Leu Ala Arg
        515                 520                 525

Glu Ile Ile Thr Ala Ser Pro Gly Leu Gly Asp Ile Asn Ser Gly Glu
    530                 535                 540

Ile Glu Pro Gly Met Asn Ile Thr Ser Glu Asp Asp Leu Arg Ser Trp
545                 550                 555                 560

Leu Ser Asn Asn Val Arg Ser Asp Trp His Pro Val Gly Thr Cys Ala
                565                 570                 575

Met Leu Pro Lys Glu Leu Gly Gly Val Val Ser Pro Ala Leu Met Val
            580                 585                 590

Tyr Gly Thr Ser Asn Leu Arg Val Val Asp Ala Ser Ile Met Pro Leu
        595                 600                 605

Glu Val Ser Ser His Leu Met Gln Pro Thr Tyr Gly Ile Ala Glu Lys
    610                 615                 620

Ala Ala Asp Ile Ile Lys Asn Phe Tyr Lys Thr Gln His Lys Asn Gln
625                 630                 635                 640

Asn


<210> SEQ ID NO 2
<211> LENGTH: 1926
<212> TYPE: DNA
<213> ORGANISM: Mucor prainii

<400> SEQUENCE: 2

atgaagatca cagctgccat tatcactgtt gccacagcat ttgcttcttt tgcttctgct      60

caacaagaca caaattcttc ctcaactgat acttatgatt atgttatcgt tggcggcggt     120

gtagctggtt tggctttggc tagtcgtatc tctgaaaaca aggatgtcac tgttgctgtt     180

ctcgagtccg gtcctaatgc caatgataga tttgttgttt atgctcctgg catgtatggc     240

caagctgttg gcactgatct ctgtcctctc attcctacta ctcctcaaga aaatatgggc     300

aacagaagtc tcacaatcgc tactggtaga ttgctcggtg gtggcagtgc tattaatggt     360

ctcgtttgga cccgtggtgg cttgaaggat tacgatgctt gggaggagct cggtaaccct     420

ggatggaacg gtgccaactt gttcaagtac tttaagaagg tcgaaaactt cactcctcct     480

actcctgccc aaattgaata cggcgctact tatcagaaaa gtgctcatgg caagaaggga     540

cctattgatg tctctttcac gaactacgag ttctctcaat ctgctagctg gaacgcctca     600

ctcgaaaccc ttgatttcac tgcacttcct gatatcttga acggtacttt ggccggttac     660

tctaccactc ccaacatttt ggaccctgag actgttcaac gtgttgattc ctatactggt     720

tacattgctc cttacactag ccgtaacaac ctcaatgttt tggccaacca taccgtctcc     780

cgcattcaat ttgctcccaa gaatggtagc gaacctctca aggctaccgg tgttgaatgg     840

tatcccactg gcaacaagaa tcaaaagcaa attatcaagg cccgttatga agttatcatc     900

tcatctggtg ccattggtag tcctaagctt ttggaaatct ctggtatcgg taataaggat     960

atcgtctctg ctgctggtgt cgagtccttg attgacttgc ctggcgttgg ttccaacatg    1020

caagatcacg ttcatgctat cactgtctct actaccaata ttactggcta tactaccaac    1080

agcgtctttg tcaatgaaac ccttgcccaa gaacaaagag aagaatatga agccaacaag    1140

actggtatct gggctactac tcccaacaac ctcggttatc ctacgcccga acaactcttc    1200

aatggcaccg aattcgtttc tggaaaggag tttgctgaca agattcgtaa ctctactgat    1260
```

-continued

```
gaatgggcca actattatgc ttccaccaac gcctccaatg tcgagttatt aaagaagcaa   1320

tatgctattg tcgcctctcg ttacgaagag aactacttgt ctcctattga aatcaacttc   1380

actcctggtt atgagggtag cggtaatgtc gatttgcaaa acaacaagta ccaaactgtc   1440

aaccatgtct tgattgctcc tttaagtcgt ggttatactc acattaactc ttctgatgtg   1500

gaggatcatt ctgtcattaa tccccaatac tactctcatc ctatggatat tgatgtccat   1560

atcgcttcca ctaaacttgc tcgcgaaatc atcactgcct ctcccggtct tggtgacatt   1620

aacagtggcg aaatcgaacc cggtatgaat attacttctg aagacgacct tagatcttgg   1680

ttgagtaata atgtccgttc tgactggcat cctgttggta cttgtgctat gcttcccaag   1740

gaattaggtg gtgttgtcag ccccgctctc atggtttacg gcacttccaa cttgcgtgtt   1800

gttgatgctt cgattatgcc cctcgaagtc tcttctcatt tgatgcaacc cacctacggt   1860

attgctgaga aggctgctga cattattaag aatttctaca agactcaaca caagaaccaa   1920

aattag                                                              1926
```

```
<210> SEQ ID NO 3
<211> LENGTH: 641
<212> TYPE: PRT
<213> ORGANISM: Mucor prainii

<400> SEQUENCE: 3

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Ser Thr Asp Thr Tyr
            20                  25                  30

Asp Tyr Val Ile Val Gly Gly Gly Val Ala Gly Leu Ala Leu Ala Ser
        35                  40                  45

Arg Ile Ser Glu Asn Lys Asp Val Thr Val Ala Val Leu Glu Ser Gly
    50                  55                  60

Pro Tyr Ala Gly Asp Arg Phe Val Val Tyr Ala Pro Gly Met Tyr Gly
65                  70                  75                  80

Gln Ala Val Gly Thr Asp Leu Ala Pro Leu Ile Pro Thr Thr Pro Gln
                85                  90                  95

Glu Asn Met Gly Asn Arg Ser Leu Thr Ile Ala Thr Gly Arg Leu Leu
            100                 105                 110

Gly Gly Gly Ser Ala Ile Asn Gly Leu Val Trp Thr Arg Gly Gly Leu
        115                 120                 125

Lys Asp Tyr Asp Ala Trp Glu Glu Leu Gly Asn Pro Gly Trp Asn Gly
    130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Cys His
                165                 170                 175

Gly Lys Lys Gly Pro Ile Asp Val Ser Phe Thr Asn Tyr Glu Phe Ser
            180                 185                 190

Gln Ser Ala Ser Trp Asn Ala Ser Leu Glu Thr Leu Asp Phe Thr Ala
        195                 200                 205

Leu Pro Asp Ile Leu Cys Gly Thr Leu Ala Gly Tyr Ser Thr Thr Pro
    210                 215                 220

Asn Ile Leu Asp Pro Glu Thr Val Arg Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255
```

-continued

```
His Thr Val Ser Arg Ile Gln Phe Ala Pro Lys Asn Gly Ser Glu Pro
            260                 265                 270

Leu Lys Ala Thr Gly Val Glu Trp Tyr Pro Thr Gly Asn Lys Asn Gln
        275                 280                 285

Lys Gln Ile Ile Lys Ala Arg Tyr Glu Val Ile Ile Ser Ser Gly Ala
    290                 295                 300

Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
                325                 330                 335

Gly Ser Asn Met Gln Asp His Val His Ala Ile Thr Val Ser Thr Thr
            340                 345                 350

Asn Ile Thr Gly Tyr Thr Thr Asn Ser Val Phe Val Asn Glu Thr Leu
        355                 360                 365

Ala Gln Glu Gln Arg Glu Glu Tyr Glu Ala Asn Lys Thr Gly Ile Trp
    370                 375                 380

Ala Thr Cys Pro Asn Asn Leu Gly Tyr Pro Thr Pro Glu Gln Leu Phe
385                 390                 395                 400

Asn Gly Thr Glu Phe Val Ser Gly Lys Glu Phe Ala Asp Lys Ile Arg
                405                 410                 415

Asn Ser Thr Asp Glu Trp Ala Asn Tyr Tyr Ala Ser Thr Asn Ala Ser
            420                 425                 430

Asn Val Glu Leu Leu Lys Lys Gln Tyr Ala Ile Val Ala Ser Arg Tyr
        435                 440                 445

Glu Glu Asn Tyr Leu Ser Pro Ile Glu Ile Asn Phe Thr Pro Gly Tyr
    450                 455                 460

Glu Asp Ser Gly Asn Val Asp Leu Gln Asn Asn Lys Tyr Gln Thr Val
465                 470                 475                 480

Asn His Val Leu Ile Ala Pro Leu Ser Arg Gly Tyr Thr His Ile Asn
                485                 490                 495

Ser Ser Asp Val Glu Asp His Ser Val Ile Asn Pro Gln Tyr Tyr Ser
            500                 505                 510

His Pro Met Asp Ile Asp Val His Ile Ala Ser Thr Lys Leu Ala Arg
        515                 520                 525

Glu Ile Ile Thr Ala Ser Pro Gly Leu Gly Asp Ile Asn Ser Gly Glu
    530                 535                 540

Ile Glu Pro Gly Met Asn Ile Thr Ser Asp Asp Asp Val Arg Lys Trp
545                 550                 555                 560

Leu Ser Asn Asn Val Arg Ser Asp Trp His Pro Val Gly Thr Cys Ala
                565                 570                 575

Met Leu Pro Lys Glu Leu Gly Gly Val Val Ser Pro Ala Leu Met Val
            580                 585                 590

Tyr Gly Thr Ser Asn Leu Arg Val Val Asp Ala Ser Ile Met Pro Leu
        595                 600                 605

Glu Val Ser Ser His Leu Met Gln Pro Thr Tyr Gly Ile Ala Glu Lys
    610                 615                 620

Ala Ala Asp Ile Ile Lys Asn Phe Tyr Lys Thr Gln His Lys Asn Gln
625                 630                 635                 640

Asn
```

<210> SEQ ID NO 4
<211> LENGTH: 1926
<212> TYPE: DNA

<213> ORGANISM: Mucor prainii

<400> SEQUENCE: 4

```
atgaagatca cagctgccat tatcactgtt gccacagcat ttgcttcttt tgcttctgct     60
caacaagaca caaattcttc ctcaactgat acttatgatt atgttatcgt tggcggcggt    120
gtagctggtt tggctttggc tagtcgtatc tctgaaaaca aggatgtcac tgttgctgtt    180
ctcgagtccg gtccttatgc cggtgataga tttgttgttt atgctcctgg catgtatggc    240
caagctgttg gcactgatct cgctcctctc attcctacta ctcctcaaga aaatatgggc    300
aacagaagtc tcacaatcgc tactggtaga ttgctcggtg gtggcagtgc tattaatggt    360
ctcgtttgga cccgtggtgg cttgaaggat tacgatgctt gggaggagct cggtaaccct    420
ggatggaacg gtgccaactt gttcaagtac tttaagaagg tcgaaaactt cactcctcct    480
actcctgccc aaattgaata cggcgctact tatcagaaaa gttgtcatgg caagaaggga    540
cctattgatg tctctttcac gaactacgag ttctctcaat ctgctagctg gaacgcctca    600
ctcgaaaccc ttgatttcac tgcacttcct gatatcttgt gcggtacttt ggccggttac    660
tctaccactc ccaacatttt ggaccctgag actgttcgac gtgttgattc ctatactggt    720
tacattgctc cttacactag ccgtaacaac ctcaatgttt tggccaacca taccgtctcc    780
cgcattcaat ttgctcccaa gaatggtagc gaacctctca aggctaccgg tgttgaatgg    840
tatcccactg gcaacaagaa tcaaaagcaa attatcaagg cccgttatga agttatcatc    900
tcatctggtg ccattggtag tcctaagctt ttggaaatct ctggtatcgg taataaggat    960
atcgtctctg ctgctggtgt cgagtccttg attgacttgc ctggcgttgg ttccaacatg   1020
caagatcacg ttcatgctat cactgtctct actaccaata ttactggcta tactaccaac   1080
agcgtctttg tcaatgaaac ccttgcccaa gaacaaagag aagaatatga agccaacaag   1140
actggtatct gggctacttg tcccaacaac ctcggttatc ctacgcccga acaactcttc   1200
aatggcaccg aattcgtttc tggaaaggag tttgctgaca agattcgtaa ctctactgat   1260
gaatgggcca actattatgc ttccaccaac gcctccaatg tcgagttatt aaagaagcaa   1320
tatgctattg tcgcctctcg ttacgaagag aactacttgt ctcctattga aatcaacttc   1380
actcctggtt atgaggacag cggtaatgtc gatttgcaaa acaacaagta ccaaactgtc   1440
aaccatgtct tgattgctcc tttaagtcgt ggttatactc acattaactc ttctgatgtg   1500
gaggatcatt ctgtcattaa tccccaatac tactctcatc ctatggatat tgatgtccat   1560
atcgcttcca ctaaacttgc tcgcgaaatc atcactgcct ctcccggtct tggtgacatt   1620
aacagtggcg aaatcgaacc cggtatgaat attacttctg acgacgacgt tagaaaatgg   1680
ttgagtaata atgtccgttc tgactggcat cctgttggta cttgtgctat gcttcccaag   1740
gaattaggtg gtgttgtcag ccccgctctc atggtttacg gcacttccaa cttgcgtgtt   1800
gttgatgctt cgattatgcc cctcgaagtc tcttctcatt tgatgcaacc cacctacggt   1860
attgctgaga aggctgctga cattattaag aatttctaca agactcaaca caagaaccaa   1920
aattag                                                              1926
```

MEDIATOR

CROSS-REFERENCE TO RELATED APPLICATIONS

This application is a 371 of PCT/JP2019/007373, filed Feb. 26, 2019, which claims the benefit of Japanese Patent Application No. 2018-077593, filed Apr. 13, 2018 and Japanese Patent Application No. 2018-077628, filed Apr. 13, 2018

TECHNICAL FIELD

The present invention relates to the application of a phenylenediamine type compound (phenylenediamine compounds) as a mediator and an electrode modifying agent comprising the compound, an electrode comprising the compound, an enzyme sensor comprising the electrode, as well as a battery. The present invention also relates to electrochemical measurement using the phenylenediamine type compound and an oxidoreductase, a composition comprising the phenylenediamine type compound and an oxidoreductase, as well as an electrode comprising the phenylenediamine type compound.

BACKGROUND ART

In enzyme electrodes, mediators are utilized as intermediary substances for delivering electrons generated through enzyme-catalyzed redox reaction to electrodes. For efficient electron transfer from an enzyme to an electrode, it is desirable for the mediator to be localized in proximity to the electrode. Therefore, various approaches of fixing the mediator to the electrode have been utilized, such as a method of chemically binding the mediator to the electrode, and a method of polymerizing the mediator itself. However, the chemical binding method is limited by the side chain functional group of the mediator, and the method of polymerizing the mediator itself may change the redox potential of the mediator. Thus, conventional approaches lacked versatility. There is also a report on treating glassy carbon electrodes with strong acids, and thereby activating functional groups on the surface for adsorptive fixation of mediators such as quinones. However, this approach has hardly been put into practical use in the industry.

Further, all of these methods require complicated steps for the fixation of the mediator to the electrode, and are associated with the problem of high cost. Accordingly, an electron mediator that can be conveniently used without the need of complicated steps for fixation to electrodes was needed.

Patent Literature 1 (JP Patent Publication (Kokai) No. 7-234201) describes a p-phenylenediamine compound as an electron mediator for use in an electrochemical measurement method. The p-phenylenediamine compound disclosed therein is a p-phenylenediamine derivative having one or more groups selected from the group consisting of a hydroxyl group, a mercapto group, a carboxy group, a phosphonooxy group and a sulfo group.

Patent Literature 2 (WO 2004/011929) has reported that after surface activation of carbon particles by an acid treatment, N,N'-diphenyl-p-phenylenediamine (DPPD) is added to the acid-treated carbon powder, and then this carbon powder is immobilized to a carbon electrode; and that hydrogen sulfide or thiol in a solution is detected using the electrode.

Patent Literature 3 (JP Patent Publication (Kohyo) No. 2007-526474) describes an electrode comprising carbon derivatized with N,N'-diphenyl-p-phenylenediamine, and a pH sensor using the electrode.

Patent Literature 4 (JP Patent Publication (Kokai) No. 2008-185534) describes a phenylenediamine type compound 2,3,5,6-tetramethyl-1,4-phenylenediamine or N,N-dimethyl-p-phenylenediamine as a mediator, and ethanol measurement using the same.

Patent Literature 5 (JP Patent Publication (Kokai) No. 2016-042032) describes N,N,N',N'-tetramethyl-1,4-phenylenediamine as a mediator, and glucose measurement using the same.

N-isopropyl-N'-phenyl-p-phenylenediamine (IPPD), N,N'-diphenyl-p-phenylenediamine (DPPD), and N-(1,3-dimethylbutyl)-N'-phenyl-p-phenylenediamine (6PPD) are all known as rubber antioxidants (Non Patent Literature 2, NIPPON GOMU KYOKAISHI, the Journal of The Society of Rubber Science and Technology, Japan, Vol. 82, No. 2, 2009, p. 45-49).

Non Patent Literature 1 (Analyst, 2003, 128, 473-479) has reported that after carbon surface activation of a carbon powder by acid treatment with 0.1 M hydrochloric acid, DPPD is added to the acid-treated carbon powder, and this carbon powder is immobilized to a carbon electrode (basal plane pyrolytic graphite electrode: BPPG electrode), and that sulfide is detected using the electrode. Patent Literature 6 describes a flow battery.

CITATION LIST

Patent Literature

Patent Literature 1: JP Patent Publication (Kokai) No. 7-234201
Patent Literature 2: WO 2004/011929
Patent Literature 3: JP Patent Publication (Kohyo) No. 2007-526474 (WO 2005/085825)
Patent Literature 4: JP Patent Publication (Kokai) No. 2008-185534
Patent Literature 5: JP Patent Publication (Kokai) No. 2016-042032
Patent Literature 6: JP Patent Publication (Kokai) No. 2019-003928

Non Patent Literature

Non Patent Literature 1: Analyst, 2003, 128, 473-479
Non Patent Literature 2: NIPPON GOMU KYOKAISHI, the Journal of The Society of Rubber Science and Technology, Japan, Vol. 82, No. 2, 2009, p. 45-49

SUMMARY OF INVENTION

Technical Problem

An object of the present invention is to provide a novel mediator that can at least partially solve the problems described above.

Solution to Problem

The present inventors have carried out extensive studies to attain the object and found that, surprisingly, a phenylenediamine type compound can be adsorbed onto an electrode surface without the need of special treatment such as an acid treatment, and the compound is capable of functioning as a mediator, thereby completing the present invention. To the best of the present inventors' knowledge, there is no previous report stating that IPPD, DPPD, or 6PPD are mediators that can be adsorbed onto electrodes and this is a surprising finding. The present inventors have also found, surprisingly, a further phenylenediamine type compound that can be adsorbed onto an electrode surface without the need of special treatment such as an acid treatment.

The present invention encompasses the following embodiments:

[1] An electrode modifying agent comprising a compound having a property of being adsorbed, without being bound to a polymer or without being polymerized, onto an electrode untreated with an acid.

[2] An electron transfer promoting agent comprising a compound having a property of being adsorbed, without being bound to a polymer or without being polymerized, onto an electrode untreated with an acid.

[3] A battery comprising the electrode modifying agent according to embodiment 1 or the electron transfer promoting agent according to embodiment 2.

[4] The battery according to embodiment 3, wherein the compound is immobilized to an electrode of the battery.

[5] The battery according to embodiment 3 or 4, comprising an oxidoreductase.

[6] The battery according to embodiment 5, wherein the oxidoreductase is immobilized to the electrode.

[7] A composition comprising the electrode modifying agent according to embodiment 1 or the electron transfer promoting agent according to embodiment 2.

[8] An electrode comprising the electrode modifying agent according to embodiment 1 or the electron transfer promoting agent according to embodiment 2.

[9] The electrode according to embodiment 8, having an enzyme, or the composition according to embodiment 7, comprising an enzyme.

[10] The electrode or the composition according to embodiment 9, wherein the enzyme is an oxidoreductase.

[11] The electrode according to embodiment 10, wherein the oxidoreductase is immobilized.

[12] A sensor comprising the electrode modifying agent according to embodiment 1 or the electron transfer promoting agent according to embodiment 2, or an enzyme sensor having an electrode according to embodiment 10 or 11.

[13] The electrode modifying agent according to embodiment 1, the electron transfer promoting agent according to embodiment 2, the battery according to any of embodiments 3 to 6, the composition according to embodiment 7, 9 or 10, the electrode according to any of embodiments 8 to 11, or the enzyme sensor according to embodiment 12, wherein the compound is a compound having a structure of formula I or formula II:

[Formula 1]

(I)

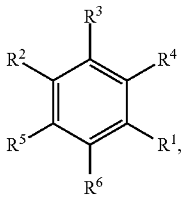

or (II)

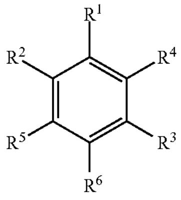

wherein $R^1$ is $-NR^7R^8$, $-N{=}N-R^9$, or —N'+N, $R^2$ is $-NR^{10}R^{11}$ or $-N{=}N-R^{12}$, $R^7$ and $R^8$ are each independently hydrogen, or linear or branched $C_{1-7}$ alkyl, $C_{1-7}$ alkenyl, $C_{1-7}$ alkynyl, $C_{3-9}$ cycloalkyl, phenyl, 1-naphthyl, 2-naphthyl, anthracenyl, phenanthrenyl, acetyl, carboxy, furanylformyl, pyrazolylformyl, 1-methyl-1H-pyrazol-5-ylformyl, 9,9-dimethylfluoren-2-yl, $-N^+{=}N$, $-N{=}N$-phenyl, benzyl,

[Formula 2]

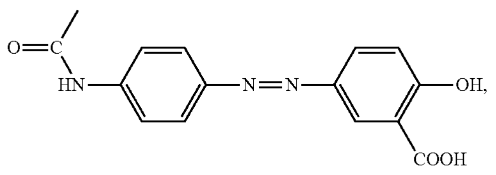

, or

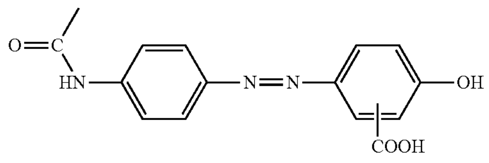

which may optionally be substituted with one or more X or V, $R^{10}$ is hydrogen, or linear or branched $C_{1-7}$ alkyl, $C_{1-7}$ alkenyl, $C_{1-7}$ alkynyl, $C_{3-9}$ cycloalkyl, phenyl, 1-naphthyl, 2-naphthyl, anthracenyl or phenanthrenyl, which may optionally be substituted with one or more X or V, $R^3$, $R^4$, $R^5$ and $R^6$ are each independently hydrogen, or linear or branched $C_{1-7}$ alkyl, $C_{1-7}$ alkenyl, $C_{1-7}$ alkynyl, $C_{1-7}$ alkoxy, halo, nitro, cyano, carboxy, sulfo, hydroxy or amino, which may optionally be substituted with one or more Y, or $R^3$ and $R^4$, or $R^5$ and $R^6$, together with the benzene ring containing these moieties, form a benzene ring or

[Formula 3]

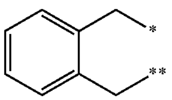

or

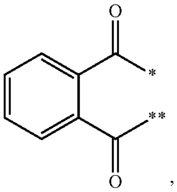

, which may optionally be substituted with one or more oxo, X or W, wherein * is bonded to the carbon atom bonded to $R^3$, and ** is bonded to the carbon atom bonded to $R^4$, or * is bonded to the carbon atom bonded to $R^5$, and ** is bonded to the carbon atom bonded to $R^6$, $R^{11}$ is selected from the group consisting of phenyl, 1-naphthyl, 2-naphthyl, anthracenyl and phenanthrenyl, which may optionally be substituted with one or more X or Z, $R^9$ is selected from the group consisting of hydrogen, and phenyl, 1-naphthyl, 2-naphthyl, anthracenyl and phenanthrenyl, which may optionally be substituted with one or more X, $R^{12}$ is selected from the group consisting of phenyl, 1-naphthyl, 2-naphthyl, anthracenyl, phenanthrenyl, and

[Formula 4]

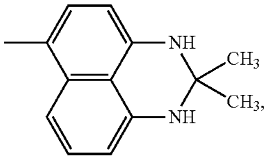

which may optionally be substituted with one or more X, W, isothiocyanate, or halosulfonyl, wherein V is —O-acryloyl, acetylamino, or phenyl, which may optionally be substituted with $C_{1-7}$ alkyl, W is D- or L-alanylsulfonyl, D- or L-valylsulfonyl, D- or L-leucylsulfonyl, D- or L-methionylsulfonyl, D- or L-prolylsulfonyl, D- or L-tryptophylsulfonyl, D- or L-glycylsulfonyl, D- or L-cysteinylsulfonyl, D- or L-isoleucylsulfonyl, D- or L-phenylalanylsulfonyl, D- or L-tyrosylsulfonyl, D- or L-serylsulfonyl, D- or L-threonylsulfonyl, D- or L-asparaginylsulfonyl, D- or L-glutamylsulfonyl, D- or L-arginylsulfonyl, D- or L-histidylsulfonyl, D- or L-lysylsulfonyl, D- or L-asparagylsulfonyl, D- or L-glutaminylsulfonyl, —C(═O)—O-succinimidyl, acetyl, trifluoroacetyl, benzoylamino, —N═N-phenyl, phenylamino, or diaminophenylazophenyl, which may optionally be substituted with one or more amino, $C_{1-7}$ alkyl, or aminoalkyl, or phenylazo, which may optionally be substituted with one or more X, naphthylazo, which may optionally be substituted with one or more Y, acetylamino,

[Formula 5]

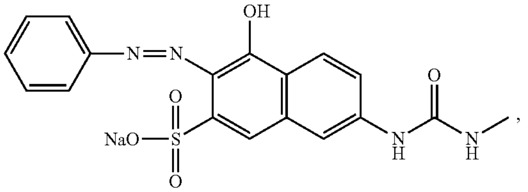

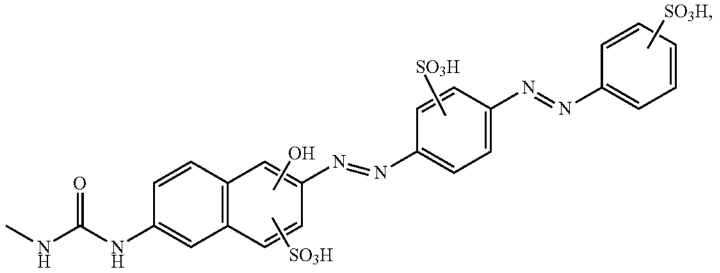

or

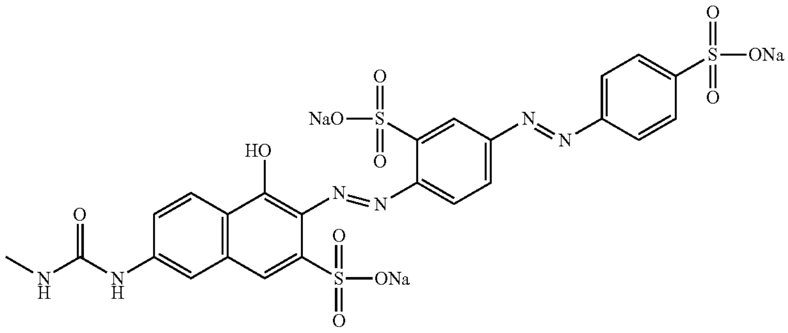

X is linear or branched $C_{1-7}$ alkyl, $C_{1-7}$ alkenyl, $C_{1-7}$ alkynyl, $C_{1-7}$ alkoxy, halo, hydroxy, nitro, carboxy, cyano, sulfo, amino or alkylamino, which may optionally be substituted with one or more substituents selected from the group consisting of halo, amino, cyano, carboxy, carbonyl, alkoxy, alkylamino, nitroso, nitro and sulfo, Y is selected from the group consisting of halo, amino, cyano, carboxy, carbonyl, hydroxy, alkoxy and sulfo, and Z is $—SO_2—CH═CH_2$, $—SO_2—C_2H_4—O—SO_3H$, or 4,6-dichlorotriazin-2-ylamino, or a salt, an anhydride or a solvate thereof.

[14] The electrode modifying agent, electron transfer promoting agent, battery, composition, electrode, or sensor according to embodiment 13, wherein the compound is a compound having a structure of formula Ia or IIa:

[Formula 6]

(Ia))

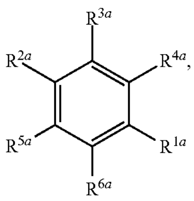

or (IIa)

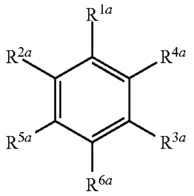

wherein $R^{1a}$ is $—NR^{7a}R^{8a}$, $—N═N—R^{9a}$, or $—N^+≡N$, $R^{2a}$ is $—NR^{10a}R^{11a}$, or $—N═N—R^{2a}$, $R^{7a}$ and $R^{8a}$ are each independently hydrogen, or linear or branched $C_{1-6}$ alkyl, $C_{1-6}$ alkenyl, $C_{1-6}$ alkynyl, $C_{3-9}$ cycloalkyl, phenyl, 1-naphthyl, 2-naphthyl, anthracenyl, or phenanthrenyl, which may optionally be substituted with one or more Xa, $R^{10}$ is hydrogen, or linear or branched $C_{1-6}$ alkyl, $C_{1-6}$ alkenyl, $C_{1-6}$ alkynyl, $C_{3-9}$ cycloalkyl, phenyl, 1-naphthyl, 2-naphthyl, anthracenyl or phenanthrenyl, which may optionally be substituted with one or more Xa, $R^{3a}$, $R^{4a}$, $R^{8a}$ and $R^{6a}$ are each independently hydrogen, or linear or branched $C_{1-6}$ alkyl, $C_{1-6}$ alkenyl, $C_{1-6}$ alkynyl, $C_{1-6}$ alkoxy, halo, nitro, cyano, carboxy, sulfo, hydroxy or amino, which may optionally be substituted with one or more Y, or $R^{3a}$ and $R^{4a}$, or $R^{8a}$ and $R^{6a}$ form a benzene ring, or

[Formula 7]

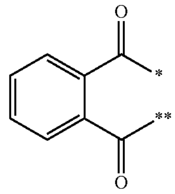

wherein * is bonded to the carbon atom bonded to $R^{3a}$, and ** is bonded to the carbon atom bonded to $R^{4a}$, or * is bonded to the carbon atom bonded to $R^{8a}$, and ** is bonded to the carbon atom bonded to $R^{6a}$, $R^{11a}$ is selected from the group consisting of phenyl, 1-naphthyl, 2-naphthyl, anthracenyl and phenanthrenyl, which may optionally be substituted with one or more Xa, $R^{9a}$ and $R^{12a}$ are each independently selected from the group consisting of hydrogen, and phenyl, 1-naphthyl, 2-naphthyl, anthracenyl and phenanthrenyl, which may optionally be substituted with one or more Xa, Xa is linear or branched $C_{1-6}$ alkyl, $C_{1-6}$ alkenyl, $C_{1-6}$ alkynyl, $C_{1-6}$ alkoxy, halo, hydroxy, nitro, carboxy, cyano, sulfo, amino or alkylamino, which may optionally be substituted with one or more substituents selected from the group consisting of halo, amino, cyano, carboxy, carbonyl, hydroxy, alkoxy, alkylamino, nitroso, nitro and sulfo, and Y is selected from the group consisting of halo, amino, cyano, carboxy, carbonyl, alkoxy and sulfo, or having a structure of formula Ib or IIb:

[Formula 8]

(Ib)

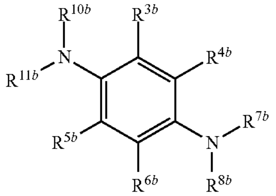

or (IIb)

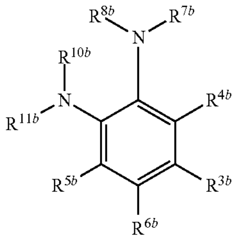

wherein $R^{7b}$, $R^{8b}$ and $R^{10b}$ are each independently hydrogen, or linear or branched $C_{1-6}$ alkyl, $C_{1-6}$ alkenyl, $C_{1-6}$ alkynyl, $C_{3-9}$ cycloalkyl, phenyl, 1-naphthyl, 2-naphthyl, anthracenyl or phenanthrenyl, which may optionally be substituted with one or more Xb, $R^{3b}$, $R^{4b}$, $R^{5b}$ and $R^{6b}$ are each independently hydrogen, or linear or branched $C_{1-6}$ alkyl, $C_{1-6}$ alkenyl, $C_{1-6}$ alkynyl, $C_{1-6}$ alkoxy, halo, nitro, cyano, carboxy, sulfo or amino, which may optionally be substituted with one or more Y, $R^{11b}$ is selected from the group consisting of phenyl, 1-naphthyl, 2-naphthyl, anthracenyl and phenanthrenyl, which may optionally be substituted with one or more Xb, wherein Xb is linear or branched $C_{1-6}$ alkyl, $C_{1-6}$ alkenyl, $C_{1-6}$ alkynyl, $C_{1-6}$ alkoxy, halo, hydroxy, nitro, carboxy, cyano, sulfo or amino, which may optionally be substituted with one or more substituents selected from the group consisting of halo, amino, cyano, carboxy, carbonyl, alkoxy and sulfo, and Y is selected from the group consisting of halo, amino, cyano, carboxy, carbonyl, alkoxy and sulfo, or a salt, an anhydride or a solvate thereof.

[15] The electrode modifying agent, electron transfer promoting agent, battery, composition, electrode or sensor according to embodiment 13 or 14, wherein the compound is selected from the group consisting of

[Formula 9]

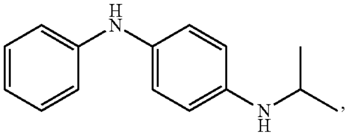

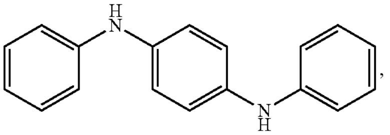

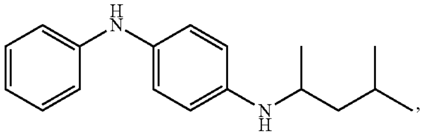

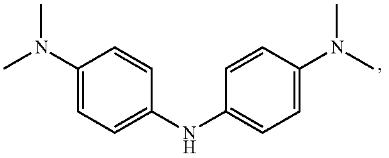

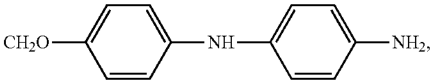

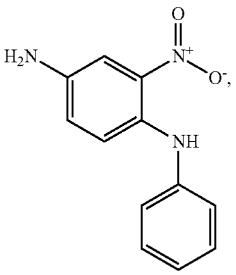

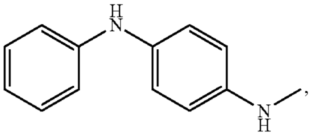

-continued

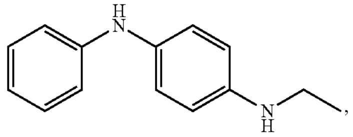

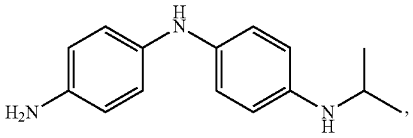

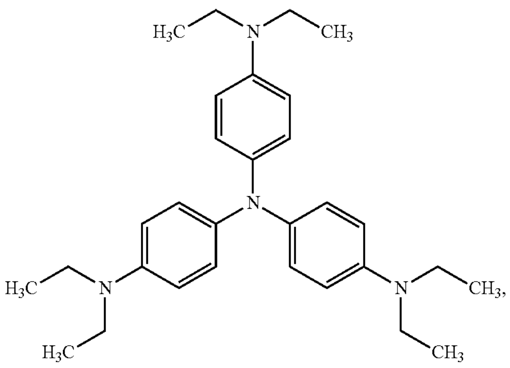

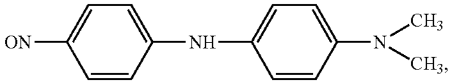

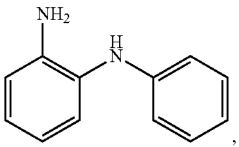

,

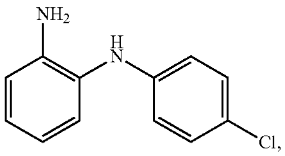

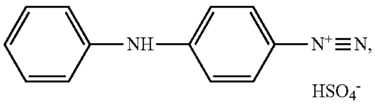

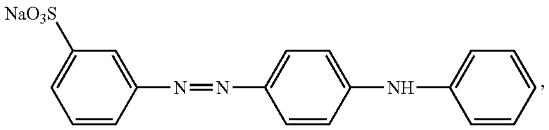

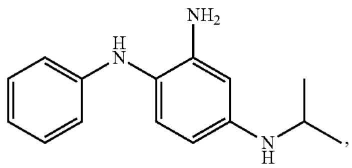

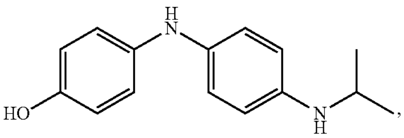

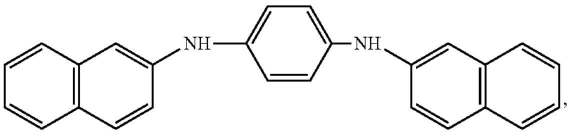

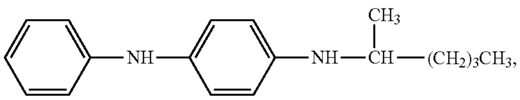

-continued

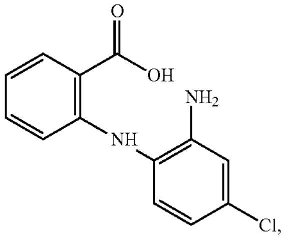

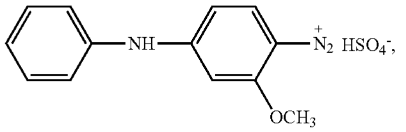

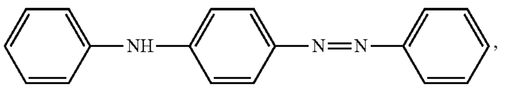

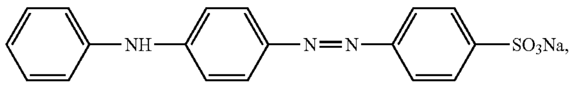

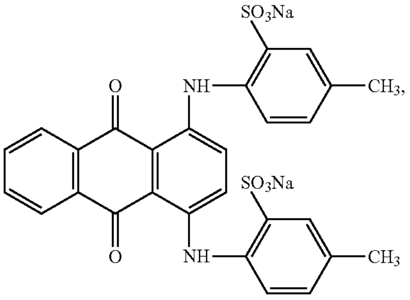

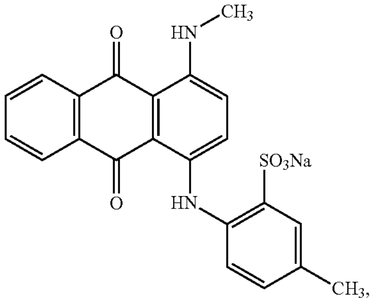

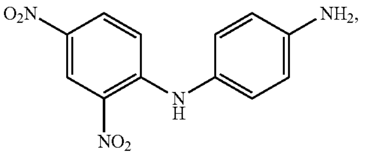

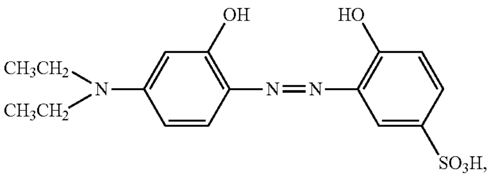

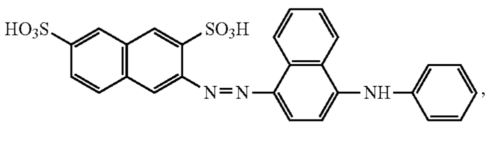

-continued

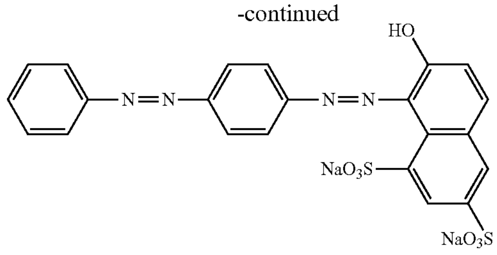

and

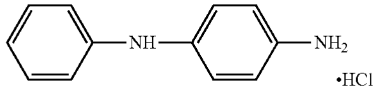

[16] A method for producing a battery, comprising the step of using the electrode modifying agent according to embodiment 1 or the electron transfer promoting agent according to embodiment 2.

[17] The method according to embodiment 16, comprising the step of contacting the electrode modifying agent or the electron transfer promoting agent with an electrode of the battery.

[18] A power generation method using a battery according to any of embodiments 3 to 6 and 13 to 15.

[19] An electrochemical measurement method using the composition according to any of embodiments 7, 9, 10 and 13 to 15, the electrode according to any of embodiments 8 to 11 and 13 to 15, or the sensor according to any of embodiments 12 to 15.

[20] A method for modifying or altering an electrode, comprising the step of contacting the electrode modifying agent according to any of embodiments 1 and 13 to 15, the electron transfer promoting agent according to any of embodiments 2 and 13 to 15, or the composition according to any of embodiments 7, 9, 10 and 13 to 15, with the electrode.

The present specification encompasses the contents disclosed in Japanese Patent Application Nos. 2018-077593 and 2018-077628 on which the priority of the present application is based.

Advantageous Effects of Invention

The phenylenediamine type compound of the present invention, unlike conventional mediators such as p-phenylenediamine, can be adsorbed directly onto electrode surface without the need of special treatment such as the acid treatment of electrodes or the polymerization of the mediator itself, and can therefore be conveniently immobilized onto an electrode. Furthermore, such electrode can be used in electrochemical measurements. Moreover, such electrode can be applied to batteries.

PHENYLENEDIAMINE TYPE COMPOUND

Figure 1:
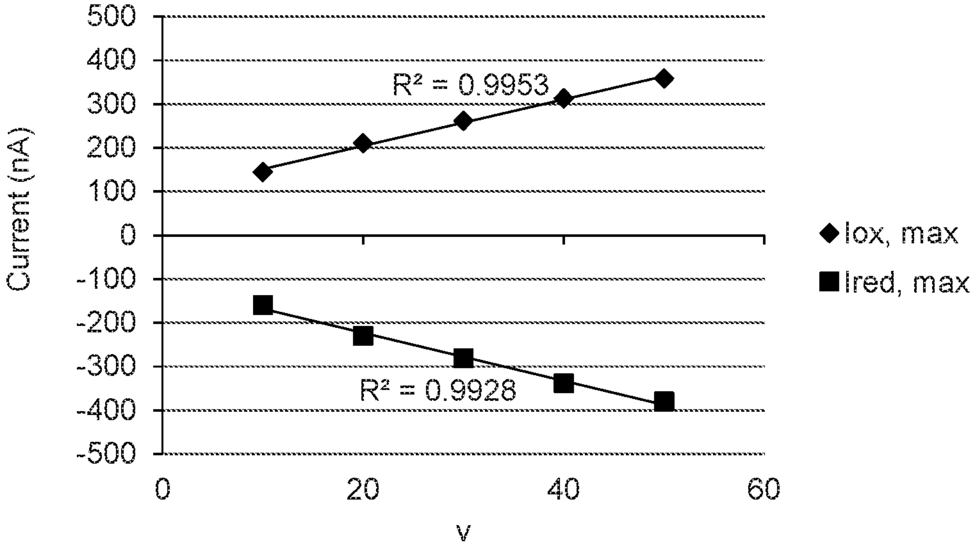
FIG. 1 shows results of carrying out cyclic voltammetry using IPPD and GDH and plotting a sweep rate and $I_{Omax}$ and $I_{Rmax}$.

(Electrode onto which the Phenylenediamine Type Compound is Adsorbed)

In one embodiment, the present invention provides a phenylenediamine type compound (phenylenediamine compounds). While the compound of the present invention also includes azo compounds and diazonio compounds, in the present specification for the sake of convenience, the term phenylenediamine type compound (phenylenediamine compounds), or the phenylenediamine type compound of the present invention includes not only compounds having a phenylenediamine skeleton but also azo compounds and diazonios compound. In another embodiment, the present invention provides an electrode modifying agent comprising the phenylenediamine type compound. This electrode modifying agent can be adsorbed onto electrode surface and is capable of modifying the electron accepting properties of the electrode. In another embodiment, the present invention provides an electrode onto which the phenylenediamine type compound or the electrode modifying agent of the present invention is adsorbed. In another embodiment, the present invention provides a composition for electrochemical measurement comprising the phenylenediamine type compound or the electrode modifying agent of the present invention. The composition may further comprise an enzyme. The enzyme may be an oxidoreductase. In another embodiment, the present invention provides a kit for electrochemical measurement comprising the phenylenediamine type compound or the electrode modifying agent of the present invention. In the present specification, the electrode modifying agent is also referred to as an electrode adsorber agent.

The phenylenediamine type compound of the present invention can be contacted with an electrode and thereby adsorbed onto the electrode surface. This adsorption onto an electrode does not require a special procedure such as the activation of electrode surface by an acid treatment. In one embodiment, the property of being adsorbed onto an electrode, possessed by the compound of the present invention refers to a property of the compound of being physically adsorbed onto an electrode. An electrode made of a material such as carbon, gold, or platinum can be used. Further, aspects are included in which the compound is adsorbed onto a primary material such as a carbon powder or a carbon material and subsequently the primary material such as a carbon powder or a carbon material is immobilized (fixed) to an electrode. However, these descriptions are merely for illustrating the properties possessed by the compound of the present invention and do not limit the method of use of the compound. That is, in one embodiment, the present invention provides a method of adsorbing the compound of the present invention onto a primary material such as a carbon powder or a carbon material, and subsequently fixing the primary material such as a carbon powder or a carbon material to an electrode.

In one embodiment, the present invention provides a primary material such as a carbon powder or a carbon material on which the compound of the present invention is adsorbed. This primary material such as a carbon powder or a carbon material can be applied to or coated onto an electrode. Examples of the primary material include, but are not limited to, carbon, platinum, and gold. Examples of the carbon material include carbon black, carbon fiber, single-layered or multilayered carbon nanotubes, graphene, and ketjen black.

In one embodiment, the property of being adsorbed onto an electrode, a carbon powder or a carbon material, possessed by the compound of the present invention refers to a property of the compound capable of being physically adsorbed directly onto an electrode, a carbon powder or a carbon material, and does not refer to a property of the compound of binding to an electrode, a carbon powder or a carbon material through covalent binding via a polymer or a linker. In the present specification, such property is also referred to as a property of being adsorbed onto an electrode without being bound to a polymer, or a property of being adsorbed onto a carbon powder or a carbon material without being bound to a polymer or without (the compound) being polymerized. However, these descriptions are merely for illustrating the properties possessed by the compound of the present invention and do not limit the method of use of the compound. That is, in one embodiment, the present invention provides a method of binding the compound of the present invention to an electrode, a carbon powder or a carbon material via covalent binding to a polymer or a linker. That the compound can be physically adsorbed directly onto an electrode, a carbon powder or a carbon material does not exclude the covalent binding of the compound of the present invention per se to a carbon powder or a carbon material. In the present specification, the polymer refers to, for example, a multimerized form of 10 or more identical units.

In one embodiment, the carbon powder or the carbon material, the carbon electrode, the gold electrode, or the platinum electrode for adsorbing the compound of the present invention is not treated with an acid. That is, in one embodiment, a carbon powder or a carbon material, or a carbon electrode treated with an acid is excluded from the carbon powder or the carbon material onto which the compound of the present invention is to be adsorbed.

In one embodiment, the compound of the present invention can be used in combination with an enzyme. In one embodiment, the compound of the present invention can be used in combination with an oxidoreductase. In one embodiment, the compound of the present invention can be used as an electron transfer promoting agent. In one embodiment, the phenylenediamine type compound of the present invention functions as a mediator in redox reaction catalyzed by an oxidoreductase. Examples of the oxidoreductase include, but are not limited to, various oxidoreductases classified into EC 1, for example, glucose oxidase, glucose dehydrogenase, amadoriase (also referred to as fructosyl peptide oxidase or fructosyl amino acid oxidase), peroxidase, galactose oxidase, bilirubin oxidase, pyruvate oxidase, D- or L-amino acid oxidase, amine oxidase, cholesterol oxidase, choline oxidase, xanthine oxidase, sarcosine oxidase, D- or L-lactate oxidase (LOD), ascorbate oxidase, cytochrome oxidase, alcohol dehydrogenase, cholesterol dehydrogenase, aldehyde dehydrogenase, aldehyde oxidase, fructose dehydrogenase (FDH), sorbitol dehydrogenase, D- or L-lactate dehydrogenase, malate dehydrogenase, glycerol dehydrogenase, 17B hydroxysteroid dehydrogenase, estradiol 17B dehydrogenase, D- or L-amino acid dehydrogenase, glyceraldehyde 3-phosphate dehydrogenase, 3-hydroxysteroid dehydrogenase, diaphorase, catalase, glutathione reductase, cytochrome b5 reductase, adrenoxine reductase, cytochrome b5 reductase, adrenodoxin reductase, nitrate reductase, phosphate dehydrogenase, bilirubin oxidase, laccase, polyamine oxidase, formate dehydrogenase, pyranose oxidase, pyranose dehydrogenase, and tauropine dehydrogenase. Further, a plurality of enzymes may be combined. Examples of the coenzyme of the enzymes above include nicotinamide adenine dinucleotide (NAD), nicotinamide adenine dinucleotide phosphate, flavin adenine dinucleotide (FAD), and pyrroloquinolinequinone. That is, examples of the glucose dehydrogenase (GDH) include FAD-dependent GDH, NAD-dependent GDH, and PQQ-dependent GDH. The oxidoreductases listed above can be subjected to activity measurement using various substrates by methods described in, for example, Methods in Enzymology (Vol. 1-602).

In the present specification, the phrase "functioning as a mediator" means that the phenylenediamine type compound contributes to electron migration. For example, in a system using an electrode, the phenylenediamine type compound of the present invention becomes a reduced form by receiving an electron from an oxidoreductase and returns to the oxidized form by giving an electron to the electrode. From such a perspective, the phenylenediamine type compound of the present invention functioning as a mediator can also be referred to as an electron migration intermediary agent, an electron transfer promoting agent, or an electron mediator (also referred to simply as a mediator). In the present specification, these terms are used interchangeably.

In one embodiment, an electrode having a carbon powder or carbon particles treated with an acid is excluded from the electrode of the present invention.

In one embodiment, the oxidoreductase that is used with the electrode of the present invention may be immobilized to the electrode. That is, in this embodiment, the present invention provides an electrode onto which an oxidoreductase is immobilized and the electrode modifying agent of the present invention is adsorbed. In one embodiment, the present invention provides an enzyme sensor comprising an electrode onto which an oxidoreductase is immobilized and the electrode modifying agent of the present invention is adsorbed. In one embodiment, the present invention provides a sensor comprising the electrode modifying agent or the electron transfer promoting agent of the present invention.

The phenylenediamine type compound of the present invention or the electrode modifying agent, the electrode adsorber or the electron transfer promoting agent comprising the phenylenediamine type compound can be adsorbed onto electrode surface without the need of a special treatment. Thus, in one embodiment, the phenylenediamine type compound, the electrode modifying agent, the electrode adsorber or the electron transfer promoting agent of the present invention may be adsorbed onto an electrode in advance in order to prepare a modified electrode. In another embodiment, a measurement solution (composition) comprising the phenylenediamine type compound, the electrode modifying agent, the electrode adsorber or the electron transfer promoting agent of the present invention, and oxidoreductase can be used when performing an electrochemical measurement. In this embodiment, when the composition comprising the phenylenediamine type compound, the electrode modifying agent, the electrode adsorber or the electron transfer promoting agent of the present invention, and an oxidoreductase is physically brought into contact with an electrode, the phenylenediamine type compound, the electrode modifying agent, the electrode adsorber or the electron transfer promoting agent of the present invention is adsorbed onto the electrode so that an electrode with modified electrochemical characteristics (properties) is prepared on the spot at the time of measurement (in situ).

In one embodiment, the electrode is not pretreated with an acid when the phenylenediamine type compound, the electrode modifying agent, the electrode adsorber or the electron transfer promoting agent of the present invention is adsorbed onto the electrode. In another embodiment, the electrode may be pretreated with an acid prior to adsorption of the phenylenediamine type compound, the electrode modifying agent, the electrode adsorber or the electron transfer promoting agent of the present invention onto the electrode. In this context, the pretreatment with an acid includes contact of an electrolyte solution containing an acid with the electrode. In the present specification, an acid refers to an acid of pH 4 or lower, for example, lower than pH 4, pH 3 or lower, lower than pH 3, pH 2 or lower, lower than pH 2, or pH 1. In one embodiment, the phenylenediamine type compound, the electrode modifying agent, the electrode adsorber or the electron transfer promoting agent of the present invention may be converted to an oxidized form or a reduced form by applying a particular potential, and then be adsorbed onto an electrode. As an approach of converting the compound to an oxidized from or a reduced form, an oxidizing agent or a reducing agent may be used, and the approach is not particularly limited. In one embodiment, the phenylenediamine type compound, the electrode modifying agent, the electrode adsorbed agent or the electron transfer promoting agent of the present invention may be embedded in a polymer and adsorbed onto an electrode. In the present specification, such adsorption may also be referred to as embedding or entrapment. This is distinguished from adsorptive fixation, i.e., fixation by physical adsorption. The compound of the present invention in an embedding or entrapment can be diffused within the polymer, whereas, in adsorptive fixation, the compound of the present invention is not or almost not diffused. In another embodiment, the compound, the electrode modifying agent, the electrode adsorber agent or the electron transfer promoting agent of the present invention may be adsorbed onto an electrode through electrostatic interaction using an ionic polymer, for example, a cationic polymer such as polyethylenimine or polylysine, or an anionic polymer such as polyaniline or polyacrylic acid. In another embodiment, the compound, the electrode modifying agent, the electrode adsorber agent or the electron transfer promoting agent of the present invention may be adsorbed or immobilized via a cross-linking agent onto an enzyme, and then immobilized, together with the enzyme, onto an electrode. In another embodiment, the adsorbed compound of the present invention may be polymerized through redox reaction or by a cross-linking agent.

In one embodiment, the phenylenediamine type compound of the present invention may be a compound of the following general formula I or II, or a salt, an anhydride or a solvate thereof:

[Formula 10]

(I)

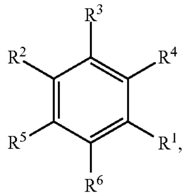

or (II)

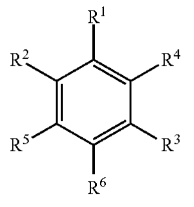

wherein $R^1$ is —$NR^7R^8$, —N═N—$R^9$, or —$N^+$═N, $R^2$ is —$NR^{10}R^{11}$ or —N═N—$R^{12}$, $R^7$ and $R^8$ are each independently hydrogen, or linear or branched $C_{1-7}$ alkyl, $C_{1-7}$ alkenyl, $C_{1-7}$ alkynyl, $C_{3-9}$ cycloalkyl, phenyl, 1-naphthyl, 2-naphthyl, anthracenyl, phenanthrenyl, acetyl, carboxy, furanylformyl, pyrazolylformyl, 1-methyl-1H-pyrazol-5-ylformyl, 9,9-dimethylfluoren-2-yl, —$N^+$═N, —N═N-phenyl, benzyl,

[Formula 11]

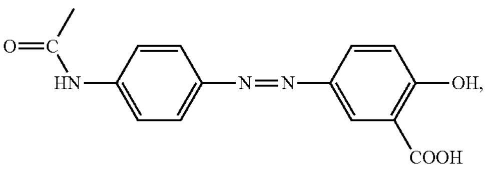

or

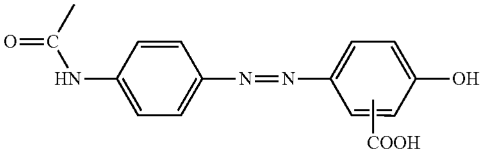

which may optionally be substituted with one or more X or V, $R^{10}$ is hydrogen, or linear or branched $C_{1-7}$ alkyl, $C_{1-7}$ alkenyl, $C_{1-7}$ alkynyl, $C_{3-9}$ cycloalkyl, phenyl, 1-naphthyl, 2-naphthyl, anthracenyl or phenanthrenyl, which may optionally be substituted with one or more X or V, $R^3$, $R^4$, $R^5$ and $R^6$ are each independently hydrogen, or linear or branched $C_{1-7}$ alkyl, $C_{1-7}$ alkenyl, $C_{1-7}$ alkynyl, $C_{1-7}$ alkoxy, halo, nitro, cyano, carboxy, sulfo, hydroxy or amino, which may optionally be substituted with one or more Y, or $R^3$ and $R^4$, or $R^5$ and $R^6$, together with the benzene ring containing these moieties, form a benzene ring, or

[Formula 12]

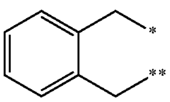

or

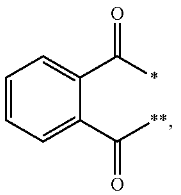

which may optionally be substituted with one or more oxo, X or W, wherein * is bonded to the carbon atom bonded to $R^3$, and ** is bonded to the carbon atom bonded to $R^4$, or * is bonded to the carbon atom bonded to $R^5$, and ** is bonded to the carbon atom bonded to $R^6$, $R^{11}$ is selected from the group consisting of phenyl, 1-naphthyl, 2-naphthyl, anthracenyl and phenanthrenyl, which may optionally be substituted with one or more X or Z, $R^9$ is selected from the group consisting of hydrogen, and phenyl, 1-naphthyl, 2-naphthyl, anthracenyl and phenanthrenyl, which may optionally be substituted with one or more X, $R^{12}$ is selected from the group consisting of phenyl, 1-naphthyl, 2-naphthyl, anthracenyl, phenanthrenyl, and

[Formula 13]

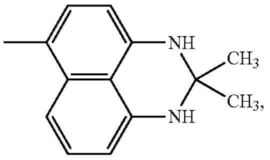

which may optionally be substituted with one or more X, W, isothiocyanate, or halosulfonyl, wherein V is —O-acryloyl, acetylamino, or phenyl, which may optionally be substituted with C1-7 alkyl, W is D- or L-alanylsulfonyl, D- or L-valylsulfonyl, D- or L-leucylsulfonyl, D- or L-methionylsulfonyl, D- or L-prolylsulfonyl, D- or L-tryptophylsulfonyl, D- or L-glycylsulfonyl, D- or L-cysteinylsulfonyl, D- or L-isoleucylsulfonyl, D- or L-phenylalanylsulfonyl, D- or L-tyrosylsulfonyl, D- or L-serylsulfonyl, D- or L-threonylsulfonyl, D- or L-asparaginylsulfonyl, D- or L-glutamylsulfonyl, D- or L-arginylsulfonyl, D- or L-histidylsulfonyl, D- or L-lysylsulfonyl, D- or L-asparagylsulfonyl, D- or L-glutaminylsulfonyl, —C(═O)—O-succinimidyl, acetyl, trifluoroacetyl, benzoylamino, —N═N-phenyl, phenylamino, or diaminophenylazophenyl, which may optionally be substituted with one or more amino, C1-7 alkyl, or aminoalkyl, or phenylazo, which may optionally be substituted with one or more X, naphthylazo

[Formula 14]

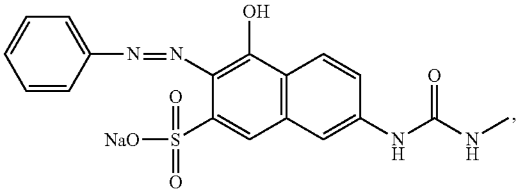

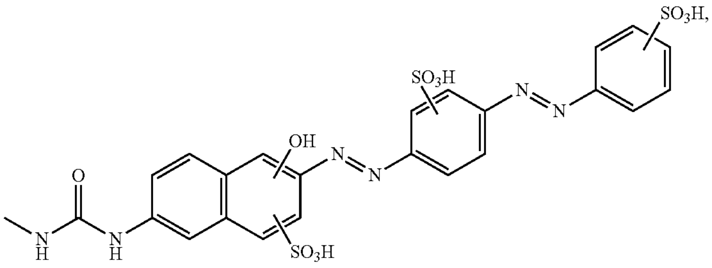

or

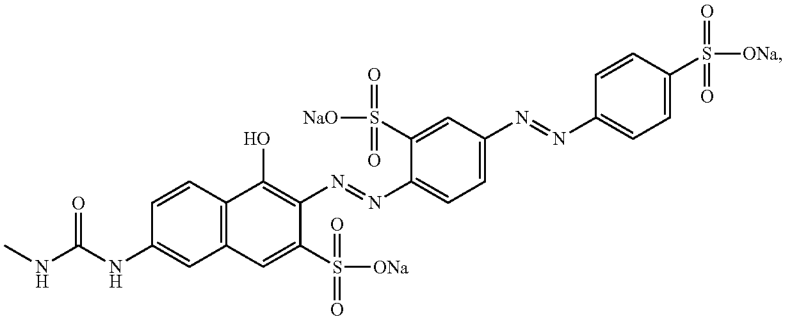

which may optionally be substituted with one or more Y, acetylamino,

X is linear or branched $C_{1-7}$ alkyl, $C_{1-7}$ alkenyl, $C_{1-7}$ alkynyl, $C_{1-7}$ alkoxy, halo, hydroxy, nitro, carboxy, cyano, sulfo, amino or alkylamino, which may optionally be substituted with one or more substituents selected from the group consisting of halo, amino, cyano, carboxy, carbonyl, alkoxy, alkylamino, nitroso, nitro and sulfo, Y is selected from the group consisting of halo, amino, cyano, carboxy, carbonyl, hydroxy, alkoxy and sulfo, and Z is $—SO_2—CH═CH_2$, $—SO_2—C_2H_4—O—SO_3H$, or 4,6-dichlorotriazin-2-ylamino.

In one embodiment, the phenylenediamine type compound of the present invention may be a compound having a structure of the following general formula Ia or IIa, or a salt, an anhydride or a solvate thereof:

[Formula 15]

(Ia))

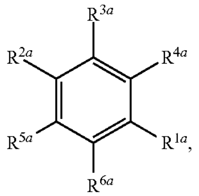

or

-continued (IIa)

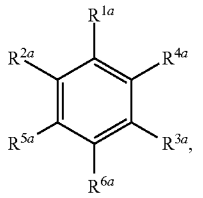

wherein $R^{1a}$ is —$NR^{7a}R^{8a}$, —N═N—$R^{9a}$, or —$N^+$═N, $R^{2a}$ is —$NR^{10a}R^{11a}$, or —N═N—$R^{12a}$, $R^{7a}$ and $R^{8a}$ are each independently hydrogen, or linear or branched $C_{1-6}$ alkyl, $C_{1-6}$ alkenyl, $C_{1-6}$ alkynyl, $C_{3-9}$ cycloalkyl, phenyl, 1-naphthyl, 2-naphthyl, anthracenyl, or phenanthrenyl, which may optionally be substituted with one or more Xa, $R^{10}$ is hydrogen, or linear or branched $C_{1-6}$ alkyl, $C_{1-6}$ alkenyl, $C_{1-6}$ alkynyl, $C_{3-9}$ cycloalkyl, phenyl, 1-naphthyl, 2-naphthyl, anthracenyl or phenanthrenyl, which may optionally be substituted with one or more Xa, $R^{3a}$, $R^{4a}$, $R^{5a}$ and $R^{6a}$ are each independently hydrogen, or linear or branched $C_{1-6}$ alkyl, $C_{1-6}$ alkenyl, $C_{1-6}$ alkynyl, $C_{1-6}$ alkoxy, halo, nitro, cyano, carboxy, sulfo, hydroxy or amino, which may optionally be substituted with one or more Y, or $R^{3a}$ and $R^{4a}$, or $R^{5a}$ and $R^{6a}$ form a benzene ring, or

[Formula 16]

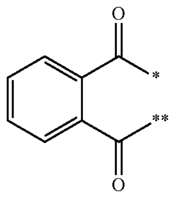

wherein * is bonded to the carbon atom bonded to $R^{3a}$, and ** is bonded to the carbon atom bonded to $R^{4a}$, or * is bonded to the carbon atom bonded to $R^{5a}$, and ** is bonded to the carbon atom bonded to $R^{6a}$, $R^{11a}$ is selected from the group consisting of phenyl, 1-naphthyl, 2-naphthyl, anthracenyl and phenanthrenyl, which may optionally be substituted with one or more Xa, $R^{9a}$ and $R^{12a}$ are each independently selected from the group consisting of hydrogen, and phenyl, 1-naphthyl, 2-naphthyl, anthracenyl and phenanthrenyl, which may optionally be substituted with one or more Xa, Xa is linear or branched $C_{1-6}$ alkyl, $C_{1-6}$ alkenyl, $C_{1-6}$ alkynyl, $C_{1-6}$ alkoxy, halo, hydroxy, nitro, carboxy, cyano, sulfo, amino or alkylamino, which may optionally be substituted with one or more substituents selected from the group consisting of halo, amino, cyano, carboxy, carbonyl, hydroxy, alkoxy, alkylamino, nitroso, nitro and sulfo, and Y is selected from the group consisting of halo, amino, cyano, carboxy, carbonyl, alkoxy and sulfo.

In one embodiment, the phenylenediamine type compound of the present invention may be a compound having a structure of the following general formula Ib or IIb, or a salt, an anhydride or a solvate thereof.

[Formula 17]

(Ib)

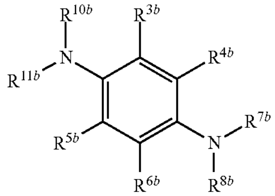

or (IIb)

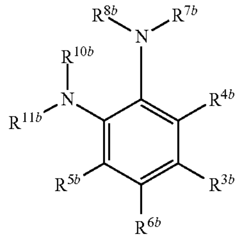

wherein $R^{7b}$, $R^{8b}$ and $R^{10b}$ are each independently hydrogen, or linear or branched $C_{1-6}$ alkyl, $C_{1-6}$ alkenyl, $C_{1-6}$ alkynyl, $C_{3-9}$ cycloalkyl, phenyl, 1-naphthyl, 2-naphthyl, anthracenyl or phenanthrenyl, which may optionally be substituted with one or more Xb, $R^{3b}$, $R^{4b}$, $R^{5b}$ and $R^{6b}$ are each independently hydrogen, or linear or branched $C_{1-6}$ alkyl, $C_{1-6}$ alkenyl, $C_{1-6}$ alkynyl, $C_{1-6}$ alkoxy, halo, nitro, cyano, carboxy, sulfo or amino, which may optionally be substituted with one or more Y, $R^{11b}$ is selected from the group consisting of phenyl, 1-naphthyl, 2-naphthyl, anthracenyl and phenanthrenyl, which may optionally be substituted with one or more Xb, wherein Xb is linear or branched $C_{1-6}$ alkyl, $C_{1-6}$ alkenyl, $C_{1-6}$ alkynyl, $C_{1-6}$ alkoxy, halo, hydroxy, nitro, carboxy, cyano, sulfo or amino, which may optionally be substituted with one or more substituents selected from the group consisting of halo, amino, cyano, carboxy, carbonyl, alkoxy and sulfo, and Y is selected from the group consisting of halo, amino, cyano, carboxy, carbonyl, alkoxy and sulfo.

In the present specification, the alkyl refers to a linear or branched hydrocarbon having, for example, 1 to 7 carbon atoms, for example, 1 to 6 carbon atoms. Examples of the alkyl include, but are not limited to, methyl, ethyl, propyl, isopropyl, isobutyl, n-butyl, tert-butyl, isopentyl, n-pentyl, and heptyl.

The number of atoms (e.g., carbon atoms) used in the present specification is indicated by, for example, "Cx-Cy alkyl", which refers to an alkyl group having x to y carbon atoms. Other substituents and ranges are indicated similarly.

The term alkenyl used in the present specification refers to a linear or branched aliphatic hydrocarbon having one or more carbon-carbon double bonds. Examples thereof include, but are not limited to, vinyl and allyl.

The term alkynyl used in the present specification refers to a linear or branched aliphatic hydrocarbon having one or more carbon-carbon triple bonds. Examples thereof include, but are not limited to, ethynyl.

The term cycloalkyl used in the present specification refers to a substituted or unsubstituted nonaromatic cyclic hydrocarbon ring. Examples of the cycloalkyl group include, but are not limited to, cyclopropyl, cyclobutyl, cyclopentyl, cyclohexyl, and cycloheptyl.

The term halo used in the present specification refers to a chemical group from the group 17 elements, for example, —Cl, —Br, or —I. The term halogen used in the present specification refers to fluorine, chlorine, bromine, or iodine.

The term haloalkyl used in the present specification refers to an alkyl group substituted with at least one halogen. Examples of a haloalkyl group include, but are not limited to, methyl, ethyl, propyl, isopropyl, n-butyl, and t-butyl each independently substituted with one or more halogen, for example, fluoro, chloro, bromo, or iodo.

The term halosulfonyl used in the present specification refers to a sulfonyl group substituted with at least one halogen. Examples thereof include, but are not limited to, chlorosulfonyl ($Cl—SO_2—$) and bromosulfonyl ($Br—SO_2—$).

The term phenyl used in the present specification refers to a substituted or unsubstituted benzene ring system. The term naphthyl used in the present specification refers to a substituted or unsubstituted naphthalene ring system and examples thereof include 1-naphthyl and 2-naphthyl. The term anthracenyl used in the present specification refers to a substituted or unsubstituted anthracene ring system. The term phenanthrenyl used in the present specification refers to a substituted or unsubstituted phenanthrene ring system.

In the present specification, the term acetyl refers to $CH_3CO—$. In the present specification, the term trifluoroacetyl refers to $CF_3CO—$. The term carboxy used in the present specification refers to —COOH. In the present specification, the term furanyl refers to a monovalent group of furan, for example, 2-furanyl or 3-furanyl. In the present specification, the term formyl, also referred to as aldehyde, refers to —COH. In the present specification, the term furanylformyl refers to a formyl group bonded to a furanyl group (furanyl-CO—). In the present specification, the term pyrazolyl refers to a pyrazole ring system. In the present specification, the term pyrazolylformyl refers to a formyl group bonded to a pyrazolyl group (pyrazolyl-CO—). The term fluorenyl used in the present specification refers to a substituted or unsubstituted fluorene ring system.

In the present specification, $—N^+═N$, is also referred to as azide, and can also be indicated by a $—N_2$ group. In the present specification, the term benzyl refers to $C_6H_5CH_2—$. In the present specification, the term benzoyl refers to $C_6H_5—C(═O)—$. In the present specification, the term azo is also indicated by R'—N═N—R", wherein R' and R" may be the same or different. For example, naphthylazo refers to naphthyl-N═N—.

In the present specification, the term nitro refers to a $—NO_2$ group. In the present specification, the term nitroso refers to a —N═O group. In the present specification, the term cyano refers to a —CN group. In the present specification, the term sulfo refers to $—SO_3H$. In the present specification, the term hydroxy refers to —OH. In the present specification, the term oxo refers to ═O.

In the present specification, the term amino refers to a —NR'R" group, wherein R' and R" may be the same or different. Each of R' and R" may, for example, be H, alkyl, alkenyl, alkynyl, cycloalkyl, phenyl, naphthyl, anthracenyl, or phenanthrenyl, although not limited thereto. In the present specification, the aminoalkyl comprises an alkylene linker linked to an amino group. Examples of aminoalkyl include, but are not limited to, $—(CH_2)_nNH_2$. In the present specification, the term alkylamino refers to amino linked to an alkyl group. Examples of alkylamino include, but are not limited to, $C_{1-7}$ alkyl-NH—. In the present specification, the term acetylamino refers to amino linked to an acetyl group. Examples of acetylamino include, but are not limited to, acetyl-NH—.

In the present specification, the term acryloyl refers to $H_2C═CH—C(═O)—$. In the present specification, the term —O-acryloyl refers to $H_2C═CH—C(═O)—O—$. In the present specification, the term isothiocyanate refers to —N═C═S. In the present specification, the term succinimidyl refers to $(CH_2CO)_2N—$. In the present specification, the term carbonyl refers to —C(═O)—. In the present specification, the term alkoxy refers to an —O— alkyl group.

In the present specification, the phrase "which may optionally be substituted" or "substituted or unsubstituted" means an arbitrary substitution with one or more substituents and also includes a plurality of (degrees of) substitutions.

In one embodiment, the phenylenediamine type compound of the present invention may be N-isopropyl-N'-phenyl-p-phenylenediamine (IPPD):

[Formula 18]

(CAS No. 101-72-4)

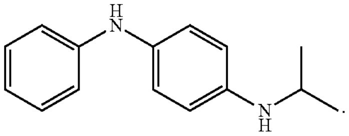

In one embodiment, the phenylenediamine type compound of the present invention may be N,N'-diphenyl-p-phenylenediamine (DPPD):

[Formula 19]

(Cas No. 74-31-7)

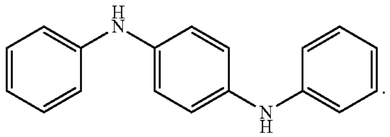

In one embodiment, the phenylenediamine type compound of the present invention may be N-(1,3-dimethylbutyl)-N'-phenyl-p-phenylenediamine (6PPD):

[Formula 20]

(CAS No. 793-24-8)

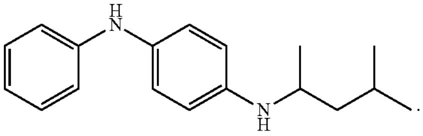

In one embodiment, the phenylenediamine type compound of the present invention may be Bindschedler's green leuco base (BGLB, CAS No. 637-31-0):

[Formula 21]

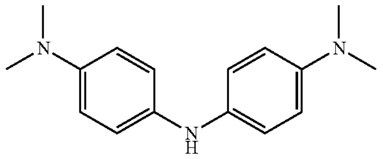

In one embodiment, the phenylenediamine type compound of the present invention may be Variamine Blue B Base (CAS No. 101-64-4):

[Formula 22]

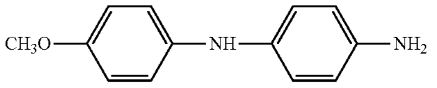

In one embodiment, the phenylenediamine type compound of the present invention may be 2-nitro-aminodiphenylamine (CAS No. 2784-89-6):

[Formula 23]

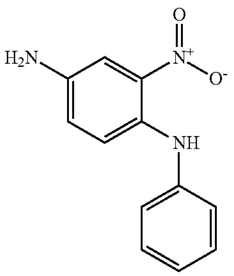

In one embodiment, the phenylenediamine type compound of the present invention may be N-methyl-N'-phenyl-p-phenylenediamine:

[Formula 24]

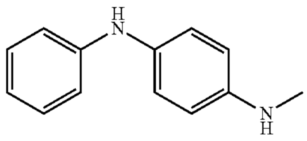

In one embodiment, the phenylenediamine type compound of the present invention may be N-ethyl-N'-phenyl-p-phenylenediamine:

[Formula 25]

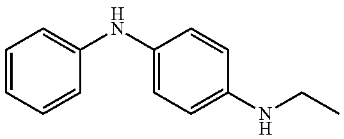

In one embodiment, the phenylenediamine type compound of the present invention may be N-isopropyl-N'-(4-aminophenyl)-p-phenylenediamine:

[Formula 26]

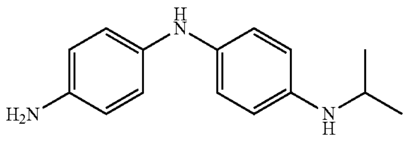

In one embodiment, the phenylenediamine type compound of the present invention may be tris[4-(diethylamino)phenyl]amine (TDPA, CAS No. 47743-70-4):

[Formula 27]

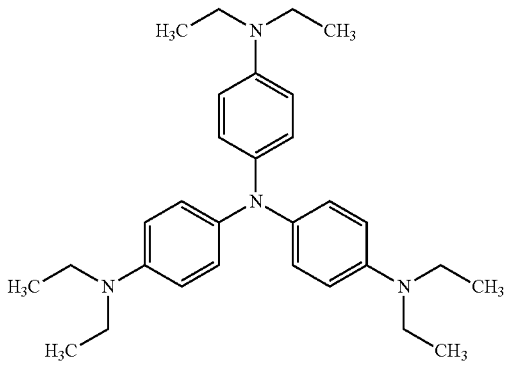

In one embodiment, the phenylenediamine type compound of the present invention may be 4-(dimethylamino)-4'-nitrosodiphenylamine (CAS No. 7696-70-0):

[Formula 28]

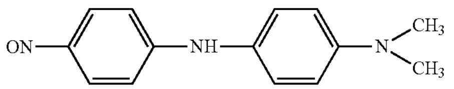

In one embodiment, the phenylenediamine type compound of the present invention may be N-phenyl-o-phenylenediamine (CAS No. 534-85-0):

[Formula 29]

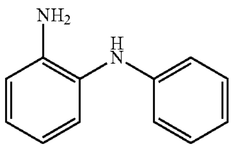

In one embodiment, the phenylenediamine type compound of the present invention may be N-(4-chlorophenyl)-1,2-phenylenediamine (CAS No. 68817-71-0):

[Formula 30]

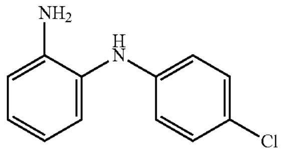

In one embodiment, the phenylenediamine type compound of the present invention may be 4-diazodiphenylamine sulfate (CAS No. 4477-28-5):

[Formula 31]

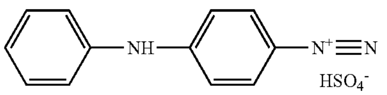

In one embodiment, the phenylenediamine type compound of the present invention may be Acid Yellow 36 (CAS No. 587-98-4):

[Formula 32]

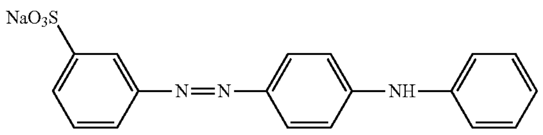

In one embodiment, the phenylenediamine type compound of the present invention may be 2-amino-4-isopropylamino-diphenylamine:

[Formula 33]

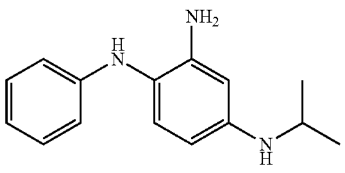

In one embodiment, the phenylenediamine type compound of the present invention may be N-isopropyl-N'-(4-hydroxyphenyl)-p-phenylenediamine:

[Formula 34]

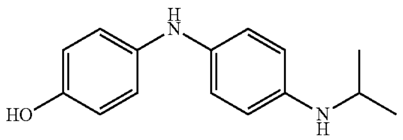

In one embodiment, the phenylenediamine type compound of the present invention may be N,N'-di-2-naphthyl-1,4-phenylenediamine (CAS No. 93-46-9):

[Formula 35]

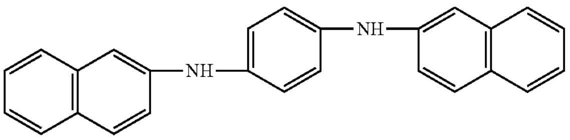

In one embodiment, the phenylenediamine type compound of the present invention ma be 4-(2-octylamino) diphenylamine (CAS No. 15233-47-3):

[Formula 36]

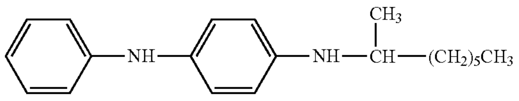

In one embodiment, the phenylenediamine type compound of the present invention may be N-(2-amino-4-chlorophenyl)anthranilic acid (CAS No. 67990-66-3):

[Formula 37]

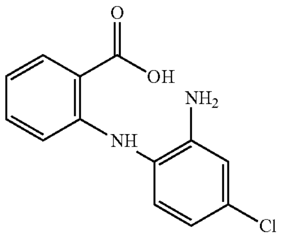

In one embodiment, the phenylenediamine type compound of the present invention may be 4-diazo-3-methoxy-diphenylamine sulfate (CAS No. 36305-05-2):

[Formula 38]

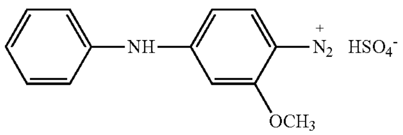

In one embodiment, the phenylenediamine type compound of the present invention may be 4-(phenylazo)diphenylamine (CAS No. 101-75-7):

[Formula 39]

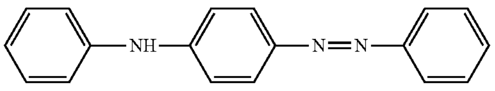

In one embodiment, the phenylenediamine type compound of the present invention may be Acid Orange 5 (CAS RN:554-73-4):

[Formula 40]

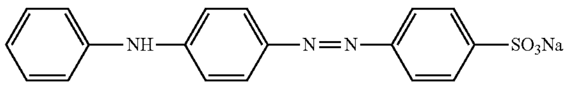

In one embodiment, the phenylenediamine type compound of the present invention may be Alizarin Cyanine Green F (CAS No. 4403-90-1):

[Formula 41]

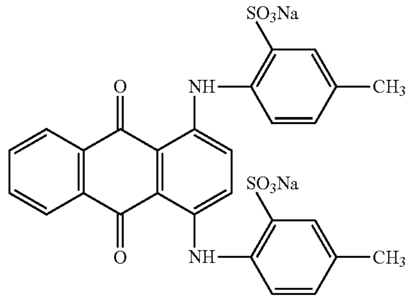

In one embodiment, the phenylenediamine type compound of the present invention may be Alizarin Astrol (CAS RN: 6408-51-1):

[Formula 42]

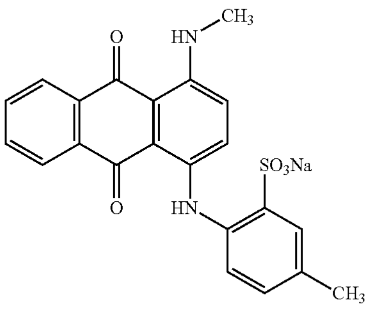

In one embodiment, the phenylenediamine type compound of the present invention may be Disperse Yellow 9 (CAS No. 6373-73-5):

[Formula 43]

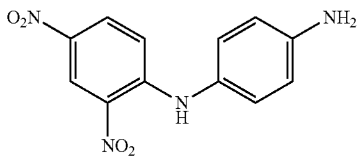

In one embodiment, the phenylenediamine type compound of the present invention may be 5-sulfo-4'-diethylamino-2,2'-dihydroxyazobenzene (CAS No. 1563-01-5):

[Formula 44]

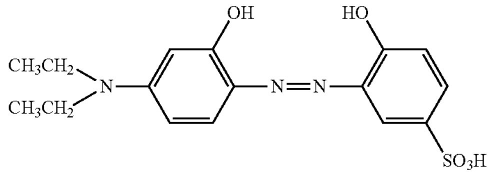

In one embodiment, the phenylenediamine type compound of the present invention may be Alizarin Cyanine Green F (CAS No. 4403-90-1):

[Formula 45]

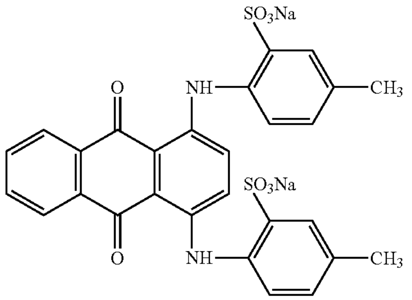

In one embodiment, the phenylenediamine type compound of the present invention may be Alphamine Red R Base (CAS No. 57322-42-6):

[Formula 46]

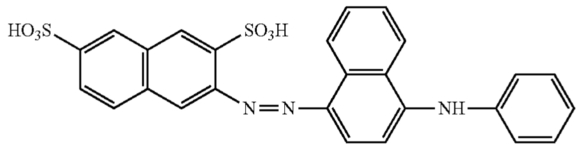

In one embodiment, the phenylenediamine type compound of the present invention may be Crocein scarlet 3B (CAS No. 5413-75-2):

[Formula 47]

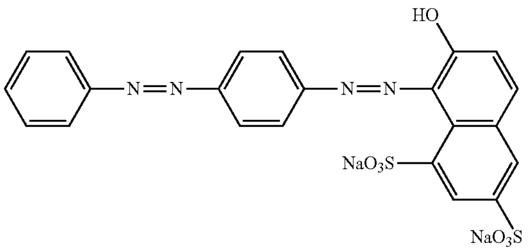

In one embodiment, the phenylenediamine type compound of the present invention may be p-phenylphenylenediamine (CAS No. 2198-59-6):

[Formula 48]
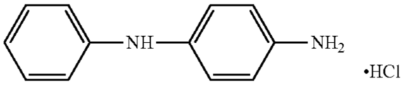
In one embodiment, the phenylenediamine type compound of the present invention may be any of compounds shown in the following tables.
TABLE 1-1
| No. | Structure | Compound name | CAS |
|---|---|---|---|
| 1 | 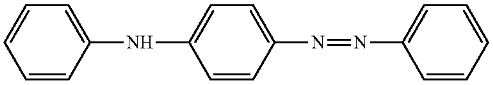 [SMILES: c1ccc(N=Nc2ccc(Nc3ccccc3)cc2)cc1] | 4-(Phenylazo)diphenylamine | 101-75-7 |
| 2 | 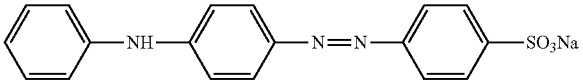 | Acid Orange 5 | 554-73-4 |
| 3 | 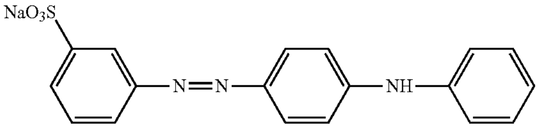 | Acid Yellow 36 | 587-98-4 |
| 4 | 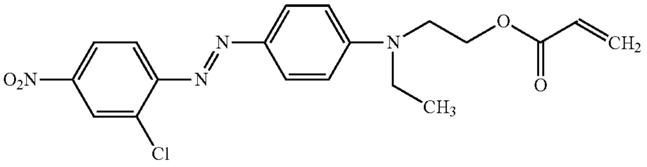 [SMILES: C=CC(=O)OCCN(CC)c1ccc(/N=N/c2ccc([N+](=O)[O-])cc2Cl)cc1] | Disperse Red 13 acrylate | 10462-94-9 |
| 5 | 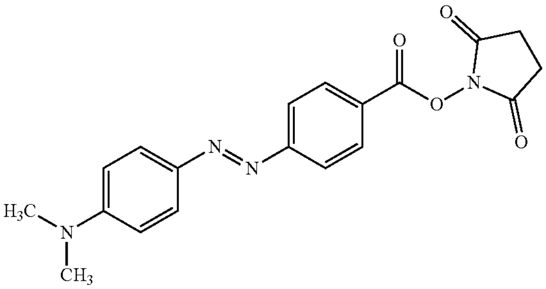 [SMILES: CN(C)c1ccc(/N=N/c2ccc(C(=O)ON3C(=O)CCC3=O)cc2)cc1] | 4-[4-(Dimethylamino) phenylazo]benzoic acid N-succinimidyl ester | 146998-31-4 |
| 6 | 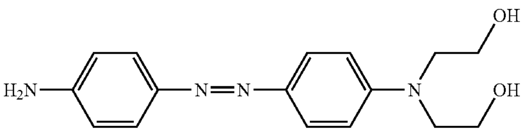 [SMILES: Nc1ccc(N=Nc2ccc(N(CCO)CCO)cc2)cc1] | Disperse Black 9 | 20721-50-0 |
| 7 | 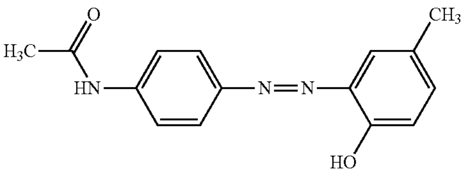 [SMILES: CC(=O)Nc1ccc(N=Nc2cc(C)ccc2O)cc1] | Disperse Yellow 3 | 2832-40-8 |

TABLE 1-1-continued
| No. | Structure | Compound name | CAS |
| --- | --- | --- | --- |
| 8 | 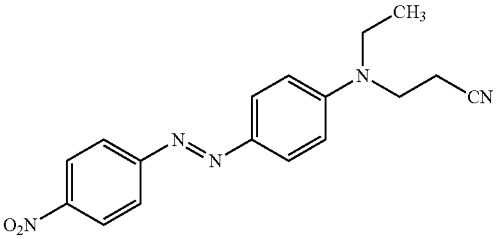 [SMILES: CCN(CCC#N)c1ccc(/N=N/c2ccc([N+](=O)[O-])cc2)cc1] | Disperse Orange 25 | 31482-56-1 |
| 9 | 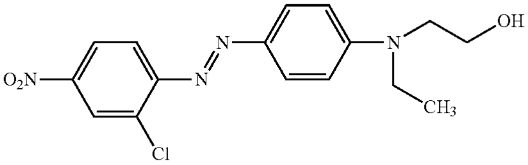 [SMILES: CCN(CCO)c1ccc(/N=N/c2ccc([N+](=O)[O-])cc2Cl)cc1] | Disperse Red 13 | 3180-81-2 |
| 10 | 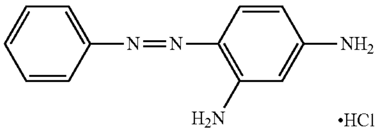 | Chrysoidine G | 532-82-1 |
| 11 | 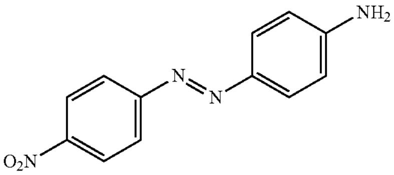 [SMILES: Nc1ccc(/N=N/c2ccc([N+](=O)[O-])cc2)cc1] | Disperse Orange 3 | 730-40-5 |
| 12 | 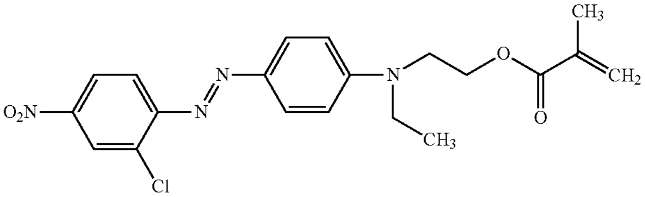 [SMILES: C=C(C)C(=O)OCCN(CC)c1ccc(/N=N/c2ccc([N+](=O)[O-])cc2Cl)cc1] | Disperse Red 13 methacrylate | 82701-58-4 |
| 13 | 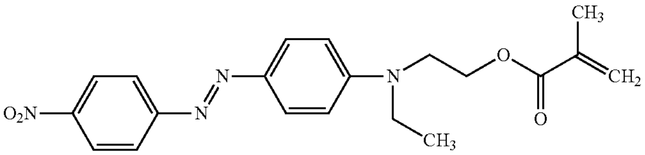 [SMILES: C=C(C)C(=O)OCCN(CC)c1ccc(/N=N/c2ccc([N+](=O)[O-])cc2)cc1] | Disperse Red 1 methacrylate | 103553-48-6 |
| 14 | 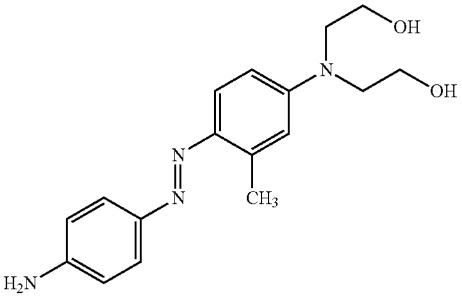 [SMILES: Cc1cc(N(CCO)CCO)ccc1/N=N/c1ccc(N)cc1] | HC Yellow 7 | 104226-21-3 |

TABLE 1-1-continued
| No. | Structure | Compound name | CAS |
|---|---|---|---|
| 15 | 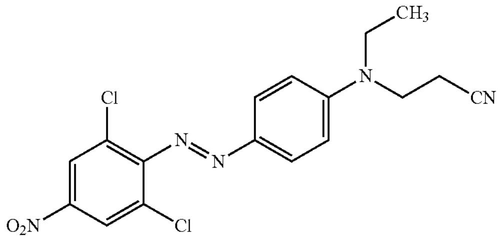 [SMILES: CCN(CCC#N)c1ccc(/N=N/c2c(Cl)cc([N+](=O)[O-])cc2Cl)cc1] | Disperse Orange 37 | 13301-61-6 |
| 16 | 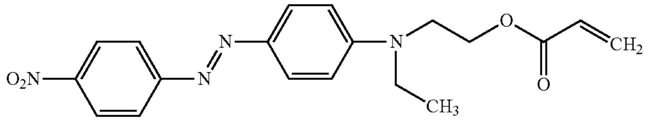 [SMILES: C=CC(=O)OCCN(CC)c1ccc(/N=N/c2ccc([N+](=O)[O-])cc2)cc1] | Disperse Red 1 acrylate | 13695-46-0 |
| 17 | 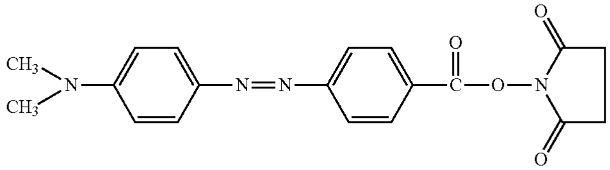 [SMILES: CN(C)c1ccc(N=Nc2ccc(C(=O)ON3C(=O)CCC3=O)cc2)cc1] | N-Succinimidyl 4-[4-(Dimethylamino) phenylazo]benzoate | 146998-31-4 |
| 18 | 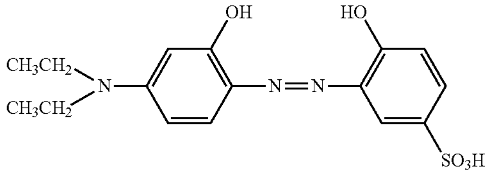 | 5-Sulfo-4'-diethylamino-2,2'-dihydroxyazobenzene | 1563-01-5 |
| 19 | 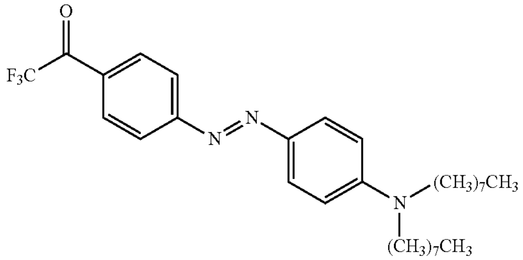 | 4-(Dioctylamino)-4'-(trifluoroacetyl)azobenzene | 193154-07-3 |
| 20 | 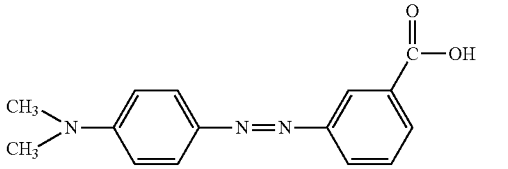 [SMILES: CN(C)c1ccc(N=Nc2cccc(C(=O)O)c2)cc1] | m-Methyl Red | 20691-84-3 |
| 21 | 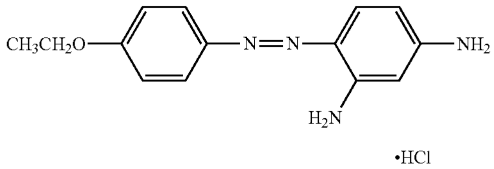 | 4-Ethoxychrysoidine Hydrochloride | 2313-87-3 |
| 22 | 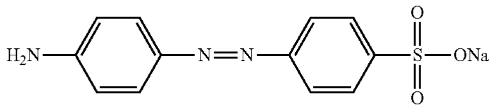 | Sodium 4-Aminoazobenzene-4'-sulfonate | 2491-71-6 |
| 23 | 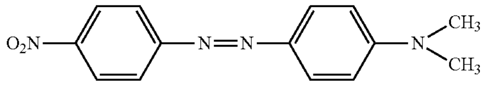 [SMILES: CN(C)c1ccc(N=Nc2ccc([N+](=O)[O-])cc2)cc1] | 4'-Nitro-4-dimethylaminoazobenzene | 2491-74-9 |

TABLE 1-1-continued
| No. | Structure | Compound name | CAS |
|---|---|---|---|
| 24 | 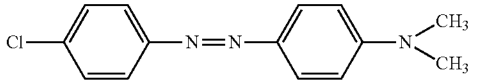 [SMILES: CN(C)c1ccc(N=Nc2ccc(Cl)cc2)cc1] | 4'-Chloro-4-dimethylaminoazobenzene | 2491-76-1 |
| 25 | 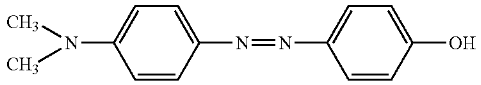 [SMILES: CN(C)c1ccc(N=Nc2ccc(O)cc2)cc1] | 4-Hydroxy-4'-dimethylaminoazobenzene | 2496-15-3 |
| 26 | 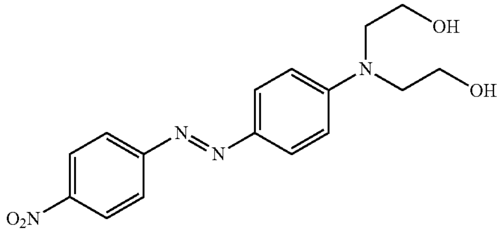 [SMILES: O=[N+]([O-])c1ccc(/N=N/c2ccc(N(CCO)CCO)cc2)cc1] | Disperse Red 19 | 2734-52-3 |
| 27 | 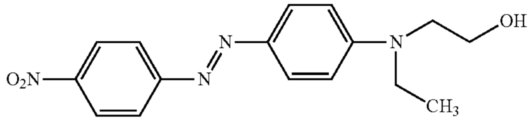 [SMILES: CCN(CCO)c1ccc(/N=N/c2ccc([N+](=O)[O-])cc2)cc1] | Disperse Red 1 | 2872-52-8 |
| 28 | 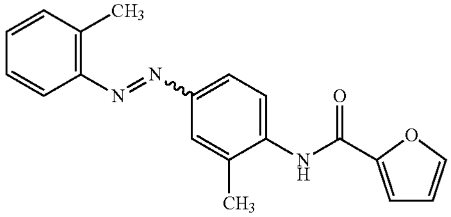 [SMILES: Cc1ccccc1N=Nc1ccc(NC(=O)c2ccco2)c(C)c1] | N-[2-Methyl-4-[2-(2-methylphenyl)diazenyl] phenyl]-2-furancarboxamide | 289494-16-2 |
| 29 | 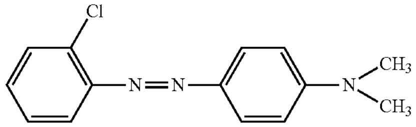 | 2'-Chloro-4-dimethylaminoazobenzene | 3010-47-7 |
| 30 | 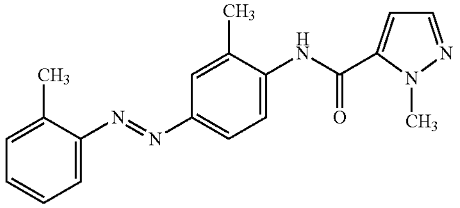 [SMILES: Cc1ccccc1/N=N/c1ccc(NC(=O)c2ccnn2C)c(C)c1] | CH-223191 | 301326-22-7 |
| 31 | 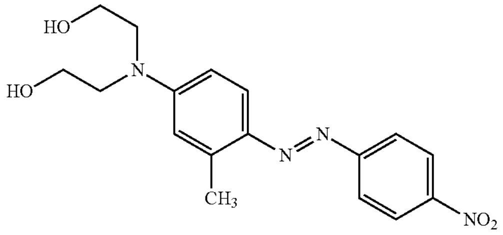 [SMILES: Cc1cc(N(CCO)CCO)ccc1/N=N/c1ccc([N+](=O)[O-])cc1] | Disperse Red 17 | 3179-89-3 |
| 32 | 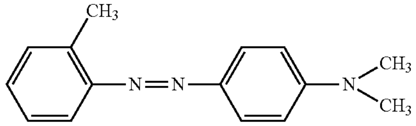 [SMILES: Cc1ccccc1N=Nc1ccc(N(C)C)cc1] | 4-(Dimethylamino)-2'-methylazobenzene | 3731-39-3 |

TABLE 1-1-continued

| No. | Structure | Compound name | CAS |
|---|---|---|---|
| 33 | 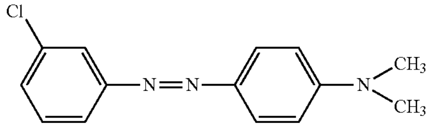 [SMILES: CN(C)c1ccc(N=Nc2cccc(Cl)c2)cc1] | 3'-Chloro-4-dimethylaminoazobenzene | 3789-77-3 |
| 34 | 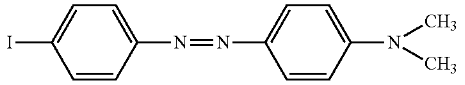 | 4'-Iodo-4-dimethylaminoazobenzene | 3805-67-2 |
| 35 | 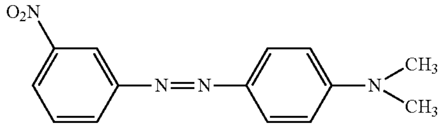 [SMILES: CN(C)c1ccc(N=Nc2cccc([N+](=O)[O-])c2)cc1] | 3'-Nitro-4-dimethylaminoazobenzene | 3837-55-6 |
| 36 | 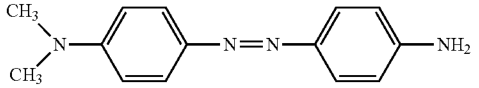 | 4-Amino-4'-dimethylaminoazobenzene | 539-17-3 |
| 37 | 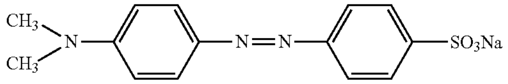 | Methyl Orange | 547-58-0 |
| 38 | 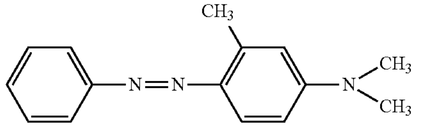 [SMILES: Cc1cc(N(C)C)ccc1N=Nc1ccccc1] | 4-(Dimethylamino)-2-methylazobenzene | 54-88-6 |
| 39 | 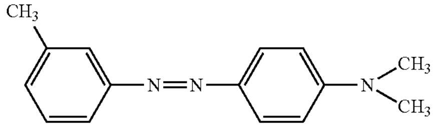 [SMILES: Cc1cccc(N=Nc2ccc(N(C)C)cc2)c1] | 4-(Dimethylamino)-3'-methylazobenzene | 55-80-1 |
| 40 | 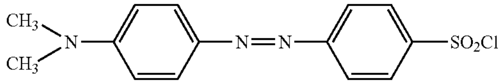 [SMILES: CN(C)c1ccc(N=Nc2ccc(S(=O)(=O)Cl)cc2)cc1] | Dabsyl Chloride | 56512-49-3 |
| 41 | 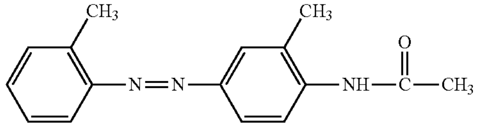 [SMILES: CC(=O)Nc1ccc(N=Nc2ccccc2C)cc1C] | 4-Acetamido-2',3-dimethylazobenzene | 588-23-8 |
| 42 | 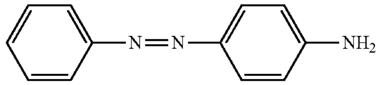 [SMILES: Nc1ccc(N=Nc2ccccc2)cc1] | 4-Aminoazobenzene | 60-09-3 |
| 43 | 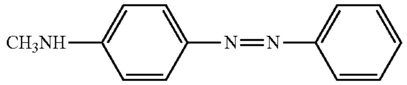 | 4-(Methylamino)azobenzene | 621-90-9 |
| 44 | 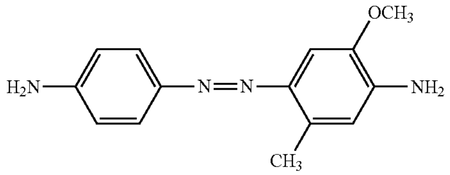 [SMILES: COc1cc(N=Nc2ccc(N)cc2)c(C)cc1N] | Disperse Diazo Black 3BF | 6232-57-1 |
| 45 | 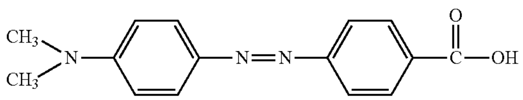 [SMILES: CN(C)c1ccc(N=Nc2ccc(C(=O)O)cc2)cc1] | 4-Dimethylaminoazobenzene-4'-carboxylic Acid | 6268-49-1 |

TABLE 1-1-continued
| No. | Structure | Compound name | CAS |
|---|---|---|---|
| 46 | 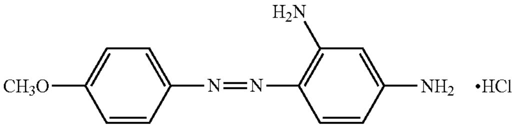 | Methoxy Red | 68936-13-0 |
| 47 | 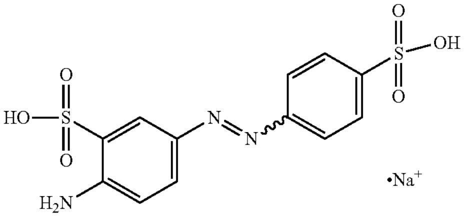 [SMILES: Nc1ccc(N=Nc2ccc(S(=O)(=O)O)cc2)cc1S(=O)(=O)O ; [Na+]] | 4-Amino-1,1-azobenzene-3,4'-disulfonic acid monosodium salt | 74543-21-8 |
| 48 | 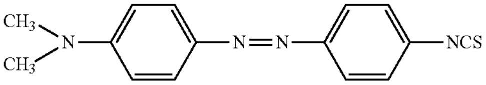 | 4-(Dimethylamino) azobenzene 4'-Isothiocyanate | 7612-98-8 |
| 49 | 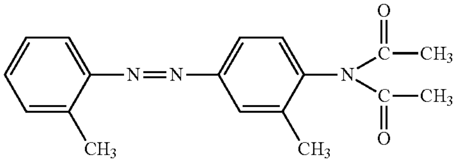 [SMILES: CC(=O)N(C(C)=O)c1ccc(N=Nc2ccccc2C)cc1C] | N,N-Diacetyl-o-aminoazotoluene | 83-63-6 |
| 50 | 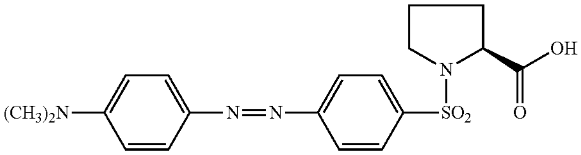 | Dabsyl-L-proline | 89131-09-9 |
| 51 | 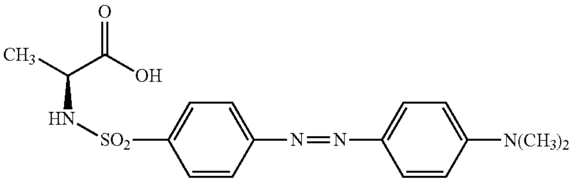 [SMILES: C[C@H](NS(=O)(=O)c1ccc(N=Nc2ccc(N(C)C)cc2)cc1)C(=O)O] | Dabsyl-L-alanine | 89131-10-2 |
| 52 | 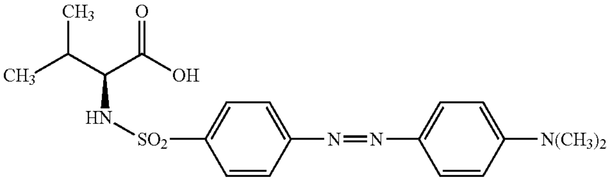 [SMILES: CC(C)[C@H](NS(=O)(=O)c1ccc(N=Nc2ccc(N(C)C)cc2)cc1)C(=O)O] | Dabsyl-L-valine | 89131-11-3 |
| 53 | 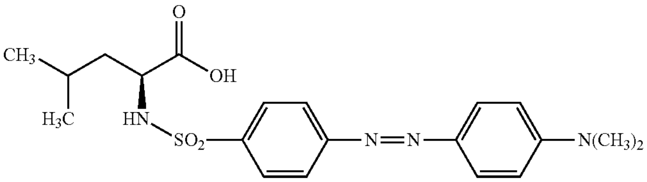 [SMILES: CC(C)C[C@H](NS(=O)(=O)c1ccc(N=Nc2ccc(N(C)C)cc2)cc1)C(=O)O] | Dabsyl-L-leucine | 89131-12-4 |
| 54 | 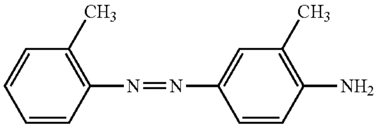 [SMILES: Cc1cc(N=Nc2ccccc2C)ccc1N] | 2-Aminoazotoluene | 97-56-3 |

TABLE 1-1-continued
| No. | Structure | Compound name | CAS |
|---|---|---|---|
| 55 | 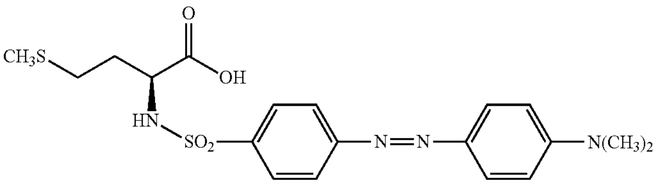 | Dabsyl-L-methionine | 97684-99-6 |
| 56 | 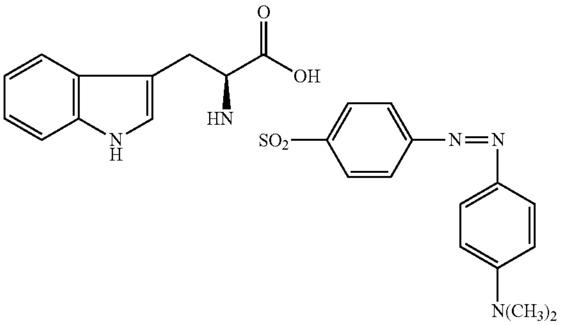 | Dabsyl-L-tryptophan | 97685-00-2 |
| 57 | 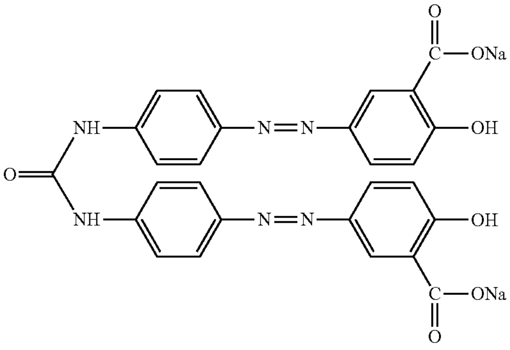 | Direct Yellow 26 | 2829-42-7 |
| 58 | 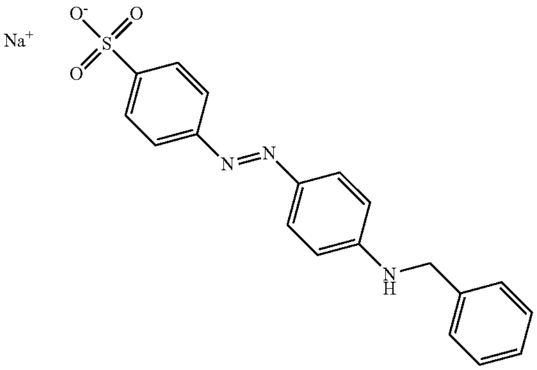 [SMILES: [Na+] ; O=S(=O)([O-])c1ccc(/N=N/c2ccc(NCc3ccccc3)cc2)cc1] | Benzyl Orange | 36402-77-4 |
| 59 | 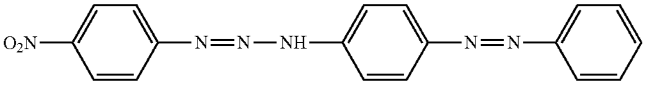 [SMILES: O=[N+]([O-])c1ccc(N=NNc2ccc(N=Nc3ccccc3)cc2)cc1] | Cadion | 5392-67-6 |

TABLE 1-1-continued
| No. | Structure | Compound name | CAS |
| --- | --- | --- | --- |
| 60 | 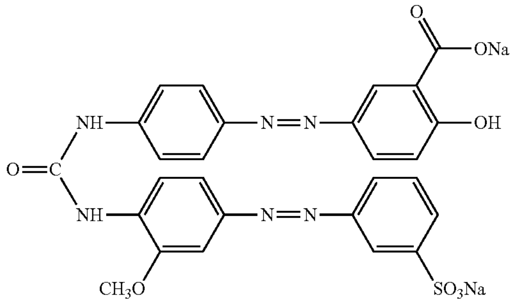 | Direct Yellow 44 | 8005-52-5 |
| 61 | 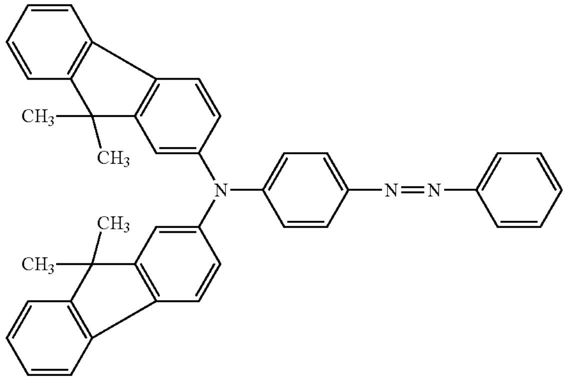 [SMILES: CC1(C)c2ccccc2-c2ccc(N(c3ccc(N=Nc4ccccc4)cc3)c3ccc4c(c3)C(C)(C)c3ccccc3-4)cc21] | 4-[Bis(9,9-dimethylfluoren-2-yl)amino]azobenzene | 883554-70-9 |
| 62 | 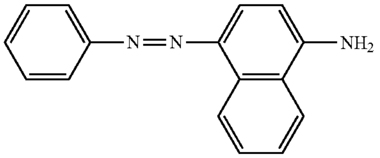 [SMILES: Nc1ccc(N=Nc2ccccc2)c2ccccc12] | 4-Phenylazo-1-naphthylamine | 131-22-6 |
| 63 | 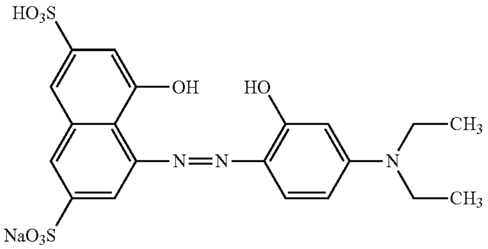 | Beryllon III | 3627-04-1 |
| 64 | 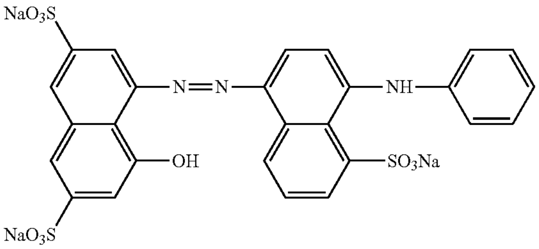 | Acid Blue 92 | 3861-73-2 |
| 65 | 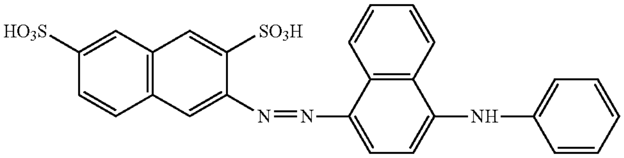 [SMILES: O=S(=O)(O)c1ccc2cc(N=Nc3ccc(Nc4ccccc4)c4ccccc34)c(S(=O)(=O)O)cc2c1] | Alphamine Red R Base | 57322-42-6 |

TABLE 1-1-continued
| No. | Structure | Compound name | CAS |
|---|---|---|---|
| 66 | 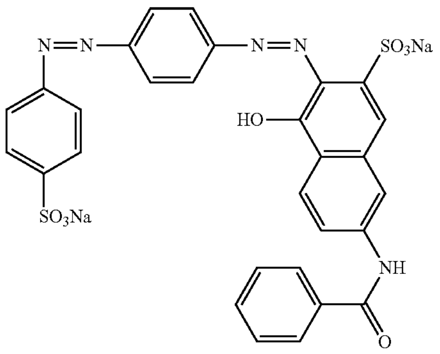 | Chlorantine Fast Red 5B | 259636 |
| 67 | 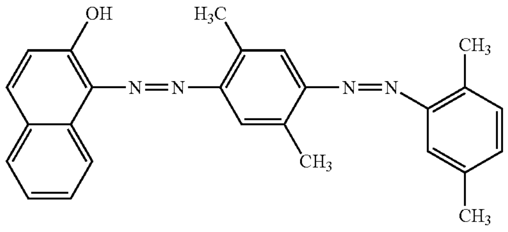 [SMILES: Cc1ccc(C)c(N=Nc2cc(C)c(N=Nc3c(O)ccc4ccccc34)cc2C)c1] | Oil Red O | 1320-06-5 |
| 68 | 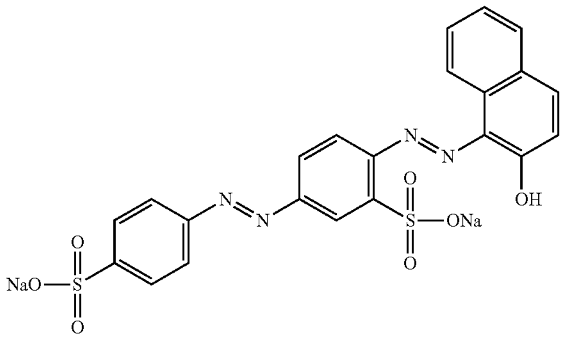 | Ponceau BS | 4196-99-0 |
| 69 | 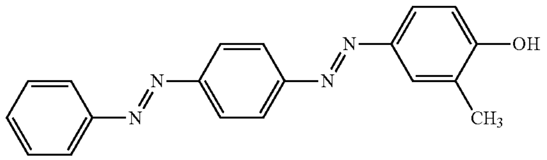 [SMILES: Cc1cc(/N=N/c2ccc(/N=N/c3ccccc3)cc2)ccc1O] | Disperse Yellow 7 | 6300-37-4 |
| 70 | 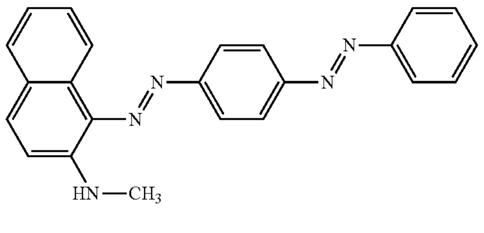 [SMILES: CNc1ccc2ccccc2c1/N=N/c1ccc(/N=N/c2ccccc2)cc1] | Lipid Crimson | 125455-63-2 |

TABLE 1-1-continued
| No. | Structure | Compound name | CAS |
|---|---|---|---|
| 71 | 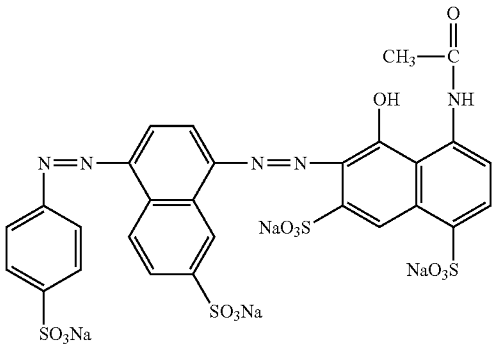 | Black PN | 2519-30-4 |
| 72 | 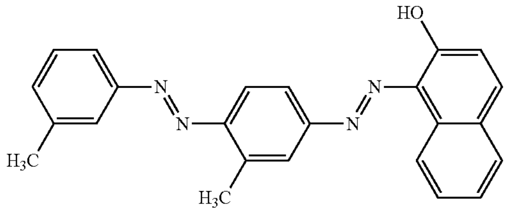 [SMILES: Cc1cccc(/N=N/c2ccc(/N=N/c3c(O)ccc4ccccc34)cc2C)c1] | Sudan Red B | 3176-79-2 |
| 73 | 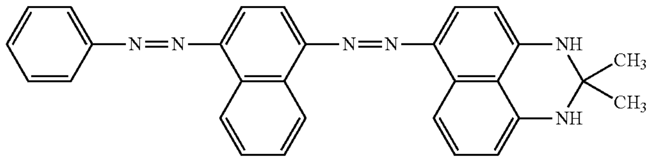 [SMILES: CC1(C)Nc2cccc3c(N=Nc4ccc(N=Nc5ccccc5)c5ccccc45)ccc(c23)N1] | Sudan Black B | 4197-25-5 |
| 74 | 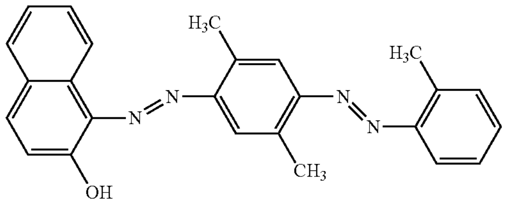 [SMILES: Cc1ccccc1/N=N/c1cc(C)c(/N=N/c2c(O)ccc3ccccc23)cc1C] | Oil Red EGN | 4477-79-6 |
| 75 | 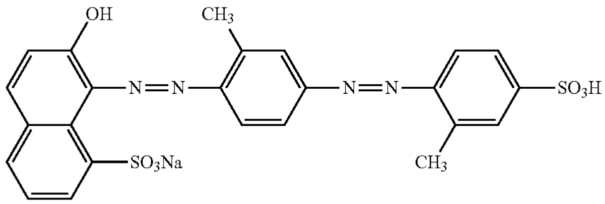 (2Na) | Crocein Scarlet 7B | 6226-76-2 |
| 76 | 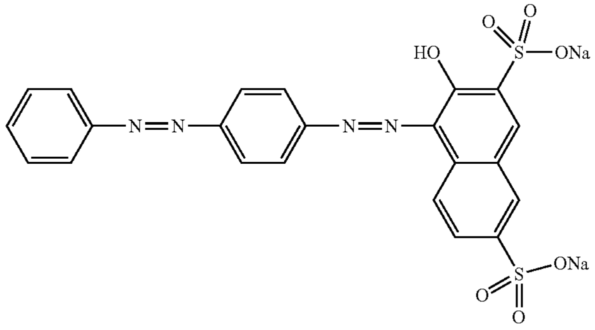 | Ponceau SS | 6226-78-4 |

TABLE 1-1-continued
| No. | Structure | Compound name | CAS |
| --- | --- | --- | --- |
| 77 | 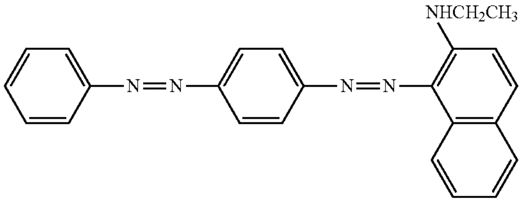 | Oil Violet | 6368-72-5 |
| 78 | 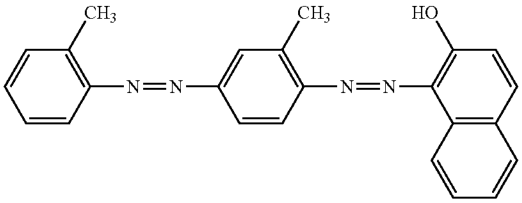 [SMILES: Cc1ccccc1N=Nc1ccc(N=Nc2c(O)ccc3ccccc23)c(C)c1] | Sudan IV | 85-83-6 |
| 79 | 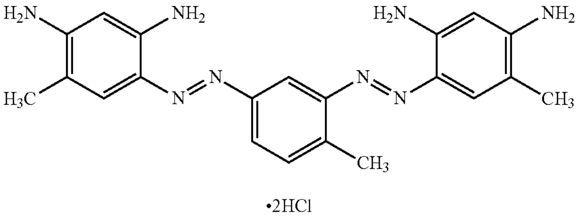 [SMILES: Cc1cc(/N=N/c2ccc(C)c(/N=N/c3cc(C)c(N)cc3N)c2)c(N)cc1N] | Bismarck Brown R | 5421-66-9 |
| 80 | 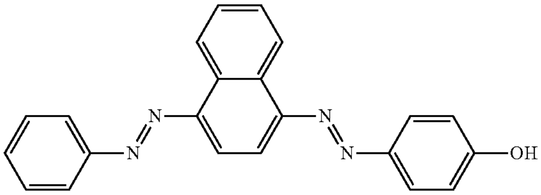 [SMILES: Oc1ccc(/N=N/c2ccc(/N=N/c3ccccc3)c3ccccc23)cc1] | Disperse Orange 13 | 1590182 |
| 81 | 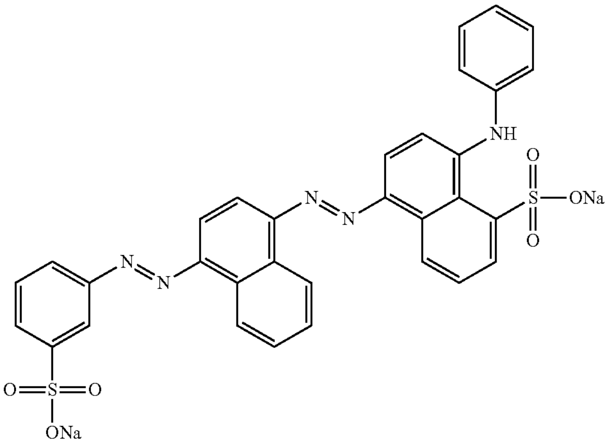 | Acid Blue 113 | 3351-05-1 |
| 82 | 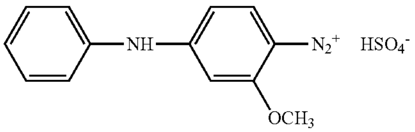 | 4-Diazo-3-methoxydiphenylamine Sulfate | 36305-05-2 |
| 83 | 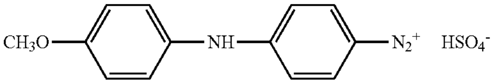 | 4-Diazo-4'-methoxydiphenylamine Sulfate | 49732-38-9 |

TABLE 1-1-continued
| No. | Structure | Compound name | CAS |
|---|---|---|---|
| 84 | 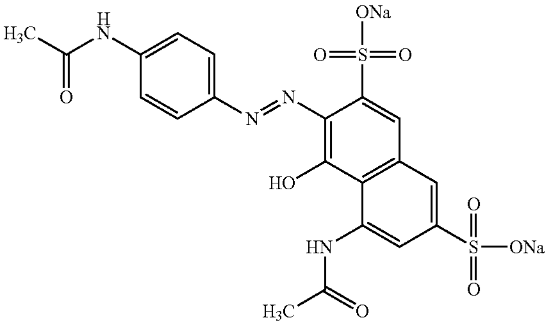 | Acid Violet 7 | 4321-69-1 |
| 85 | 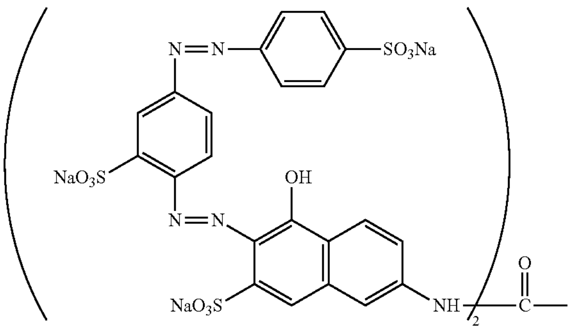 | Direct Red 80 | 2610-10-8 |
| 86 | 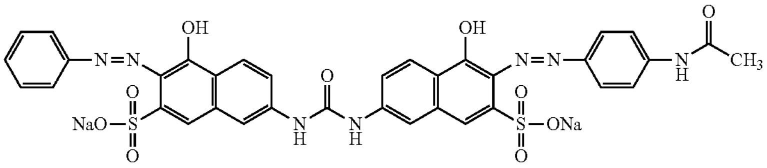 | Direct Red 23 | 3441-14-3 |
| 87 | 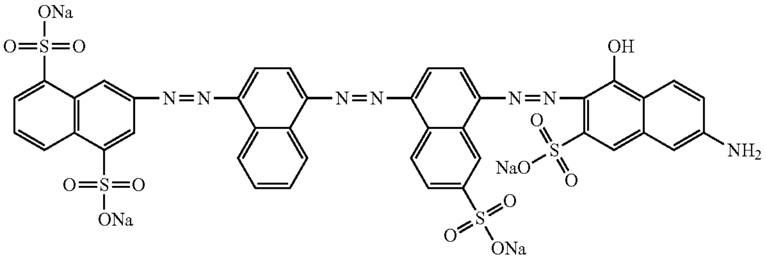 | Direct Blue 71 | 4399-55-7 |
| 88 | 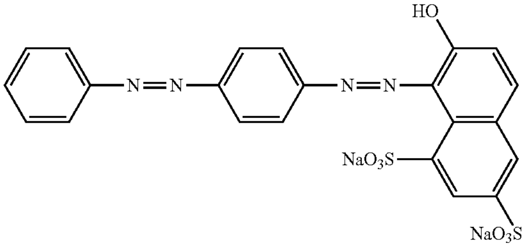 | Crocein scarlet 3B | 5413-75-2 |

TABLE 1-2
| No. | Structure | Compound name | CAS |
|---|---|---|---|
| 89 | 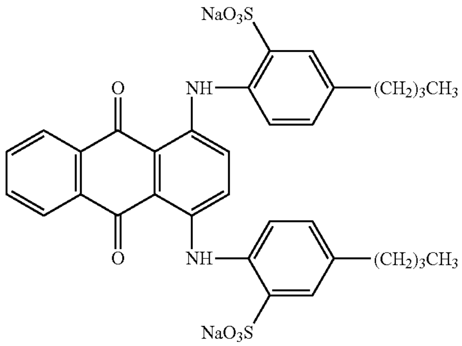 | Acid Green 27 | 6408-57-7 |
| 90 | 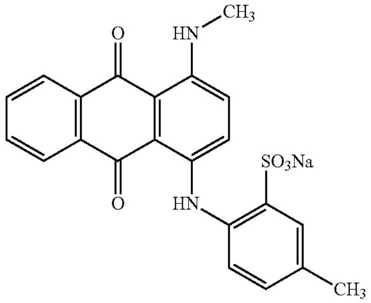 | Alizarin Astrol | 6408-51-1 |
| 91 | 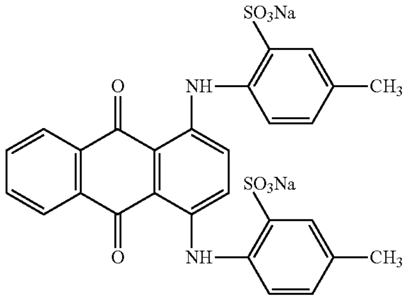 | Alizarin Cyanin Green F | 4403-90-1 |
| 92 | 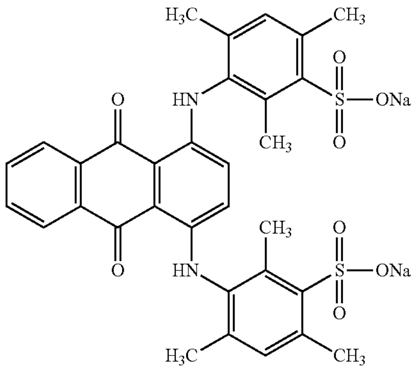 | Acid Blue 80 | 4474-24-2 |

TABLE 1-2-continued
| No. | Structure | Compound name | CAS |
|---|---|---|---|
| 93 | 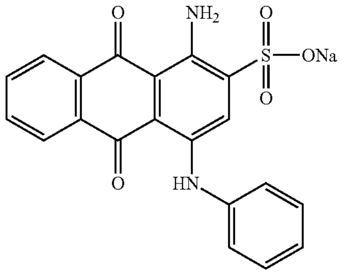 | Acid Blue 25 | 6408-78-2 |
| 94 | 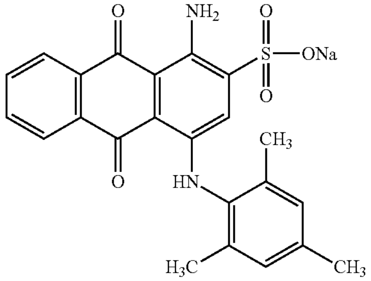 | Acid Blue 129 | 6397-02-0 |
| 95 | 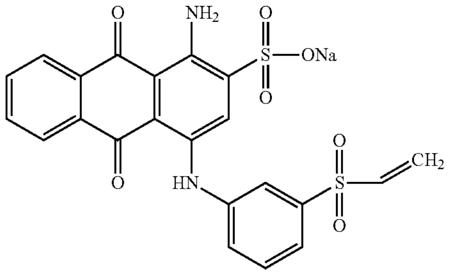 | Uniblue A sodium salt | 14541-90-3 |
| 96 | 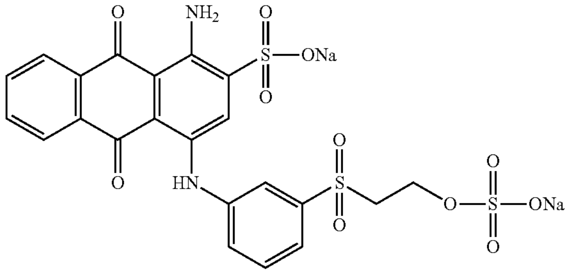 | Remazol Brilliant Blue R | 2580-78-1 |
| 97 | 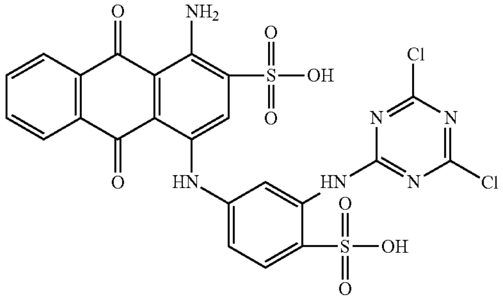 [SMILES: Nc1c(S(=O)(=O)O)cc(Nc2ccc(S(=O)(=O)O)c(Nc3nc(Cl)nc(Cl)n3)c2)c2c1C(=O)c1ccccc1C2=O] | Reactive Blue 4 | 13324-20-4 |

P-phenylenediamine and o-phenylenediamine having the following structure:

[Formula 49]

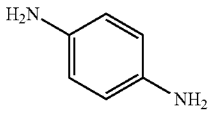

is excluded from the phenylenediamine type compound of the present invention. Further, N,N-dimethyl-p-phenylenediamine, N,N-dimethyl-o-phenylenediamine and N,N,N',N'-tetramethylphenylenediamine are also excluded from the phenylenediamine type compound of the present invention.

In one embodiment, a triphenylamine derivative having a structure of the following general formula (1):

[Formula 50]

(1)

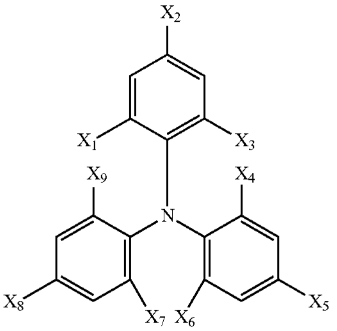

[wherein $X_1$ to $X_9$ each independently represent hydrogen, fluorine, chlorine, bromine, a cyano group, a nitro group, —N(R1)2, chain saturated hydrocarbon, chain unsaturated hydrocarbon, cyclic saturated hydrocarbon, or cyclic unsaturated hydrocarbon, and R1 is at least one member selected from the group consisting of hydrogen, chain saturated hydrocarbon, chain unsaturated hydrocarbon, cyclic saturated hydrocarbon, cyclic unsaturated hydrocarbon, a cyano group, a nitro group and a combination thereof, provided that the case where all of X1 to X9 are hydrogen is excluded] is excluded from the compound of the present invention. In another embodiment, the triphenylamine derivative having the structure above is excluded from the compound of the present invention for use in a battery.

In another embodiment, N,N'-diphenyl-N,N'-bis(p-tolyl-1,4-phenylenediamine is excluded from the compound of the present invention. In another embodiment, N,N'-diphenyl-N,N'-bis(p-tolyl)-1,4-phenylenediamine is excluded from the compound of the present invention for use in a battery.

The phenylenediamine type compound of the present invention may be modified with a functional group for covalent binding to an enzyme. A linker such as a C1 to C20 alkyl, an amino acid, or a peptide may be placed between the phenylenediamine type compound and the functional group. A hydroxyl group, an amino group, alkene, or the like may be appropriately included between the linker and the compound or the functional group. Examples of the functional group include a hydroxyl group, a carboxy group, an amino group, an aldehyde group, a hydrazino group, a thiocyanate group, an epoxy group, a vinyl group, a halogen group, an acid ester group, a phosphoric acid group, a thiol group, a disulfide group, a dithiocarbamate group, a dithiophosphate group, a dithiophosphonate group, a thioether group, a thiosulfuric acid group, a succinimide group, a maleimide group and a thiourea group.

The phenylenediamine type compound may be in a redox state and in an ionized state. In the chemical formulae described above, the phenylenediamine type compound of the present invention is described in a neutral reduced form. However, the phenylenediamine type compound of the present invention is not limited by this form and may be in an oxidized (diimine) form, a semi-oxidized form, or a reduced (diamine) form. Likewise, the azo compound or the diazonio compound of the present invention may also be in an oxidized form, a semi-oxidized form, or a reduced form. Further, the phenylenediamine type compound of the present invention may be in a neutral form or a cationic form. For the sake of convenience, when the present specification refers to the phenylenediamine type compound of the present invention, for example, the phenylenediamine type compound of the present invention represented by any of the chemical formulae, this encompasses the neutral or cationic oxidized, semi-oxidized, or reduced form thereof. For example, a neutral oxidized compound may be added as the phenylenediamine type compound of the present invention to a measurement system and then be converted to an oxidized cationic compound depending on the pH of the solution or due to electron transfer and such compound is also encompassed by (the phrase) the phenylenediamine type compound of the present invention. The phenylenediamine type compound of the present invention also encompasses a salt, an acid addition salt, an anhydride and a solvate thereof. Examples of the salt include, but are not limited to, salts of group 1 elements, salts of group 17 elements, for example, Na salt, K salt, Cl salt, and Br salt. Examples of the acid addition salt include, but are not limited to, hydrochloride, sulfate, sulfite, and nitrate.

The phenylenediamine type compound of the present invention may be artificially synthesized or may be obtained as a naturally occurring product. Alternatively, a commercially available product may be used. In the case of synthesizing the phenylenediamine type compound, organic synthesis may be performed by using a routine organic synthesis approach, and the product can be confirmed by NMR, IR, mass spectrometry, etc. The present invention is carried out by using conventional techniques of chemistry, organic synthesis, biochemistry, molecular biology, or electrochemistry, unless otherwise specified, and these are well within the competence of those skilled in the art. Such techniques are described in the literature. See, for example, Organic Chemistry (Jonathan Clayden (ed.), Nick Greeves, Stuart Warren, Peter Wothers), Oxford Univ Pr, 2000, and March's Advanced Organic Chemistry: Reactions, Mechanisms, and Structure (Michael B. Smith, Jerry March), Wiley-Interscience, 6th edition, 2007. Each of these general textbooks are incorporated herein by reference.

(Method for Fixing Enzyme or Oxidoreductase)

The enzyme or the oxidoreductase may be immobilized (fixed) to a solid phase by an arbitrary method known in the art. The enzyme, for example, an oxidoreductase, may be immobilized onto beads, a film, carbon particles, gold particles, platinum particles, a polymer, or an electrode surface. The fixation method may be a method using a cross-linking reagent, a method involving embedding (encapsulation) in a polymer matrix, a method involving covering with a dialysis membrane, a photocrosslinkable polymer, a conductive polymer, a redox polymer, or the like, or may be fixating into a polymer or adsorptive fixating onto an electrode or, alternatively, these approaches may be used in combination. Typically, the oxidoreductase is immobilized onto a carbon electrode using glutaraldehyde, and then, the glutaraldehyde is blocked by treatment with a reagent having an amine group. The amount of the oxidoreductase immobilized can be an amount capable of generating current necessary for electrochemical measurement or fuel cell power generation, and may be determined appropriately.

(Method for Adsorbing the Phenylenediamine Type Compound of Present Invention)

In one embodiment, the phenylenediamine type compound of the present invention may be present in a free state in a solution, or may be adsorbed, for example, physically adsorbed, onto beads, a membrane, carbon particles, gold particles, platinum particles, polymer, or an electrode surface. That the phenylenediamine type compound of the present invention is adsorbed on electrode surface may also be referred to as the phenylenediamine type compound immobilized to electrode surface and, in the present specification, these terms are used interchangeably. Examples of the adsorption method include a method comprising the step of dissolving the phenylenediamine type compound of the present invention in an appropriate medium, and physically contacting the solution with an electrode. In another embodiment, the phenylenediamine type compound of the present invention may be sprayed onto an electrode. The amount of the phenylenediamine type compound adsorbed can be an amount capable of generating current necessary for electrochemical measurement or battery power generation, and may be determined appropriately.

In one embodiment, the phenylenediamine type compound of the present invention may be adsorbed onto an electrode, to which an enzyme, for example, an oxidoreductase, can also be immobilized. In this case, the phenylenediamine type compound of the present invention may be adsorbed first, and subsequently, the enzyme, for example, an oxidoreductase, can be immobilized, or the enzyme, for example, an oxidoreductase, may be immobilized first, and subsequently, the phenylenediamine type compound of the present invention can be adsorbed. Alternatively, the phenylenediamine type compound may be adsorbed simultaneously with the operation of fixing the enzyme, for example, an oxidoreductase.

The final concentration of the phenylenediamine type compound of the present invention to be added to a sample solution is not particularly limited and may be, for example, 1 pM or higher, 2 pM or higher, 3 pM or higher, 4 pM or higher, 5 pM or higher, 6 pM or higher, 7 pM or higher, 8 pM or higher, 9 pM or higher, or 10 pM or higher, and 1 M or lower, 100 mM or lower, 20 mM or lower, 10 mM or lower, 5 mM or lower, 1 mM or lower, 800 μM or lower, 600 M or lower, 500 M or lower, 400 M or lower, 300 M or lower, 200 M or lower, 100 M or lower, or 50 M or lower, for example, in the range of 1 pM to 1 M, 1 pM to 100 mM, 1 pM to 20 mM, 1 pM to 10 mM, 1 pM to 5 mM, 2 pM to 1 mM, 3 pM to 800 M, 4 pM to 600 M, 5 pM to 500 M, 6 pM to 400 M, 7 pM to 300 M, 8 pM to 200 M, 9 pM to 100 μM, or 10 pM to 50 μM. The final concentration of the phenylenediamine type compound of the present invention to be added to a sample solution is not particularly limited and may be, for example, 0.000001 to 0.5% (w/v), 0.000003 to 0.3% (w/v), 0.000005 to 0.1% (w/v), 0.00001 to 0.05% (w/v), 0.00002 to 0.03% (w/v), or 0.00003 to 0.01% (w/v). The order of addition of the phenylenediamine type compound and an additional reagent is not limited, and the phenylenediamine type compound and the reagent may be added simultaneously or sequentially.

In one embodiment, the time for which redox reaction is performed or the time for which electrochemical measurement is performed can be 60 minutes or shorter, 30 minutes or shorter, 10 minutes or shorter, 5 minutes or shorter, or 1 minute or shorter. Alternatively, for an enzyme sensor, a battery, or the like for long-term measurement, the time for which redox reaction is performed can be 60 minutes or longer, 120 minutes or longer, 1 day or longer, 2 days or longer, 3 days or longer, 1 week or longer, 2 weeks or longer, or 3 weeks or longer. For example, in the case of using the phenylenediamine type compound with an oxidoreductase, the concentration of each component in a reagent for electrochemical measurement can be adjusted according to the concentration range of the reduced mediator contained in a sample or presumed to be produced in a sample.

Unless otherwise specified, the enzyme comprised in the composition of the present invention or the enzyme immobilized to the electrode of the present invention is a purified enzyme. Cell extracts, cell homogenates, or liquid crude enzyme extracts containing the enzyme contain various contaminating substances (foreign substances) in addition to the enzyme. For example, the amount of riboflavin in liquid crude enzyme extracts from a microbe is reported to be approximately 53 to 133 M (J Indust Micro Biotech 1999, 22, pp. 8-18). Such liquid crude enzyme extracts, etc., when subjected directly to electrochemical measurement, interfere with electron transfer to electrodes, for example, due to contaminating substances receiving electrons. Therefore, for the liquid crude enzyme extracts, it is difficult to achieve accurate electrochemical measurement at this riboflavin concentration. Accordingly, the electrochemical measurement method of the present invention can employ an enzyme from which contaminating substances have been removed. In the present specification, the phrase "enzyme has been purified or is a purified enzyme" does not necessarily require that the protein should be a pure product, and means that contaminating substances have been removed from the enzyme preparation to an extent under which electrochemical measurement can be carried out.

(Activity Measurement of Oxidoreductase)

The activity measurement of an oxidoreductase will be described by taking glucose dehydrogenase (GDH) as a specific example of the enzyme. GDH (EC 1.1.99.10) catalyzes reaction to produce glucono-6-lactone by oxidizing a hydroxy group of glucose. In this reaction, an electron acceptor becomes a reduced electron acceptor by receiving an electron. The activity of GDH can be measured by utilizing this action principle and using, for example, the following measurement system using phenazine methosulfate (PMS) and 2,6-dichloroindophenol (DCIP) as electron acceptors.

(Reaction 1) D-Glucose+PMS (oxidized form)→
D-glucono-δ-lactone+PMS (reduced form)

(Reaction 2) PMS (reduced form)+DCIP (oxidized form)→
PMS (oxidized form)+DCIP (reduced form)

More specifically, first, in (reaction 1), PMS (reduced form) is produced in association with the oxidation of D-glucose. Through (reaction 2) which proceeds subsequently, DCIP is reduced in association with the oxidation of PMS (reduced form). The degree of disappearance of this "DCIP (oxidized form)" is detected as an amount of change in absorbance at a wavelength of 600 nm, and the enzyme activity can be determined on the basis of this amount of change.

The activity of GDH can be measured according to the following procedures: 2.05 mL of a 100 mM phosphate buffer solution (pH 7.0), 0.6 mL of a 1 M D-glucose solution and 0.15 mL of a 2 mM DCIP solution are mixed and incubated at 37° C. for 5 minutes. Subsequently, 0.1 mL of a 15 mM PMS solution and 0.1 mL of an enzyme sample solution are added thereto to start the reaction. Absorbance is measured at the start of reaction and over time. The amount of decrease per minute in absorbance at 600 nm (AA600) in association with the progression of the enzyme reaction is determined, and the GDH activity is calculated according to the formula below. In this respect, as for the GDH activity, the amount of the enzyme reducing 1 μmol of DCIP for 1 minute in the presence of D-glucose having a concentration of 200 mM at 37° C. is defined as 1 U.

$$GDH\text{ activity }(U/\text{mL}) = \frac{-(\Delta A600 - \Delta A600_{blank}) \times 3.0 \times df}{16.3 \times 0.1 \times 1.0} \quad \text{[Mathematical formula 1]}$$

In the formula above, 3.0 represents the liquid volume (mL) of reaction reagent+enzyme reagent, 16.3 represents the millimolar molecular extinction coefficient ($cm^2/\mu mol$) under these activity measurement conditions, 0.1 represents the liquid volume (mL) of the enzyme solution, 1.0 represents the optical path length (cm) of a cell, $\Delta A600_{blank}$ represents the amount of decrease per minute in absorbance at 600 nm when reaction is started by the addition of a 100 mM phosphate buffer solution (pH 7.0) instead of the enzyme sample solution, and df represents the dilution factor.

The kit for electrochemical measurement of the present invention comprises the phenylenediamine type compound of the present invention or an electrode modifying agent comprising the phenylenediamine type compound, in an amount sufficient for at least one time of assay. Typically, the kit for electrochemical measurement of the present invention comprises an oxidoreductase, a buffer solution necessary for assay, a substrate standard solution for preparation of a calibration curve, and a guideline, in addition to the phenylenediamine type compound of the present invention. The oxidoreductase may be, for example, GDH. In this case, the substrate standard solution may be a glucose standard solution.

In one embodiment, the kit for electrochemical measurement of the present invention comprises the phenylenediamine type compound of the present invention and the oxidoreductase as one reagent. In another embodiment, the kit for electrochemical measurement of the present invention comprises the phenylenediamine type compound and the oxidoreductase as separate reagents. In another embodiment, the oxidoreductase may be immobilized to an electrode and the kit for electrochemical measurement of the present invention for use in such electrode comprises the phenylenediamine type compound as a single reagent. In this context, however, a single reagent does not mean that the reagent does not contain any substance other than the phenylenediamine type compound. The single reagent may contain an appropriate medium such that the phenylenediamine type compound of the present invention can be dissolved in the single reagent. The medium can be any medium that dissolves the phenylenediamine type compound of the present invention and examples thereof include, but are not limited to, water, methanol, ethanol, propanol, acetone, and acetonitrile. The phenylenediamine type compound of the present invention can be provided in various forms, for example, as a powder solid reagent, as a reagent immobilized to beads or an electrode surface, or as a solution in a suitable preservation solution, for example, a light-shielded solution.

One example of the electrochemical measurement includes the measurement of glucose concentrations. For colorimetric electrochemical measurement, the measurement of glucose concentrations can be performed, for example, as described below. A reactive layer for electrochemical measurement is allowed to retain a liquid or solid composition containing glucose dehydrogenase (GDH) and one or more substances selected from the group consisting of N-(2-acetamido)imidodiacetic acid (ADA), bis(2-hydroxyethyl)iminotris(hydroxymethyl)methane (Bis-Tris), sodium carbonate and imidazole as a reaction accelerator. In this context, the reactive layer may be supplemented, if necessary, with a pH buffer and a color reagent (indicating reagent). A sample containing glucose is added thereto and reacted for a given time. During this reaction, absorbance corresponding to the maximum absorption wavelength of a dye produced by polymerization or a reduced dye through direct receipt of an electron from GDH is monitored. The glucose concentration in the sample can be calculated on the basis of a calibration curve prepared in advance using glucose solutions having standard concentrations, from the rate of change per time in absorbance in a rate method or from change in absorbance up to the point in time when glucose in the sample is completely oxidized in an endpoint method.

As the color reagent (indicating reagent) that can be used in this method, for example, 2,6-dichloroindophenol (DCIP) is added as the electron acceptor, and decrease in absorbance at 600 nm can be monitored to quantify glucose. Alternatively, the glucose concentration may be calculated by adding nitro tetrazolium blue (NTB) as the color reagent and measuring absorbance at 570 nm, thereby determining the amount of diformazan produced. As a matter of course, the color reagent (indicating reagent) used is not limited thereto.

In one embodiment, a sensor that can detect the compound of the present invention can be prepared by utilizing the property of the compound of the present invention of being able to be adsorbed onto an electrode. An electrode, for example, a carbon electrode, is inserted into a solution containing the compound of the present invention, for example, DPPD, and the amount of the compound of the present invention can be quantitatively or qualitatively detected by electrochemical measurement, for example, CV or chronoamperometry, in this solution or after re-insertion into another measurement solution after a lapse of given time.

(Enzyme Sensor)

In one embodiment, the present invention provides an enzyme sensor comprising an electrode onto which an oxidoreductase is immobilized and the electrode modifying agent of the present invention is adsorbed. Examples of the electrode of the enzyme sensor include carbon electrodes, gold electrodes, and platinum electrodes and this electrode can be coated with the oxidoreductase, or the oxidoreductase can be immobilized onto the electrode. Further, the enzyme sensor may comprise fine metal particles comprising at least one type of element selected from Co, Pd, Rh, Ir, Ru, Os, Re, Ni, Cr, Fe, Mo, Ti, Al, Cu, V, Nb, Zr, Sn, In, Ga, Mg, Pb, Au, Pt, and Ag as a conductive material. These particles may be composed of an alloy or may be plated. The carbon also includes carbon nanotubes, carbon black, graphite, fullerene, and derivatives thereof. For the method for fixing the oxidoreductase, see the preceding paragraph "Method for fixing enzyme or oxidoreductase".

In one embodiment, an example of the enzyme sensor of the present invention includes a glucose sensor. This glucose sensor may comprise the phenylenediamine type compound of the present invention adsorbed onto an electrode and GDH or glucose oxidase (GOD) immobilized to the electrode. The glucose sensor may be used in continuous blood sugar monitoring or continuous glucose monitoring.

The electrode, the enzyme sensor, and the composition for electrochemical measurement of the present invention can be used in various electrochemical measurement approaches by using a potentiostat, a galvanostat, or the like. Examples of the electrochemical measurement method include various approaches such as amperometry, for example, chronoamperometry and potential step chronoamperometry, voltammetry, for example, cyclic voltammetry and differential pulse voltammetry, potentiometry, and coulometry. For example, when the substrate to be measured is glucose, the glucose concentration in a sample can be measured by measuring the current according to the amperometry method when glucose is being reduced. The applied voltage can be set to, for example, −1000 mV to +1000 mV (vs. Ag/AgCl), although this may differ depending on conditions or apparatus settings.

Incidentally, whether or not a test compound is adsorbed onto an electrode can be confirmed by cyclic voltammetry. How the maximum value of oxidation current ($I_{Omax}$) and the maximum value of reduction current ($I_{Rmax}$) change can be examined at varying sweep rates in varying ranges from 10 mV/sec to 50 mV/sec, for example. In general, it is known that when a mediator is adsorbed onto an electrode, the sweep rate and the values of $I_{Omax}$ and $I_{Rmax}$ have a proportional relationship in cyclic voltammetry. When the mediator is diffused, $I_{Omax}$ and $I_{Rmax}$ are proportional to the one-half power of the sweep rate. Whether the compound is adsorbed or diffused is determined from the relationship between $I_{Omax}$ and $I_{Rmax}$ and the sweep rate.

One example of the electrochemical measurement includes the electrochemical measurement of glucose. In one embodiment, the present invention provides an electrochemical measurement method for glucose, comprising the steps of: contacting a sample that may contain glucose with the phenylenediamine type compound and a purified glucose oxidase or purified glucose dehydrogenase; and measuring the current. The phenylenediamine type compound may be present in a solution or may be adsorbed onto an electrode. The enzyme may be immobilized to the electrode.

The electrochemical measurement of a glucose concentration can be performed, for example, as described below. A buffer solution is placed in a thermostat cell and kept at a given temperature. An electrode onto which GDH or GOD is immobilized is used as a working electrode, and a counter electrode (e.g., a platinum electrode) and a reference electrode (e.g., an Ag/AgCl electrode or an Ag/Ag+ electrode) are used. The phenylenediamine type compound of the present invention is added to a reaction solution. A given voltage is applied to the carbon electrode so that the current becomes steady and then, a sample containing glucose is added thereto, and the increase of the current is measured. The glucose concentration in the sample can be calculated according to a calibration curve prepared from glucose solutions having standard concentrations. The potential to be applied can be set to, for example, +800 mV or lower, +700 mV or lower, +600 mV or lower, +500 mV or lower, +400 mV or lower, +300 mV or lower, +200 mV or lower, +100 mV or lower, or +50 mV or lower, and −200 mV or higher, −100 mV or higher, or −50 mV or higher, for example, 0 mV or higher, and can be set to, for example, +800 mV to −200 mV, +800 mV to −100 mV, +800 mV to −50 mV, +600 mV to 0 mV, +500 mV to 0 mV, +400 mV to 0 mV, +300 mV to 0 mV, or +200 mV to 0 mV (for a silver/silver chloride reference electrode). The pH of the measurement solution containing glucose may be in the range of pH 3 to 10. The pH may, for example, be pH 5, pH 6, pH 7, pH 8, pH 9, or pH 10 and the solution may contain a buffer such as glycine, acetate, citrate, phosphate, carbonate, or Good's buffer. In the case of using an enzyme other than GDH or GOD and a substrate other than glucose, the pH can also be appropriately changed for measurement.

As a specific example, the phenylenediamine type compound, for example, IPPD, is immobilized to a glassy carbon (GC) electrode in advance and then, 0.2 U to 150 U, for example, 0.5 U to 100 U, of GDH or GOD is immobilized thereto, and the response current value is measured for glucose concentration. 10.0 ml of a 100 mM potassium phosphate buffer solution (pH 6.0) is added into an electrolysis cell. The GC electrode is connected to potentiostat BAS100B/W (manufactured by BAS Inc.). The solution is stirred at 37° C., and +500 mV is applied to the silver/silver chloride reference electrode. A 1 M D-glucose solution is added with final concentrations of 5, 10, 20, 30, 40, and 50 mM to the system and the current value is measured in a steady state for each addition. This current value is plotted against the known glucose concentrations (5, 10, 20, 30, 40, and 50 mM) to prepare a calibration curve. As a result, glucose can be quantified using the GDH or GOD enzyme-immobilized electrode.

A printed electrode may be used for electrochemical measurement. This can reduce the amount of a solution necessary for measurement. The electrode may be formed on an insulating substrate. More specifically, the electrode may be formed on a substrate by a photolithography technique or a printing technique such as screen printing, gravure printing, or flexographic printing. Examples of the material for the insulating substrate include silicon, glass, ceramic, polyvinyl chloride, polyethylene, polypropylene, and polyester and a material strongly resistant to various solvents or chemicals can be used. The area of the working electrode can be set according to the desired response current. In one embodiment, the area of the working electrode can be set to, for example, 1 $mm^2$ or larger, 1.5 $mm^2$ or larger, 2 $mm^2$ or larger, 2.5 $mm^2$ or larger, 3 $mm^2$ or larger, 4 $mm^2$ or larger, 5 $mm^2$ or larger, 6 $mm^2$ or larger, 7 $mm^2$ or larger, 8 $mm^2$ or larger, 9 $mm^2$ or larger, 10 $mm^2$ or larger, 12 $mm^2$ or larger, 15 $mm^2$ or larger, 20 $mm^2$ or larger, 30 $mm^2$ or larger, 40 $mm^2$ or larger, 50 $mm^2$ or larger, 1 $cm^2$ or larger, 2 $cm^2$ or larger, 3 $cm^2$ or larger, 4 $cm^2$ or larger, or 5 $cm^2$ or larger, for example, 10 $cm^2$ or larger. In one embodiment, the area of the working electrode can beset to 10 $cm^2$ or smaller or 5 $cm^2$ or smaller, for example, 1 $cm^2$ or smaller. The same holds true for the counter electrode. The apparent surface area of the working electrode may be increased by fixing a carbon nanotube, graphene, ketjen black, or the like onto the same. In this case, the apparent area may be increased by 10 or more times, 50 or more times, 100 or more times, or 1000 or more times.

In one embodiment, in the case of using the electrode modifying agent, the electrode adsorber agent or the electron transfer promoting agent of the present invention with an electrode, the electrode modifying agent, the electrode adsorber agent or the electron transfer promoting agent may be used at a physical amount of 0.1 pmol or higher, 0.2 pmol or higher, 0.3 pmol or higher, 0.4 pmol or higher, 0.5 pmol or higher, or 1 pmol or higher, and 10 mmol or lower, 5 mmol or lower, 1 mmol or lower, 800 μmol or lower, 600 μmol or lower, 500 μmol or lower, 400 μmol or lower, 300 μmol or lower, 200 μmol or lower, 100 μmol or lower, or 50 μmol or lower, for example, 0.1 pmol to 10 mmol, 0.1 pmol to 5 mmol, 0.2 pmol to 1 mmol, 0.3 pmol to 800 μmol, 0.4 pmol to 600 μmol, 0.5 pmol to 500 μmol, 0.6 pmol to 400 μmol, 0.7 pmol to 300 μmol, 0.8 pmol to 200 μmol, 0.9 pmol to 100 μmol, or 1 pmol to 50 mol, per $cm^2$ of the area of the working electrode. These numeric values are based on an area of 1 $cm^2$ of the working electrode and in the case of increasing or decreasing the area of the working electrode or using a carbon nanotube, graphene, or the like having a large specific surface area, the apparent surface area is increased and thus, the electrode modifying agent of the present invention may be used at a corresponding mole number.

(Battery of Present Invention)

In one embodiment, the present invention provides a battery comprising the phenylenediamine type compound, the electrode modifying agent, the electrode adsorber agent, or the electron transfer promoting agent of the present invention. In one embodiment, in the battery of the present invention, the compound of the present invention is immobilized to an electrode of the battery. In one embodiment, the battery of the present invention comprises an oxidoreductase. In one embodiment, the oxidoreductase may be immobilized to the electrode of the battery. In one embodiment, the present invention provides a power generation method using the battery of the present invention.

(Fuel Cell of Present Invention)

In one embodiment, the present invention provides an anode or a cathode for a fuel cell comprising the phenylenediamine type compound, the electrode modifying agent, the electrode adsorber agent, or the electron transfer promoting agent of the present invention, and a fuel cell comprising the anode or the cathode. In one embodiment, the present invention provides a power generation method using the phenylenediamine type compound of the present invention or an electrode onto which the phenylenediamine type compound is adsorbed, and a power generation method using an oxidoreductase such as GDH or GOD immobilized to an anode electrode and a substrate corresponding to the oxidoreductase, for example, glucose, as the fuel. In the case of fixing the oxidoreductase described above, a compound serving as a substrate for the immobilized oxidoreductase can be appropriately used as a fuel.

In one embodiment, the fuel cell (fuel battery) of the present invention comprises an anode or a cathode on which the phenylenediamine type compound of the present invention is adsorbed, a fuel tank, a cathode, an anode having an oxidoreductase, and an electrolyte. In the fuel cell of the present invention, a load resistance can be placed, if necessary, between the anode and the cathode, and the fuel cell may comprise wirings therefor. In one embodiment, the load resistance is a part of the fuel cell of the present invention. In one embodiment, the load resistance is not a part of the fuel cell of the present invention, and the fuel cell of the present invention is configured such that the fuel cell can be connected to an appropriate load resistance. In the fuel cell of the present invention, the oxidoreductase constitutes a portion of the anode. For example, the oxidoreductase may be located in proximity to or in contact with the anode, may be immobilized thereto, or may be adsorbed thereonto. The fuel tank contains a compound serving as a substrate for the oxidoreductase immobilized to the electrode. For example, in the case of fixing glucose dehydrogenase to the electrode, the fuel may be glucose. In one embodiment, the fuel cell of the present invention may have an ion-exchange membrane which separates the anode from the cathode. The ion-exchange membrane may have pores of 1 nm to 20 nm. The anode may be a typical electrode such as a carbon electrode. For example, an electrode made of conductive carbon such as carbon black, graphite, or active carbon, or an electrode made of a metal such as gold or platinum can be used. Specific examples thereof include carbon paper, carbon cloth, carbon felt, glassy carbon, and HOPG (highly oriented pyrolytic graphite). As for the cathode to be paired therewith, for example, an electrode in which an electrode catalyst, such as platinum or platinum alloy, which is used in general in fuel cells is supported on a carbon material such as carbon black, graphite, carbon cloth, carbon felt, or active carbon, or a conductor made of gold, platinum, or the like, or a conductor made of an electrode catalyst itself such as platinum or platinum alloy is used as the cathode electrode and can be in a form in which an oxidizing agent (cathode-side substrate, oxygen, etc.) is supplied to the electrode catalyst. In one embodiment, the mercury electrodes are excluded from the electrode of the present invention.

In another embodiment, a substrate reduction-type enzyme electrode may be used as the cathode to be paired with the anode consisting of the substrate oxidation-type enzyme electrode as described above. Examples of the oxidoreductase that reduces the oxidizing agent include enzymes known in the art such as laccase and bilirubin oxidase. In the case of using an oxidoreductase as a catalyst reducing the oxidizing agent, a known electron transfer mediator may be used, if necessary. The mediator for the cathode may be the same as or different from the mediator for the anode. Examples of the oxidizing agent include oxygen and hydrogen peroxide.

In one embodiment, an oxygen-selective membrane (e.g., a dimethylpolysiloxane membrane) can be placed around the cathode electrode in order to circumvent the influence of impurities (ascorbic acid, uric acid, etc.) interfering with electrode reaction in the cathode.

The power generation method of the present invention comprises the step of supplying a fuel compound serving as a substrate for an oxidoreductase to an anode having the oxidoreductase. When the fuel is supplied to the anode having the oxidoreductase, the substrate is oxidized and the oxidoreductase delivers an electron generated at the same time therewith, to the electron transfer mediator, for example, the phenylenediamine type compound, which mediates electron transfer between the oxidoreductase and the electrode and the electron transfer mediator delivers the electron to a conductive substrate (anode electrode). The electron arrives at the cathode electrode through wiring (external circuit) from the anode electrode, thereby generating a current.

Protons ($H^+$) generated in the process described above migrate within an electrolyte solution to the cathode electrode. Then, in the cathode electrode, a proton that has migrated within the electrolyte solution from the anode, the electron that has migrated from the anode side through the external circuit, and an oxidizing agent (cathode-side substrate) such as oxygen or hydrogen peroxide react and produce water. Electricity can be generating by utilizing this mechanism.

(Organic Battery of Present Invention)

In one embodiment, the present invention provides an organic battery comprising the phenylenediamine type compound, the electrode modifying agent, the electrode adsorber agent, or the electron transfer promoting agent of the present invention. The electrode modifying agent, the electrode adsorber agent, or the electron transfer promoting agent may be adsorbed onto an electrode. Examples of the electrode material for use in the organic battery include, but are not limited to, quinone, indigo derivatives, benzoquinone compounds having a methoxy group, indigo carmine, and pentacenetetrone. Examples of the electrode material for use in organic radical batteries include, but are not limited to, electrode materials in which a compound having a nitroxyl radical, for example, 2,2,6,6-tetramethylpiperidine-N-oxyl, is bound to a polymer such as polymethacrylate or acrylate, and lithium. See, for example, Polymer, vol. 54, December issue, 2005, p. 886. In the organic battery, the electrode modifying agent of the present invention may be used as an electron mediator on the anode-side or the cathode-side.

The electrode modifying agent comprising the phenylenediamine type compound of the present invention or an electrode onto which the electrode modifying agent is adsorbed can be used in various electrochemical measurements. The electrode can be utilized in an enzyme sensor by fixing an oxidoreductase to the electrode. Furthermore, the electrode modifying agent comprising the phenylenediamine type compound of the present invention or an electrode onto which the electrode modifying agent is adsorbed can be used in a fuel cell or an organic battery. These descriptions are given merely for illustration, and use of the electrode modifying agent comprising the phenylenediamine type compound of the present invention or an electrode onto which the electrode modifying agent is adsorbed is not limited thereto.

Hereinafter, the present invention will be further illustrated with reference to the Examples. However, the technique scope of the present invention is not limited by these examples in any way.

EXAMPLES

Material and Method

Materials and reagents were commercially available, or were obtained or prepared according to routine approaches of the technical field or procedures of literatures known in the art, unless otherwise specified. The single-layered carbon nanotube used is manufactured by Sigma-Aldrich Co., LLC, Meijo Nano Carbon Co., Ltd., or Zeon Nano Technology Co., Ltd. The multilayered carbon nanotube used is manufactured by Sigma-Aldrich Co., LLC, Meijo Nano Carbon Co., Ltd., or Kanto Chemical Co., Inc. The carbon nanotube used was appropriately dispersed by ultrasonication in an aqueous solution containing a low-molecular surfactant, a water-soluble polymer, a water-soluble polysaccharide, and the like. The surfactant used is, but is not limited to, Triton X-100, sodium dodecyl sulfate, or the like. The compounds N-methyl-N'-phenyl-p-phenylenediamine, N-ethyl-N'-phenyl-p-phenylenediamine, N-isopropyl-N'-(4-aminophenyl)-p-phenylenediamine, 2-amino-4-isopropylamino-diphenylamine, and N-isopropyl-N'-(4-hydroxyphenyl)-p-phenylenediamine were obtained from NARD institute, Ltd. Their production procedures are as described below.

The following scheme was used to synthesize N-Methyl-N'-phenyl-p-phenylenediamine (indicated as compound 1-1 in the scheme) and N-ethyl-N'-phenyl-p-phenylenediamine (indicated as compound 1-2 in the scheme).

[Formula 51]

compound 1-1

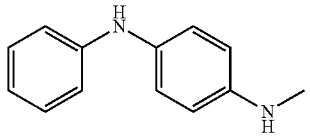

Molecular Weight: 198.27 compound 1-2

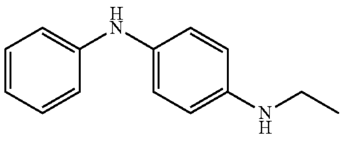

Molecular Weight: 212.30

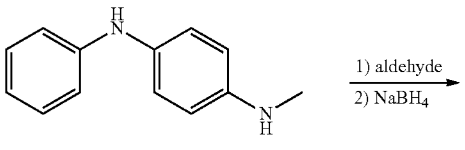

Molecular Weight: 184.24

-continued

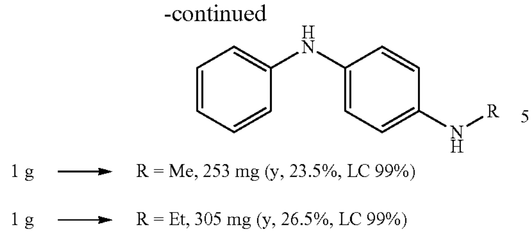

Each product was purified through a silica gel column (developing solvent: heptane/ethyl acetate) and confirmed by mass spectrometry and NMR. Compound 1-1: $[M+H]^+$ ion m/z=calcd 199.1, found 199.1. Compound 1-2: $[M+H]^+$ ion m/z=calcd 213.1, found 213.1.

The following scheme was used to synthesize N-Isopropyl-N'-(4-aminophenyl)-p-phenylenediamine (indicated as compound 2-2 in the scheme) and N-isopropyl-N'-(4-hydroxyphenyl)-p-phenylenediamine (indicated as compound 2-3 in the scheme).

[Formula 52]

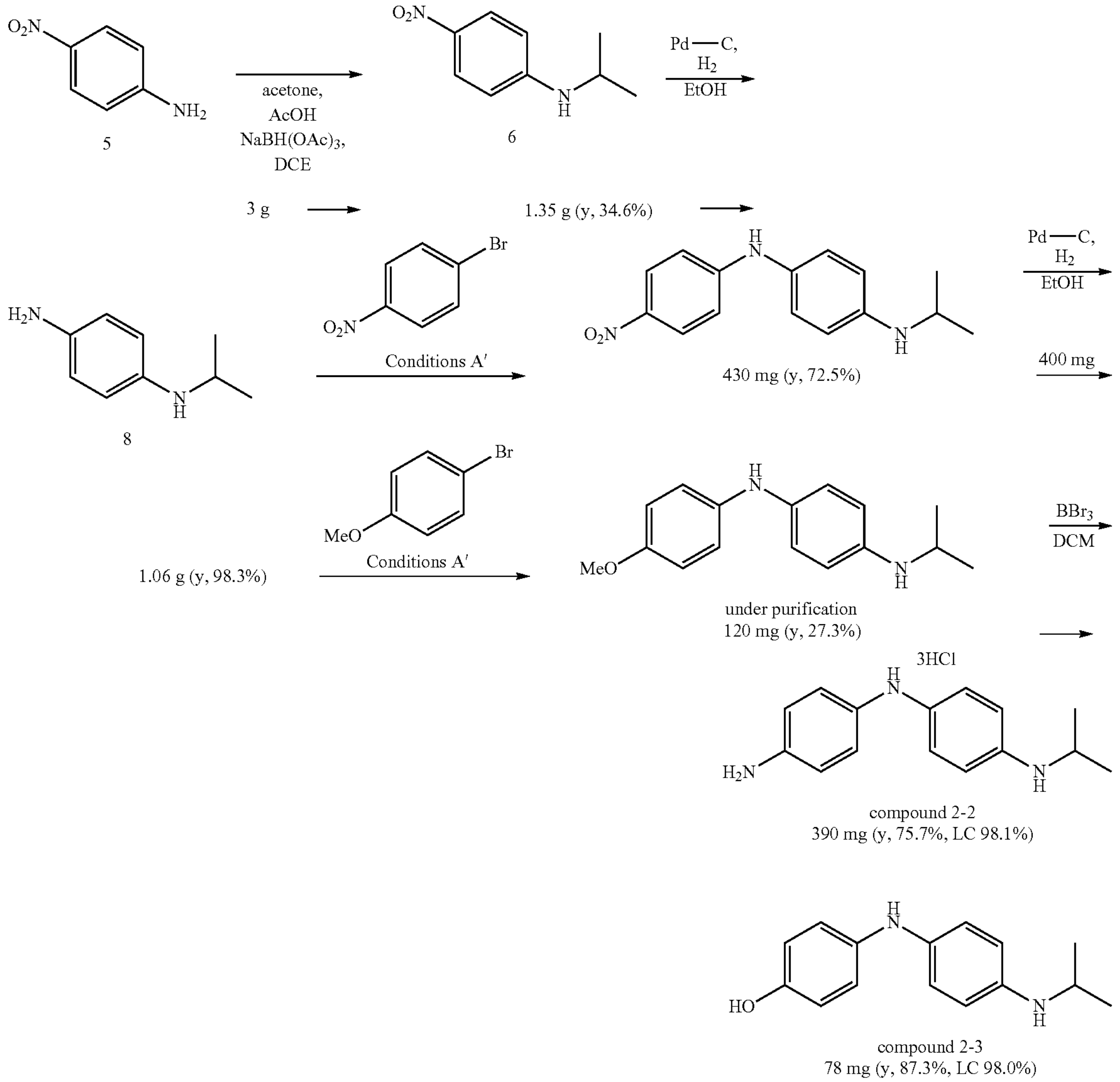

compound 2-2
390 mg (y, 75.7%, LC 98.1%)

compound 2-3
78 mg (y, 87.3%, LC 98.0%)

Each product was purified through a silica gel column (developing solvent: heptane/ethyl acetate) and confirmed by mass spectrometry and NMR. Compound 2-2: $[M+H]^+$ ion m/z=calcd 242.1, found 242.1. Compound 3-2: $[M+H]^+$ ion m/z=calcd 243.1, found 243.0.

The following scheme was used to synthesize 2-Amino-4-isopropylamino-diphenylamine (indicated as compound 2-1 in the scheme).

[Formula 53]

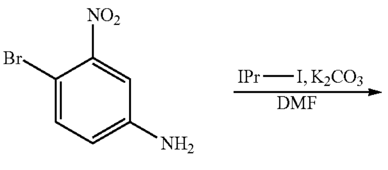

1

-continued

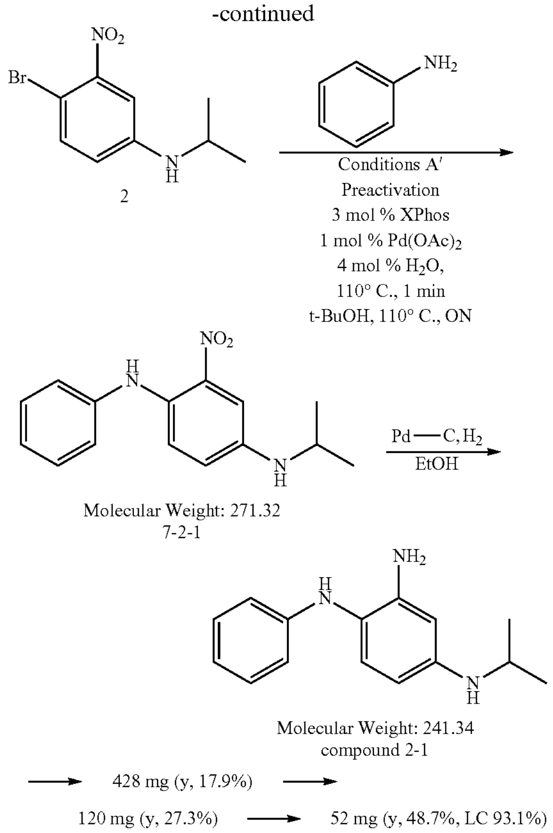

The product was purified through a silica gel column (developing solvent: heptane/ethyl acetate) and confirmed by mass spectrometry and NMR. Compound 2-1: $[M+H]^+$ ion m/z=calcd 242.1, found 242.2.

Other compounds were obtained as commercially available products from TCI or Sigma-Aldrich Co., LLC.

Example 1. Introduction of GDH Gene Derived from Genus *Mucor* to Host and Confirmation of GDH Activity The amino acid sequence of GDH derived from the genus *Mucor* (MpGDH) described in Japanese Patent No. 4648993 is shown in SEQ ID NO: 1, and the nucleotide sequence thereof is shown in SEQ ID NO: 2. A gene encoding modified GDH (MpGDH-M2) in which N66Y/N68G/C88A/A175C/N214C/Q233R/T387C/G466D/E554D/L557V/S559K mutation was introduced in MpGDH was obtained. The amino acid sequence of MpGDH-M2 is shown in SEQ ID NO: 3, and the nucleotide sequence of the gene is shown in SEQ ID NO: 4. The MpGDH-M2 gene of interest was inserted to the multicloning site of plasmid pUC19 by a routine method to prepare a DNA construct. More specifically, the pUC19 used was pUC19 linearized vector attached to In-Fusion HD Cloning Kit (Clontech Laboratories, Inc.). The MpGDH-M1 gene was ligated to In-Fusion Cloning Site located at the multicloning site of pUC19 using the In-Fusion HD Cloning Kit described above according to the protocol attached to the kit to obtain a plasmid for the construct (pUC19-MpGDH-M2).

The gene was expressed in *Aspergillus sojae*, and the GDH activity was evaluated.

More specifically, for the purpose of obtaining MpGDH-M2, double-joint PCR (Fungal Genetics and Biology, 2004, vol. 41, p. 973-981) was performed using the GDH gene to construct a cassette composed of 5' arm region-pyrG gene-TEF1 promoter gene-flavin binding GDH gene-3' arm region, which was then used in the transformation of an *Aspergillus sojae* NBRC4239 strain-derived pyrG disruptant (strain deficient in a 48 bp upstream region, an 896 bp coding region, and a 240 bp downstream region of the pyrG gene) according to procedures described below. The pyrG gene is an uracil auxotrophic marker. Conidia of the *Aspergillus sojae* NBRC4239 strain-derived pyrG disruptant were inoculated to 100 ml of a polypeptone-dextrin liquid medium containing 20 mM uridine in a 500 ml Erlenmeyer flask, and shake-cultured at 30° C. for approximately 20 hours, followed by the recovery of the fungus body. Protoplasts were prepared from the recovered fungus body. The obtained protoplasts and 20 g of the DNA construct having an insert of the gene of interest were used for transformation with the protoplast PEG method, and subsequently incubated at 30° C. for 5 days or more using Czapek-Dox minimum medium (Difco; pH 6) containing 0.5% (w/v) agar and 1.2 M sorbitol to obtain transformed *Aspergillus sojae* having the ability to form colonies.

The obtained transformed *Aspergillus sojae* became able to survive in a uridine-free medium by the introduction of the pyrG gene compensating uridine-dependent growth, and thereby could be selected as a strain harboring the gene of interest. Transformants of interest were confirmed by PCR and selected from among the strains thus obtained.

GDH production was performed using the transformed *Aspergillus sojae* obtained by transformation with the gene of the MpGDH mutant.

Conidia of each strain were inoculated to 40 ml of DPY liquid medium (1% (w/v) polypeptone, 2% (w/v) dextrin, 0.5% (w/v) yeast extracts, 0.5% (w/v) $KH_2PO4$, 0.05% (w/v) $MgSO_4 \cdot 7H_20$; pH unadjusted) in a 200 ml Erlenmeyer flask, and shake-cultured at 160 rpm at 30° C. for 4 days. Subsequently, the fungus body was filtered from the cultures thus obtained, and the obtained medium supernatant fraction was concentrated into 10 mL and desalted using Amicon Ultra-15, 30K NMWL (manufactured by Millipore Corp.) and replaced with a 20 mM potassium phosphate buffer solution (pH 6.5) containing 150 mM NaCl. Subsequently, the resultant was applied to HiLoad 26/60 Superdex 200 pg (manufactured by GE Healthcare Japan Corp.) equilibrated with a 20 mM potassium phosphate buffer solution (pH 6.5) containing 150 mM NaCl, followed by elution with this buffer solution and a fraction exhibiting GDH activity was recovered to obtain a purified preparation of MpGDH-M2. This enzyme was in a state bound to FAD via its FAD binding site (holoenzyme).

Example 2. Confirmation of Adsorbability of the Phenylenediamine Type Compound onto a Carbon Electrode Three phenylenediamine type compounds (N-isopropyl-N'-phenyl-p-phenylenediamine (IPPD, manufactured by Tokyo Chemical Industry Co., Ltd., product code: P0327), N,N'-diphenyl-p-phenylenediamine (DPPD, manufactured by Tokyo Chemical Industry Co., Ltd., product code: D0609), and N-(1,3-dimethylbutyl)-N'-phenyl-p-phenylenediamine (6PPD, manufactured by Tokyo Chemical Industry Co., Ltd., product code: D3331) were used to perform cyclic voltammetry (CV) with a printed electrode. More specifically, SCREEN-PRINTED ELECTRODES (manufactured by Metrohm Dropsens, S.L., product No. DRP-C110) onto which a carbon working electrode (12.6 $mm^2$) and a silver reference electrode were printed were coated with 3 μl of an aqueous solution containing IPPD having a final concentration of 10 μg/ml in 10% ethanol, and dried at room temperature. Then, the electrode was washed with ultrapure water and connected to ALS electrochemical analyzer 814D (manufactured by BAS Inc.) using a dedicated connector (manufactured by Metrohm Dropsens, S.L., DRP-CAC). The printed electrode used as a working electrode, a silver/silver chloride electrode (manufactured by BAS Inc.) used as a reference electrode, and a platinum electrode (manufactured by BAS Inc.) used as a counter electrode were dipped into 10 mL of a 100 mM potassium phosphate buffer solution (pH 7.0). While this solution was stirred at 650 rpm, cyclic voltammetry was performed by sweeping voltage in the range from −200 mV to +400 mV (vs. Ag/AgC). The sweep rate was allowed to vary in the range from 10 mV/sec to 50 mV/sec, and how the maximum value of oxidation current ($I_{Omax}$) and the maximum value of reduction current ($I_{Rmax}$) would change was examined. In general, it is known that when a mediator is adsorbed on an electrode, the sweep rate and the values of $I_{Omax}$ and $I_{Rmax}$ have a proportional relationship in cyclic voltammetry. When the mediator is diffused, $I_{Omax}$ and $I_{Rmax}$ are proportional to the one-half power of the sweep rate.

Results of carrying out cyclic voltammetry using IPPD and plotting a sweep rate and $I_{Omax}$ and $I_{Rmax}$ are shown in FIG. 1. As a result, the sweep rate and $I_{Omax}$ and $I_{Rmax}$ were confirmed to have a proportional relationship, indicating that IPPD is adsorbed onto a carbon electrode.

Figure 2:
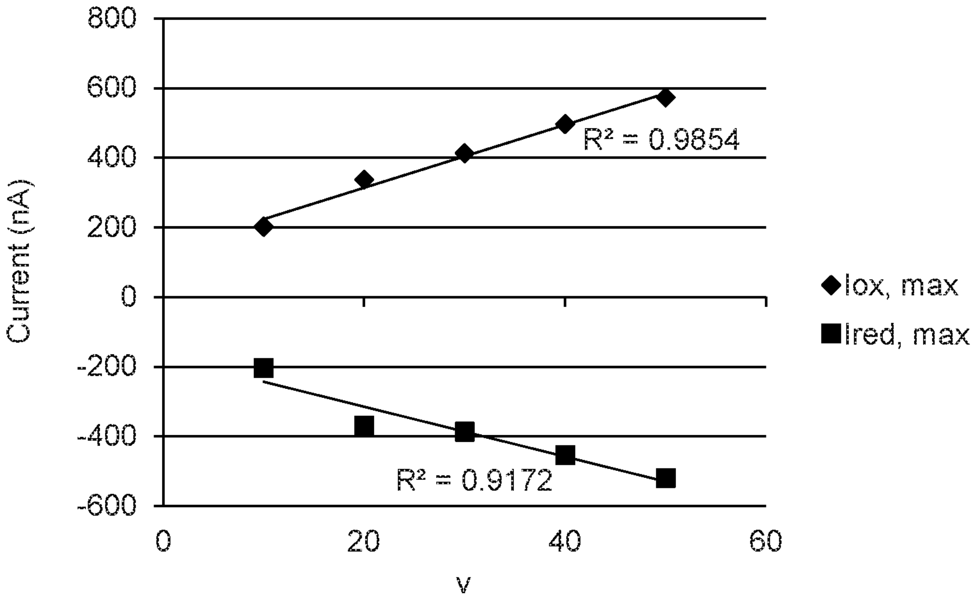
FIG. 2 shows results obtained using DPPD instead of IPPD.
Figure 3:
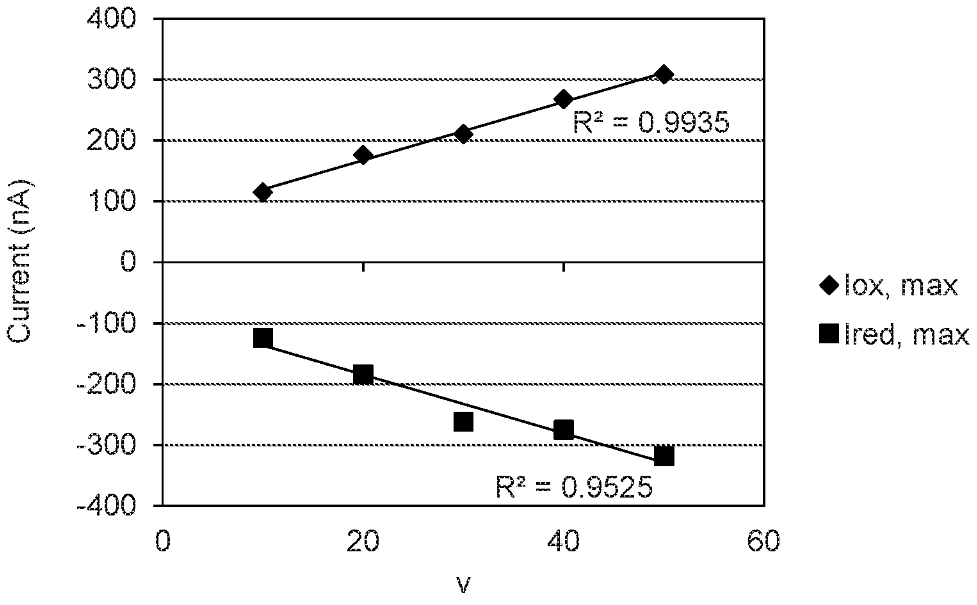
FIG. 3 shows results obtained using 6PPD instead of IPPD.

Results of conducting a similar test using DPPD and 6PPD instead of IPPD are shown in FIGS. 2 and 3, respectively. For both compounds, the sweep rate and $I_{Omax}$ and $I_{Rmax}$ were confirmed to have a proportional relationship, indicating that these compounds are adsorbed onto a carbon electrode, as in the case of IPPD.

Comparative Example (p-phenylenediamine)

A similar measurement was carried out using p-phenylenediamine already known to function as a mediator instead of the diphenylamine type compound of the present invention. As a result, neither an oxidation wave nor a reduction wave was observed. It is indicated that p-phenylenediamine was detached from the electrode due to the washing of the electrode with ultrapure water or dipping in a potassium phosphate buffer solution.

Figure 4:
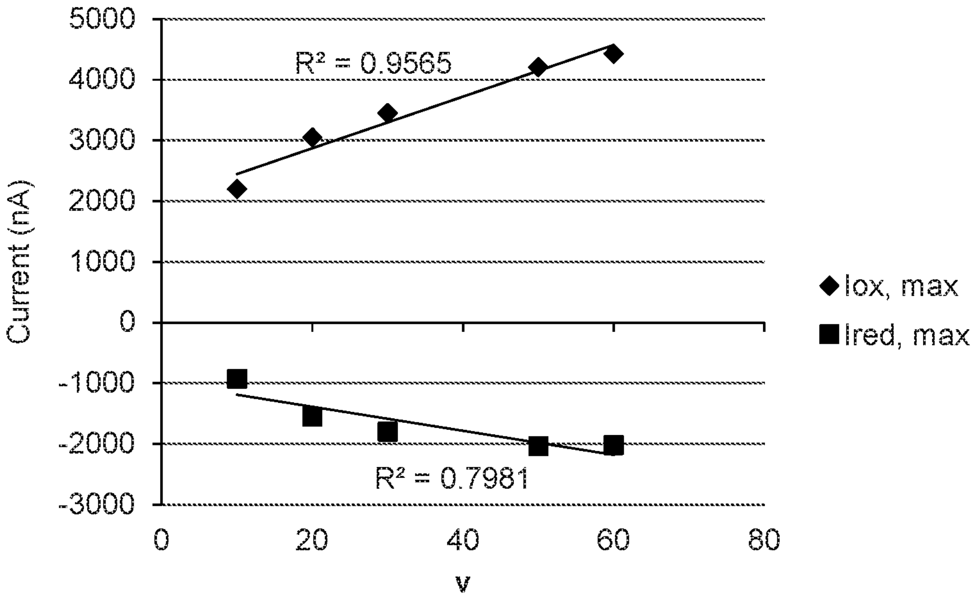
FIG. 4 shows results obtained using p-phenylenediamine instead of IPPD.
Figure 5:
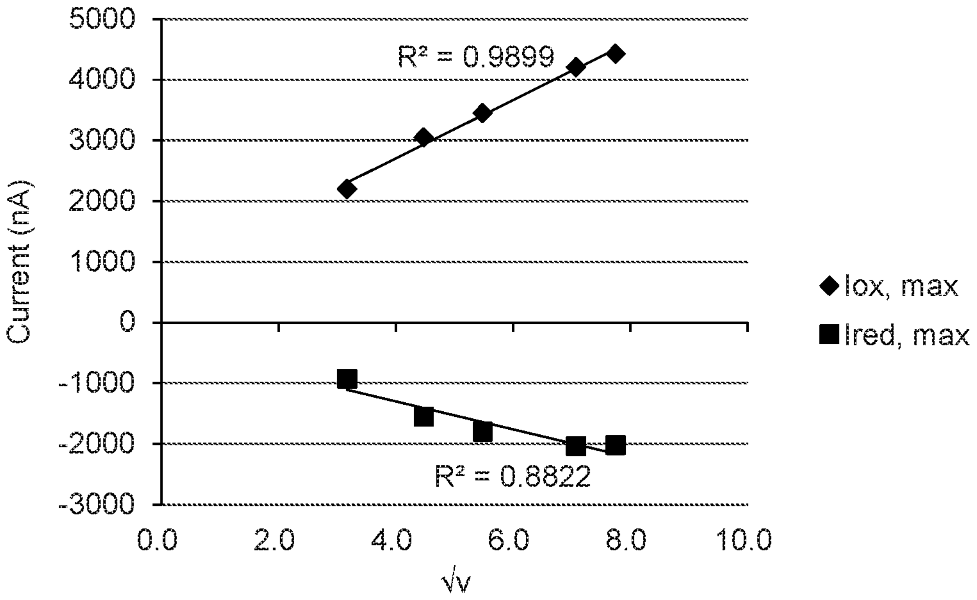
FIG. 5 shows results obtained using p-phenylenediamine instead of IPPD. The abscissa depicts a square root of the sweep rate.

The printed electrode described above was loaded with 10 μl of a solution containing p-phenylenediamine having a final concentration of 100 μg/ml in 10% ethanol and 10 μl of a 100 mM potassium phosphate buffer solution (pH 7.0), and cyclic voltammetry was performed by sweeping voltage in the range from −200 mV to +400 mV (vs. Ag/Ag+). As a result, as shown in FIGS. 4 and 5, $I_{Omax}$ and $I_{Rmax}$ were confirmed to be proportional to the one-half power of the sweep rate. This indicates that p-phenylenediamine is diffused without being adsorbed onto an electrode.

Example 3. Confirmation of Adsorbability of the Compound of Present Invention onto a Carbon Electrode Bindschedler's green leuco base (BGLB, manufactured by Tokyo Chemical Industry Co., Ltd., product code: B0482, CAS No. 637-31-0) or tris[4-(diethylamino)phenyl]amine (TDPA, manufactured by Sigma-Aldrich Co. LLC, product code: 556394, CAS No. 5981-09-9) was used to perform cyclic voltammetry (CV) with a printed electrode. More specifically, the compound was adsorbed onto SCREEN-PRINTED ELECTRODES (manufactured by Metrohm Dropsens, S.L., product No. DRP-C110) in which a carbon working electrode (12.6 $mm^2$) and a silver reference electrode were printed, using an ethanol solution containing BGLB having a final concentration of 1 mg/ml. Then, cyclic voltammetry was carried out in the same manner as in Example 2.

Figure 6:
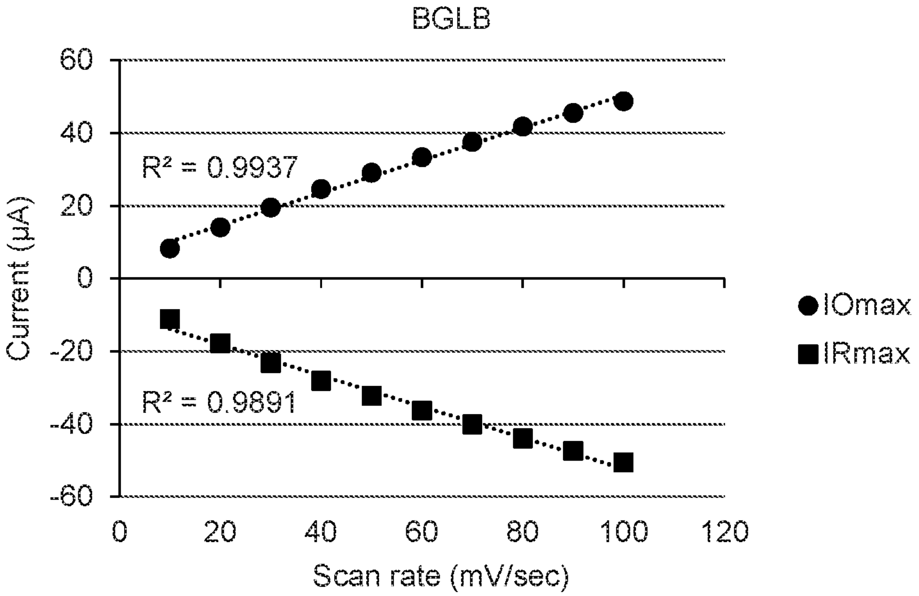
FIG. 6 shows results obtained using BGLB instead of IPPD.

Results of plotting a sweep rate and $I_{Omax}$ and $I_{Rmax}$ in measurement using BGLB are shown in FIG. 6. As a result, the sweep rate and $I_{Omax}$ and $I_{Rmax}$ were confirmed to have a proportional relationship, indicating that BGLB is adsorbed onto a carbon electrode.

Figure 7:
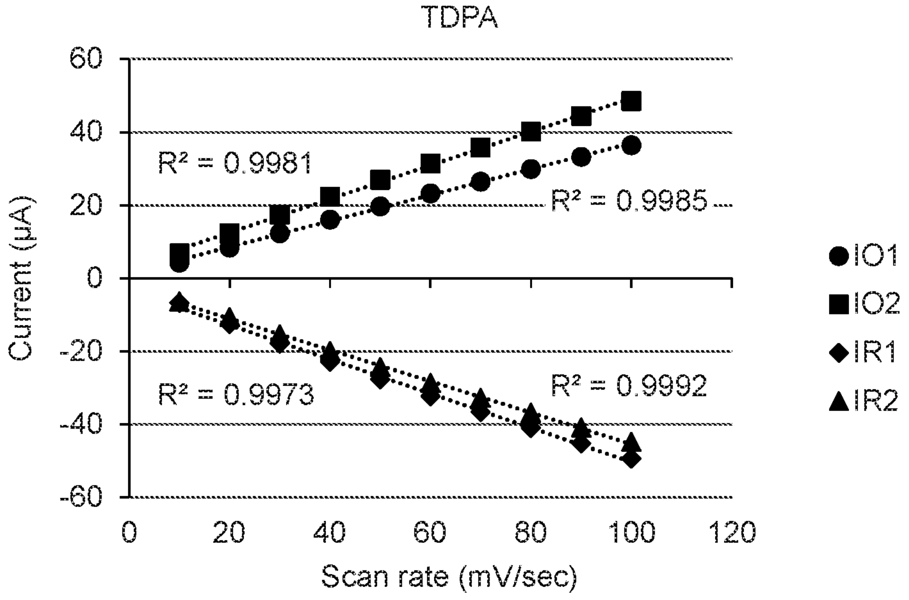
FIG. 7 shows results obtained using TDPA instead of BGLB.

Results of conducting a similar test using TDPA instead of BGLB are shown in FIG. 7. TDPA has two redox waves, which are therefore indicated by $I_{O1}$, $I_{O2}$, $I_{O2}$, $I_{R1}$ and $I_{R2}$ in the figure. When TDPA was used, the sweep rate and $I_{Omax}$ and $I_{Rmax}$ were also confirmed to have a proportional relationship, indicating that the compound is adsorbed onto a carbon electrode, as in the case of BGLB.

The following compounds were similarly confirmed to be adsorbed onto an electrode by the same approach as above using a round carbon electrode (manufactured by BioDevice Technology, Ltd., DEP-Chip EP-PP) or SCREEN-PRINTED ELECTRODES (manufactured by Metrohm Dropsens, S.L., product No. DRP-C110) as the electrode.

TABLE 2

| Compound name | Manufacturer | Product code | CAS |
|---|---|---|---|
| Alizarin Astrol<br>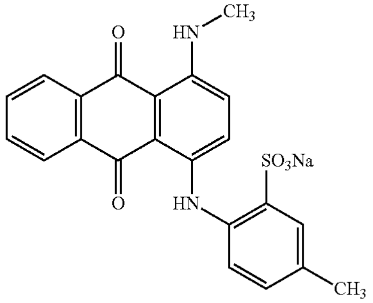 | TCI | A0609 | 6408-51-1 |

TABLE 2-continued

| Compound name | Manufacturer | Product code | CAS |
|---|---|---|---|
| Variamine Blue B Base | TCl | M0493 | 101-64-4 |
| 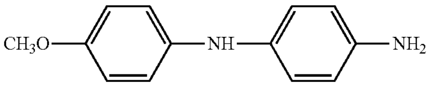 | | | |
| 4-Diazo-3-methoxydiphenylamine Sulfate | TCl | D2285 | 36305-05-2 |
| 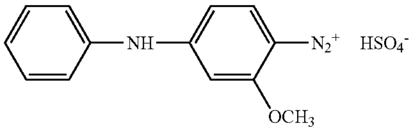 | | | |
| 4-(Dimethylamino)-4'-nitrosodiphenylamine | TCl | D3571 | 7696-70-0 |
| 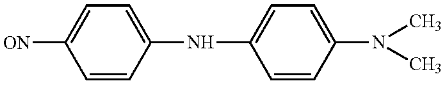 | | | |
| 4-(2-Octylamino)diphenylamine | TCl | 00166 | 15233-47-3 |
| 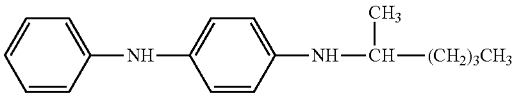 | | | |
| 4-(Phenylazo)diphenylamine | TCl | P0146 | 101-75-7 |
| 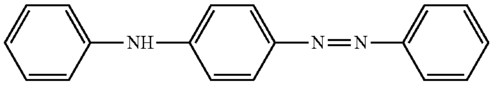 [SMILES: c1ccc(N=Nc2ccc(Nc3ccccc3)cc2)cc1] | | | |
| 4-Diazodiphenylamine Sulfate | TCl | D0141 | 4477-28-5 |
| 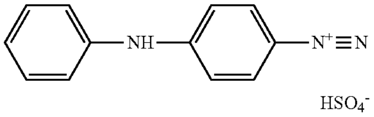 | | | |
| Acid Orange 5 | TCl | A0576 | 554-73-4 |
| 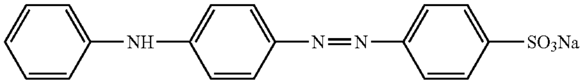 | | | |
| N-(2-Amino-4-chlorophenyl)anthranilic acid | Sigma-Aldrich | 153230 | 67990-66-3 |
| 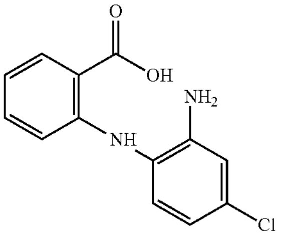 [SMILES: Nc1cc(Cl)ccc1Nc1ccccc1C(=O)O] | | | |
| N-Phenyl-o-phenylenediamine | Sigma-Aldrich | P28352 | 534-85-0 |
| 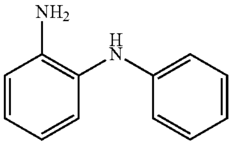 | | | |

TABLE 2-continued

| Compound name | Manufacturer | Product code | CAS |
|---|---|---|---|
| Acid Yellow 36 | TCI | M0490 | 587-98-4 |
| 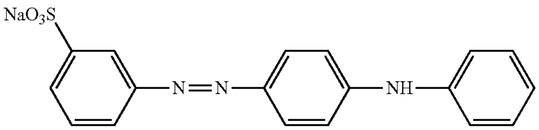 | | | |
| 2-nitro-4-aminodiphenylamine | Sigma-Aldrich | CDS013636 | 2784-89-6 |
| 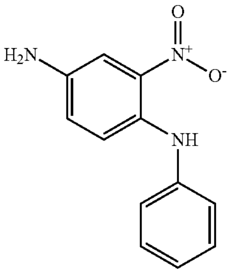 [SMILES: Nc1ccc(Nc2ccccc2)c([N+](=O)[O-])c1] | | | |
| Disperse Yellow 9 | Sigma-Aldrich | 38464 | 6373-73-5 |
| 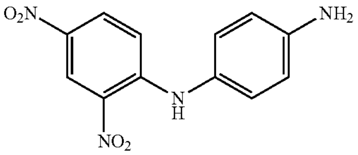 | | | |
| N-(4-Chlorophenyl)-1,2-phenylenediamine | Sigma-Aldrich | 327522 | 68817-71-0 |
| 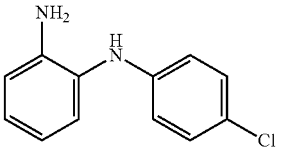 [SMILES: Nc1ccccc1Nc1ccc(Cl)cc1] | | | |
| N-Methyl-N′-phenyl-p-phenylenediamine | NARD institute, Ltd. | Contract synthesis | |
| 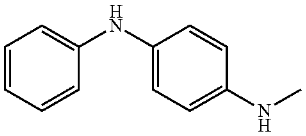 | | | |
| N-Ethyl-N′-phenyl-p-phenylenediamine | NARD institute, Ltd. | Contract synthesis | |
| 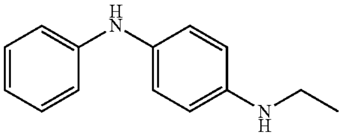 | | | |
| N-Isopropyl-N′-(4-aminophenyl)-p-phenylenediamine | NARD institute, Ltd. | Contract synthesis | |
| 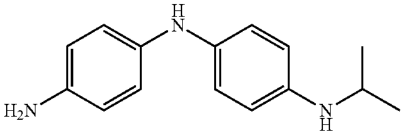 | | | |

TABLE 2-continued

| Compound name | Manufacturer | Product code | CAS |
|---|---|---|---|
| 2-Amino-4-isopropylamino-diphenylamine 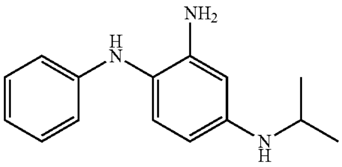 | NARD institute, Ltd. | Contract synthesis | |
| N-Isopropyl-N'-(4-hydroxyphenyl)-p-phenylenediamine 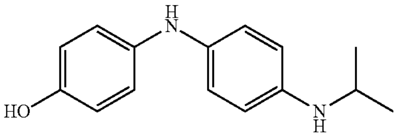 | NARD institute, Ltd. | Contract synthesis | |
| N,N'-Di-2-naphthyl-1,4-phenylenediamine 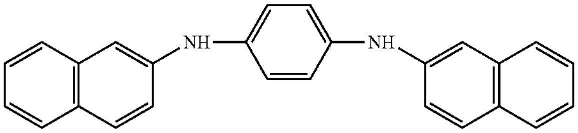 [SMILES: c1ccc2cc(Nc3ccc(Nc4ccc5ccccc5c4)cc3)ccc2c1] | TCl | D0812 | 93-46-9 |
| 5-Sulfo-4'-diethylamino-2,2'-dihydroxyazobenzene 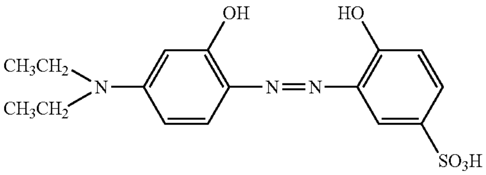 | TCl | S0128 | 1563-01-5 |
| Alizarin Cyanin Green F 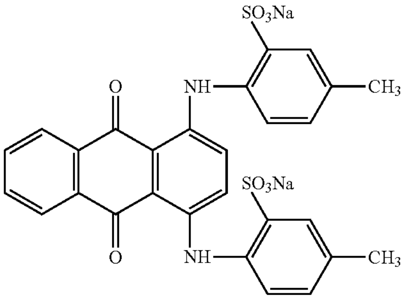 | TCl | A0610 | 4403-90-1 |
| Alphamine Red R Base 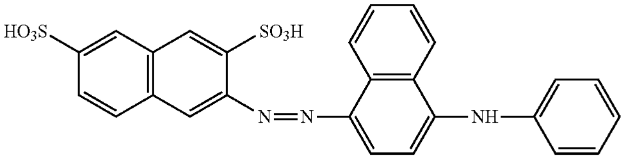 [SMILES: O=S(=O)(O)c1ccc2cc(N=Nc3ccc(Nc4ccccc4)c4ccccc34)c(S(=O)(=O)O)cc2c1] | TCl | A0474 | 57322-42-6 |

TABLE 2-continued

| Compound name | Manufacturer | Product code | CAS |
|---|---|---|---|
| Crocein scarlet 3B | TCI | C0531 | 5413-75-2 |
| 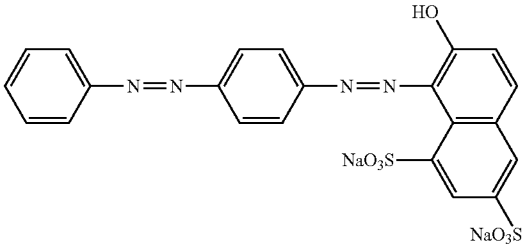 | | | |
| 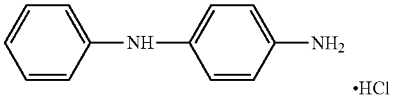 [SMILES: Nc1ccc(Nc2ccccc2)cc1 ; Cl] | TCI | P0189 | 2198-59-6 |

Example 4. Electrochemical Evaluation Using the Phenylenediamine Type Compound FAD-dependent GDH and three phenylenediamine type compounds (IPPD, DPPD, and 6PPD) were used to perform cyclic voltammetry using a printed electrode.

More specifically, a round carbon electrode (manufactured by BioDevice Technology, Ltd., DEP-Chip EP-PP) in which a carbon working electrode (2.64 $mm^2$) and a silver/silver chloride reference electrode were printed was connected to ALS electrochemical analyzer 814D (manufactured by BAS Inc.) using a dedicated connector. The electrode was loaded with 2 μl of a 2000 U/ml FADGDH-AA (manufactured by Kikkoman Biochemifa Company, product No. 60100) solution, 8 μl of a 50 mM potassium phosphate buffer solution (pH 7.0) containing 1.5 M potassium chloride, and 10 μl of an aqueous solution containing IPPD in 10% ethanol. The final concentration of IPPD was set to 2.5 μM. Then, cyclic voltammetry was performed by sweeping voltage in the range from −200 mV to 400 mV (vs. Ag/AgCl). The sweep rate was set to 10 mV/sec. Subsequently, a glucose solution was added with a final concentration of 200 mM, and cyclic voltammetry was performed in the same manner.

Figure 8:
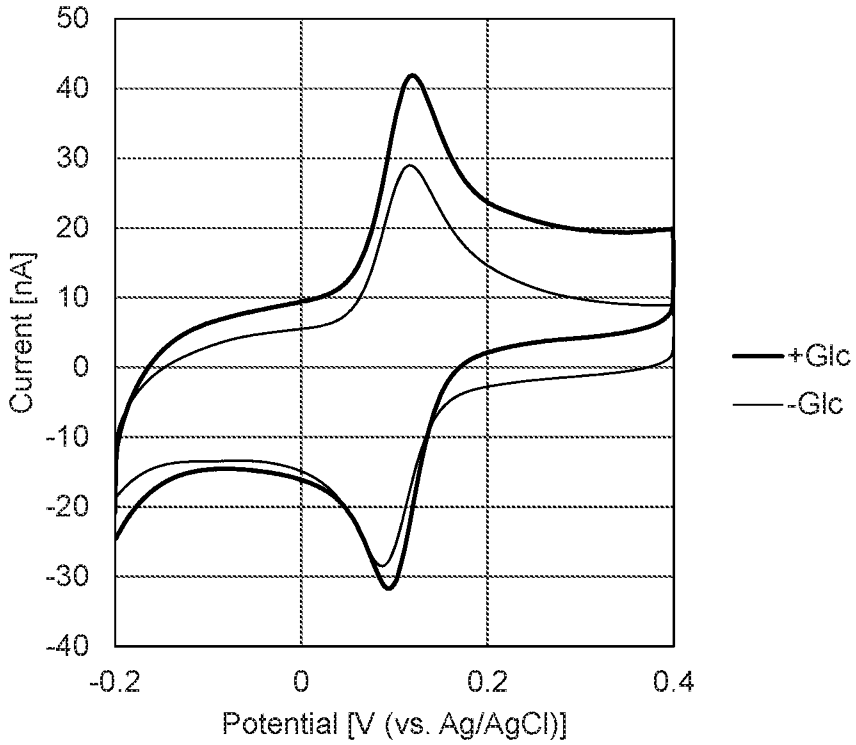
FIG. 8 shows a cyclic voltammogram obtained using IPPD.

A cyclic voltammogram at the time of measurement is shown in FIG. 8. A response current was observed for glucose, indicating that IPPD functions as a mediator.

Subsequently, SCREEN-PRINTED ELECTRODES (manufactured by Metrohm Dropsens, S.L., product No. DRP-110) onto which a carbon working electrode (12.6 $mm^2$) and a silver/silver chloride reference electrode were printed were connected to ALS electrochemical analyzer 814D (manufactured by BAS Inc.) using a dedicated connector (manufactured by Metrohm Dropsens, S.L., DRP-CAC). The electrode was loaded with 5 μl of a 2000 U/ml Glucose Dehydrogenase (FAD-dependent) (manufactured by BBI Solutions, Product Code: GLD3; hereinafter, referred to as GLD3) solution, 20 μl of a 50 mM potassium phosphate buffer solution (pH 7.0) containing 1.5 M potassium chloride, and 25 μl of an aqueous solution containing the phenylenediamine type compound in 10% ethanol. The final concentration of the compound was set to 2.5 M for IPPD and 0.5 M for DPPD and 6PPD. Then, cyclic voltammetry was performed by sweeping voltage in the range from −200 mV to 400 mV (vs. Ag/AgCl). The sweep rate was set to 30 mV/sec. Subsequently, a glucose solution was added with various final concentrations, and cyclic voltammetry was performed in the same manner. Further, cyclic voltammetry was performed as a control experiment in the same manner as above under conditions with no phenylenediamine type compound.

Figure 9:
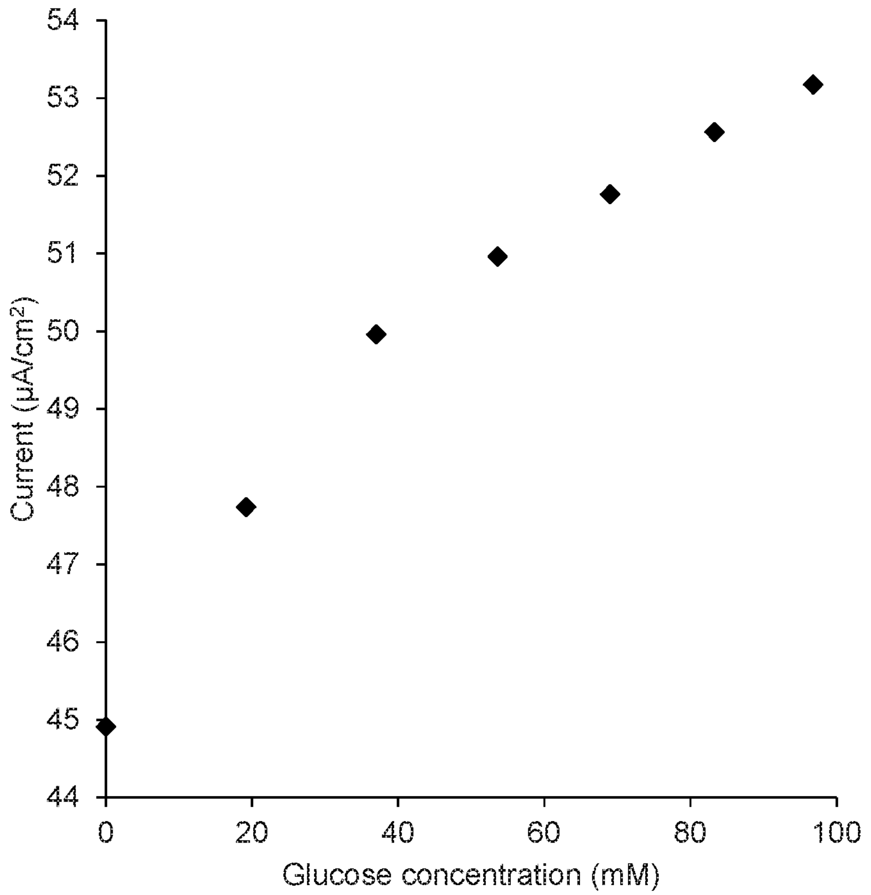
FIG. 9 shows the relationship between the final glucose concentration and the oxidation current value at 300 mV when IPPD was used.
Figure 10:
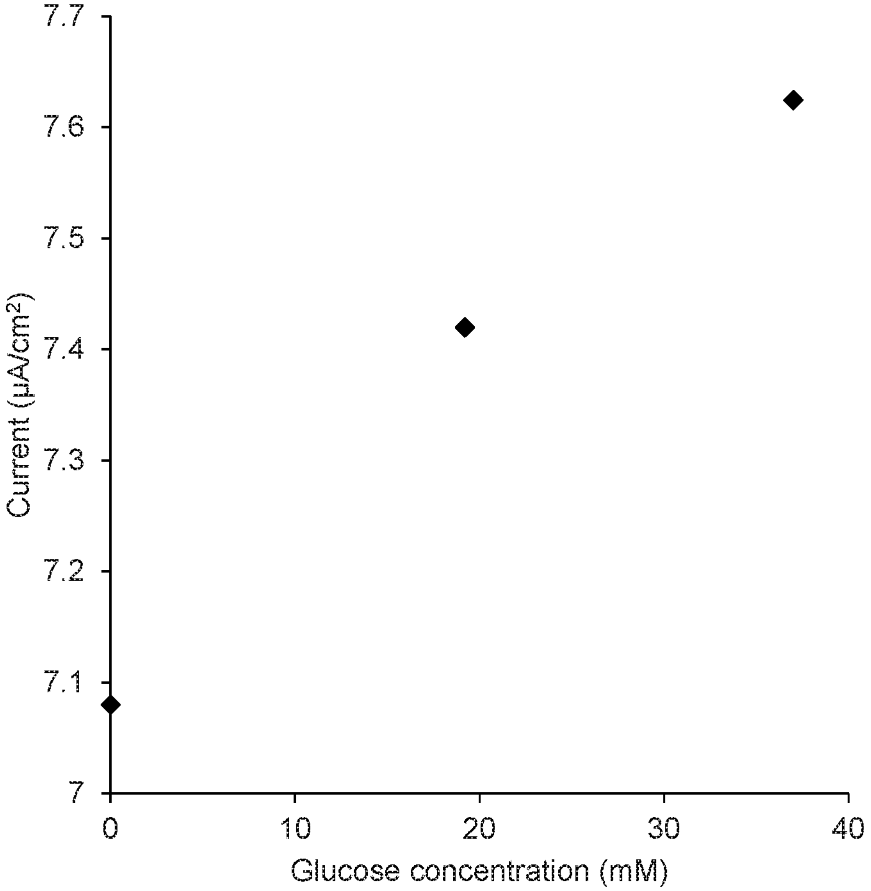
FIG. 10 shows the relationship between the final glucose concentration and the oxidation current value at 300 mV when DPPD was used.
Figure 11:
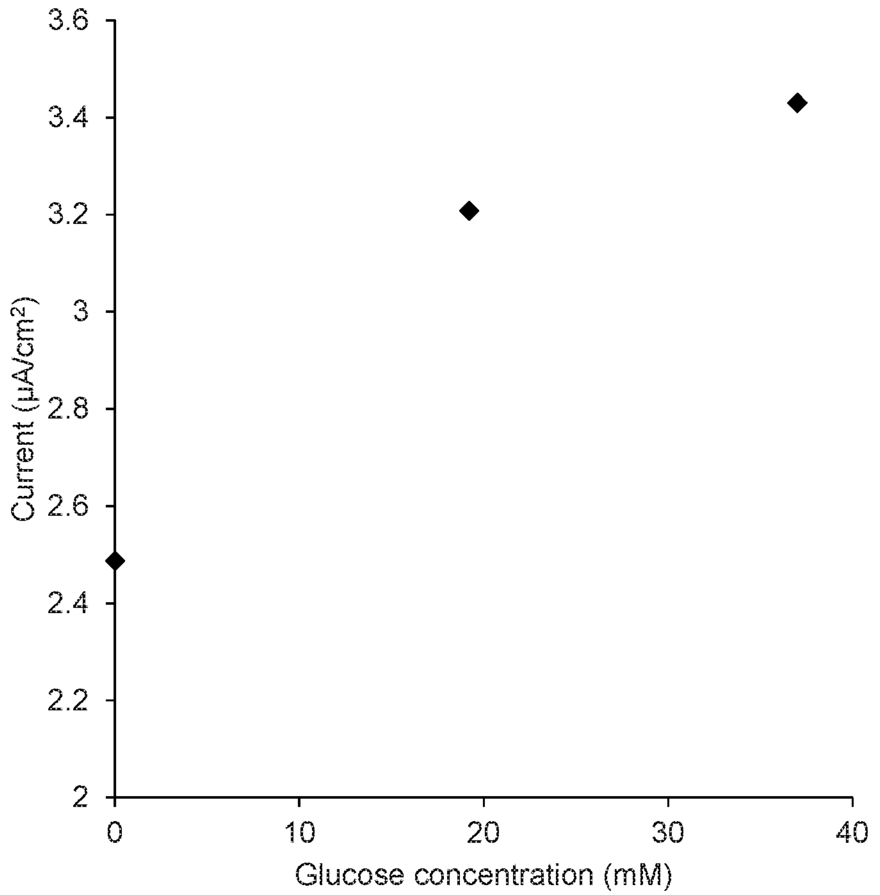
FIG. 11 shows the relationship between the final glucose concentration and the oxidation current value at 300 mV when 6PPD was used.

A plot of the relationship between the final glucose concentration and the oxidation current value at 300 mV when IPPD, DPPD, and 6PPD were used is shown in FIGS. 9, 10, and 11, respectively. When any of the compounds IPPD, DPPD, and 6PPD were used, response current was observed for glucose. On the other hand, no response current was observed when these compounds were not included, indicating that all of IPPD, DPPD, and 6PPD function as a mediator. This indicated that these compounds can also be utilized as an anode electrode.

Figure 12:
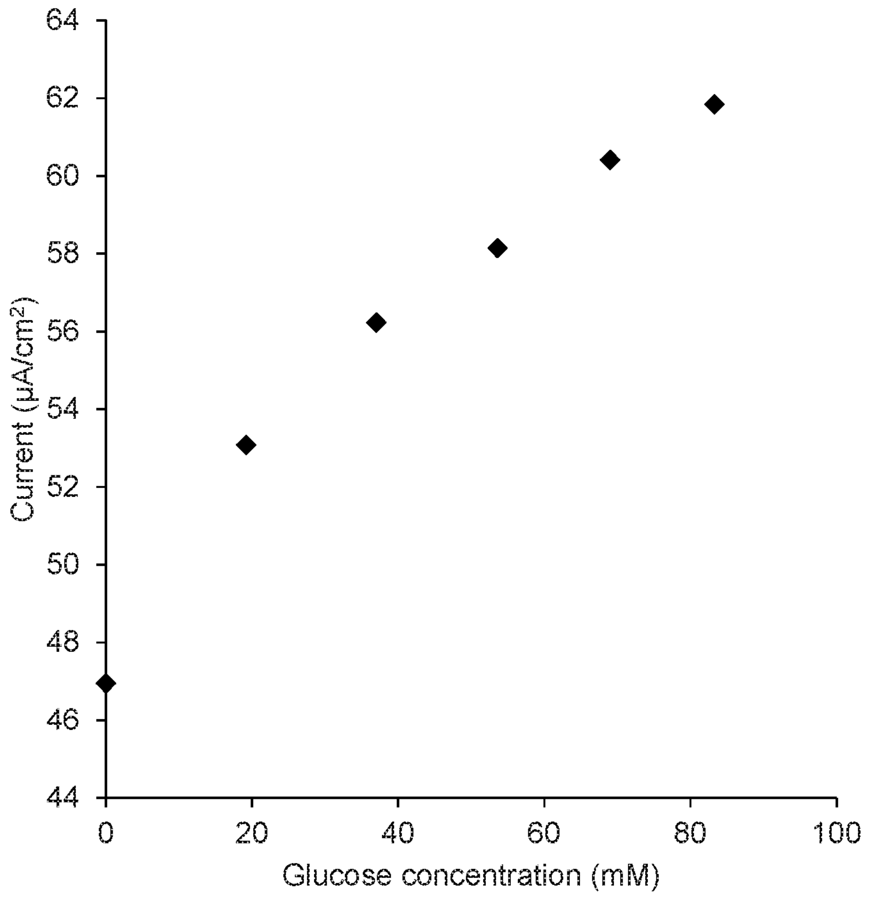
FIG. 12 shows the relationship between the final glucose concentration and the oxidation current value at 300 mV when FADGDH-AA and IPPD were used.
Figure 13:
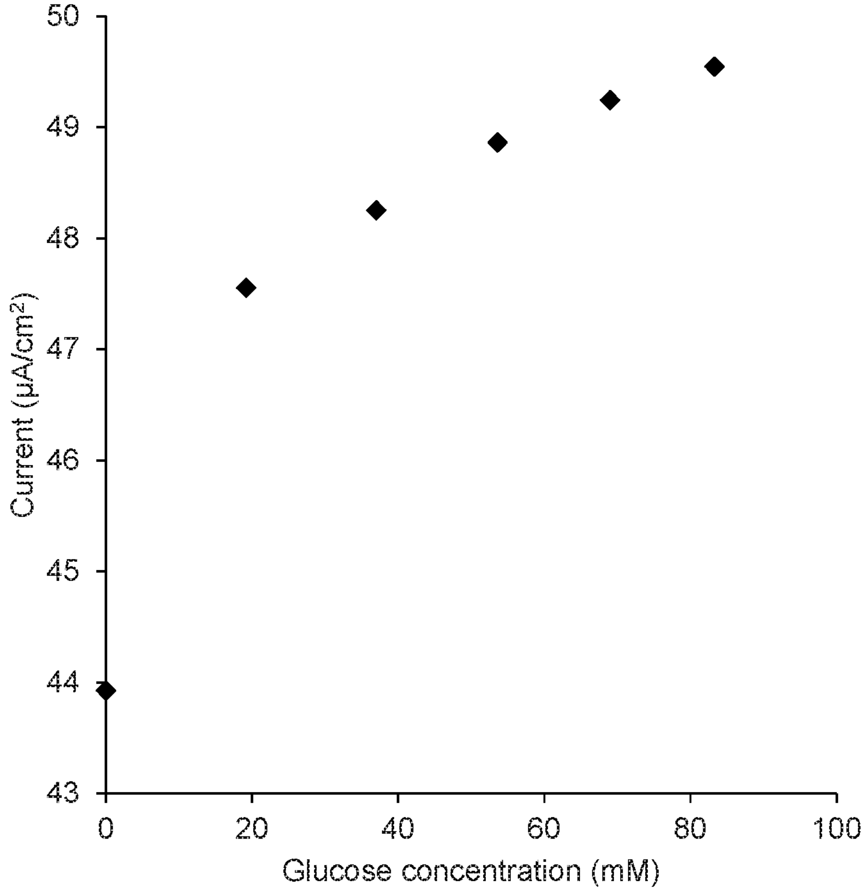
FIG. 13 shows the relationship between the final glucose concentration and the oxidation current value at 300 mV when GLD1 and IPPD were used.

Subsequently, FADGDH-AA (manufactured by Kikkoman Biochemifa Company, product No. 60100) or Glucose Dehydrogenase (FAD-dependent) (manufactured by BBI Solutions, Product Code: GLD1; hereinafter, referred to as GLD1) and IPPD were mixed, and cyclic voltammetry was performed by sweeping voltage in the range from −200 mV to 400 mV (vs. Ag/AgCl) in the same manner as above. However, the final concentration of IPPD was set to 5 μM for the combination with FADGDH-AA and 2.5 μM for the combination with GLD1. The results are shown in FIGS. 12 and 13. A response current was observed for glucose only when IPPD was added, demonstrating that IPPD functions as a mediator. This indicated that the compound can also be utilized as an anode electrode.

Figure 14:
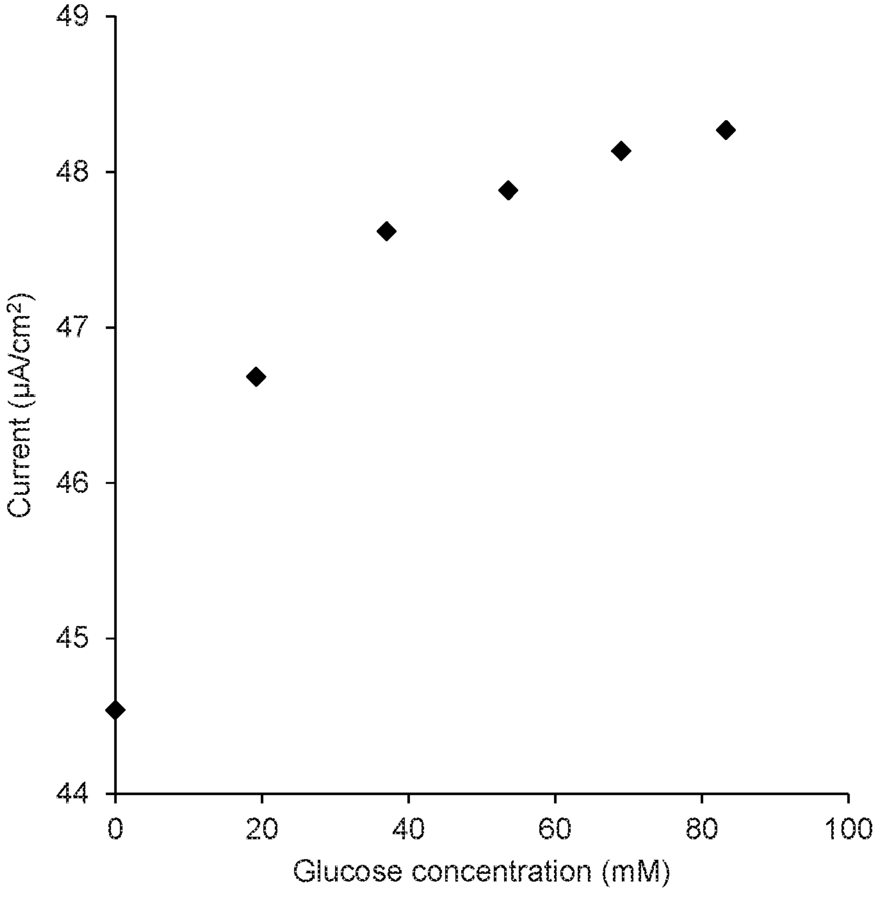
FIG. 14 shows the relationship between the final glucose concentration and the oxidation current value at 300 mV when GOD and IPPD were used.

Subsequently, GOD from *A. niger* Type X-S (manufactured by Sigma-Aldrich Co. LLC, product No. G7141; hereinafter, referred to as GOD) and IPPD were mixed, and cyclic voltammetry was performed in the same manner as above. The results are shown in FIG. 14. A response current was observed for glucose only when IPPD was added, demonstrating that IPPD functions as a mediator. This indicated that the compound can also be utilized as an anode electrode.

Example 5. Stability Test of an Electrode onto which the Compound of the Present Invention and GDH were Immobilized FAD-dependent GDH and N,N'-diphenyl-1,4-phenylenediamine (DPPD, manufactured by Tokyo Chemical Industry Co., Ltd., product code: D0609) were used to carry out cyclic voltammetry (CV) using a printed electrode. More specifically, first, DPPD was adsorbed onto SCREEN-PRINTED ELECTRODES (manufactured by Metrohm Dropsens, S.L., product No. DRP-C110) by the same procedures as in Example 2 and the electrode was washed with ultrapure water and then dried in air. Then, the electrode was coated with 3 μl of a 4 mg/ml FADGDH-AA (manufactured by Kikkoman Biochemifa Company, product No. 60100) solution and dried in air again. Subsequently, the electrode was exposed to steam of a 25% glutaraldehyde solution (manufactured by FUJIFILM Wako Pure Chemical Corp., Wako 1st Grade, product No. 079-00533) for 30 minutes and then, the electrode was washed with pure water to prepare a DPPD/GDH-immobilized electrode. This electrode was connected to ALS electrochemical analyzer 814D (manufactured by BAS Inc.) using a dedicated connector (manufactured by Metrohm Dropsens, S.L., DRP-CAC), and dipped in 10 ml of a 20 mM potassium phosphate buffer solution (pH 7.0) containing glucose having a final concentration of 100 mM. The printed electrode was used as a working electrode, a silver/silver chloride electrode (manufactured by BAS Inc.) was used as a reference electrode, and a platinum electrode (manufactured by BAS Inc.) was used as a counter electrode and the solution was stirred at 750 rpm, and while stirring CV was performed by sweeping voltage in the range from −200 mV to +400 mV (vs. Ag/AgCl). The sweep rate was set to 30 mV/sec. Subsequently, the electrode was taken out of the solution, washed with ultrapure water, and then dipped in a fresh measurement solution having the same composition as above. Similar measurement was repetitively carried out a total of three times. The measurement value of oxidation current in the third CV at +150 mV differed by 149 nA between the solution containing glucose and a blank solution containing no glucose. The response current was higher as compared with the blank, indicating that DPPD functions as an electron migration promoter. As a result of comparing the first or second CV with the third CV, the current value hardly changed if any, indicating that DPPD and GDH are stably immobilized to an electrode without being dissociated into the solution.

Comparative Example (Methylene Blue)

When methylene blue (MB) already known as a mediator was used instead of the compound of the present invention, no glucose-dependent response current was observed. On the other hand, in a test system using FADGDH-AA and MB added into an electrolyte solution, glucose-dependent response current was confirmed. These results indicated that MB is detached in an electrode preparation step and is not adsorbed onto the electrode.

Comparative Example (1-methoxy-5-methylphenazinium methyl sulfate)

A similar test was conducted using 1-methoxy-5-methylphenazinium methyl sulfate (mPMS) already known as a mediator, as in MB. The measurement value of oxidation current in the third CV at +150 mV hardly differed between the solution containing glucose and a blank solution containing no glucose. The value was much lower compared to the case of using DPPD. This indicates that mPMS was easily detached from the electrode and diffused into the solution.

Example 6. Other Oxidoreductases

Subsequently, Fructosyl-peptide Oxidase (FPOX-CE) (manufactured by Kikkoman Biochemifa Company, product No. 60123; hereinafter, referred to as FPOX-CE) and IPPD were used to perform chronoamperometry with a printed electrode. More specifically, the electrode was loaded with 5 of a 0.79 U/ml FPOX-CE solution, 35 μl of a 100 mM potassium phosphate buffer solution (pH 8.0) containing 3 M sodium chloride, and 5 μl of a solution containing 10 ng/μl IPPD in 10% ethanol. Further, 1 of a 9 mM fructosyl glycine solution was added thereto. Then, +250 mV (vs. Ag/AgCl) was applied thereto, and change in response current value was observed for 120 seconds.

Figure 15:
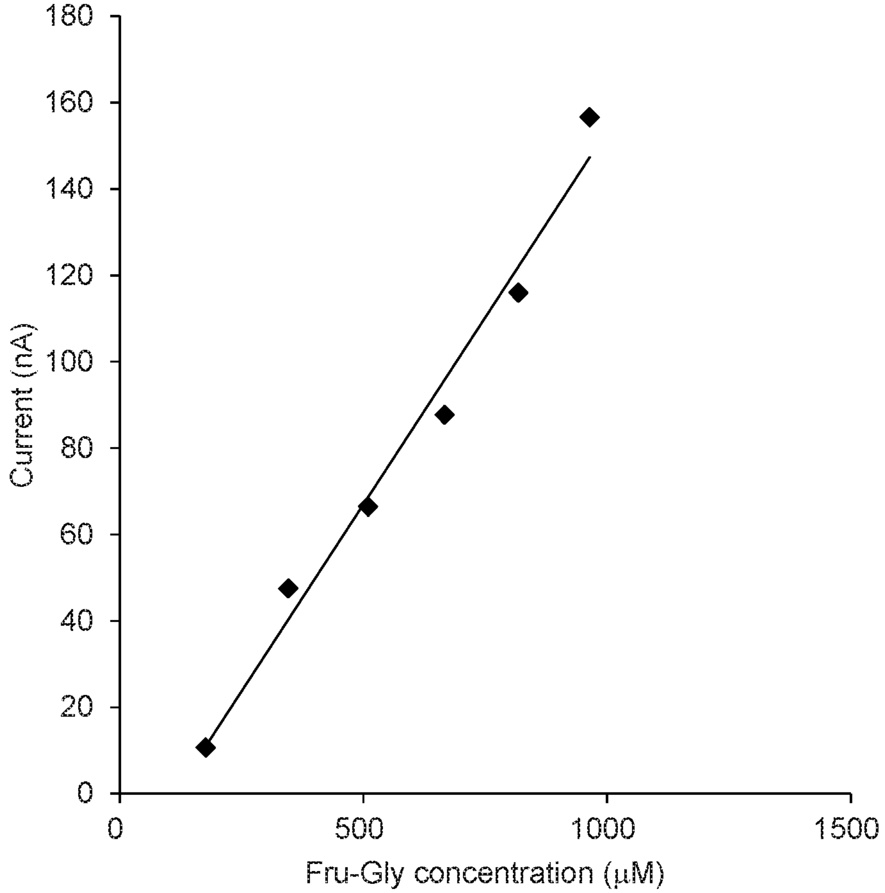
FIG. 15 shows the relationship between the final glucose concentration and the oxidation current value at 300 mV when FPOX-CE IPPD were used.

As a result of recording the value 10 seconds after application, as shown in FIG. 15, the response current value was found to increase as the concentration of fructosyl glycine increased. These results indicated that IPPD functions as a mediator for FPOX-CE as well. This indicated that the compound can also be utilized as an anode electrode.

FADGDH-AA, BGLB, and TDPA were used to perform CV with a printed electrode. More specifically, a compound/GDH-immobilized electrode was prepared by the same procedures as in Example 2 to carry out CV. However, the sweep range of CV was set to from −200 mV to +600 mV (vs. Ag/AgCl) and further, measurement was performed as a control experiment using a solution containing no glucose.

Figure 16:
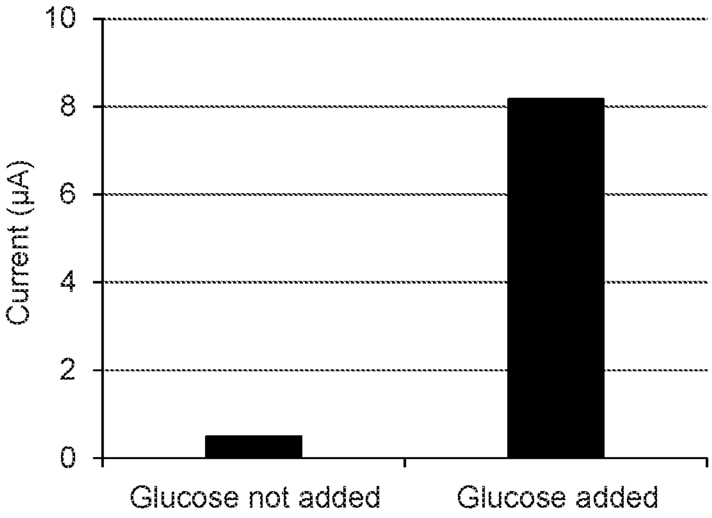
FIG. 16 shows the comparison of an oxidation current value when BGLB was used with FADGDH-AA and +300 mV was applied.
Figure 17:
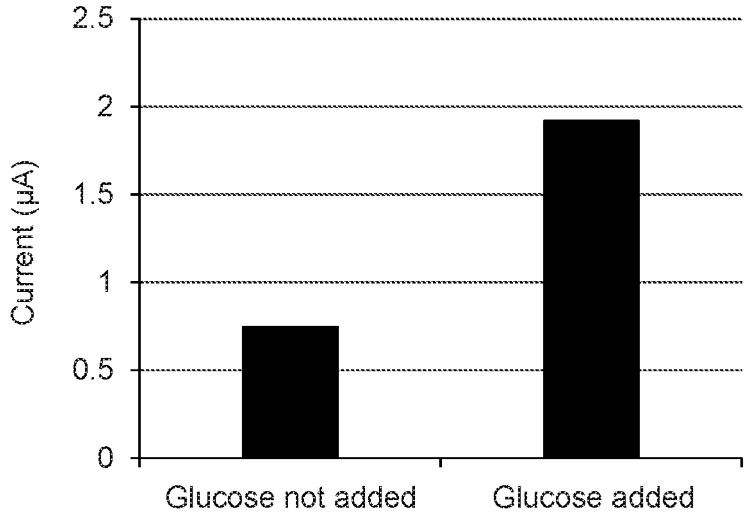
FIG. 17 shows the comparison of an oxidation current value when TDPA was used with FADGDH-AA and +300 mV was applied.

The comparison of the oxidation current value at +300 mV when BGLB and TDPA were used is shown in FIGS. 16 and 17, respectively. When any of the compounds BGLB and TDPA were used, a glucose-dependent response current was observed. This demonstrated that both BGLB and TDPA can be utilized as a mediator for FADGDH-AA.

Subsequently, CV was performed using PQQ-dependent GDH, N-isopropyl-N'-phenyl-1,4-phenylenediamine (IPPD, manufactured by Tokyo Chemical Industry Co., Ltd., product code: P0327) and BGLB. More specifically, printed electrode DRP-C110 was connected to ALS electrochemical analyzer 814D using a dedicated connector (DRP-CAC). 5 μl of a 0.8 mg/ml Glucose dehydrogenase (PQQ-dependent) (manufactured by Toyobo Co., Ltd., product code: GLD-321) solution, 20 μl of a 50 mM potassium phosphate buffer solution (pH 6.8) containing 1.5 M potassium chloride, and 25 μl of a solution containing 5 M compound in 10% ethanol were added dropwise onto the electrode. A solution used for dissolving the enzyme was a 50 mM potassium phosphate buffer solution (pH 6.8) containing 1 mM calcium chloride and 0.1% polyoxyethylene (10) octylphenylether. Then, CV was carried out by sweeping voltage in the range from −200 mV to +400 mV (vs. Ag/AgC). The sweep rate was set to 30 mV/sec. Subsequently, a glucose solution was added with various final concentrations, and CV was carried out in the same manner.

Figure 18:
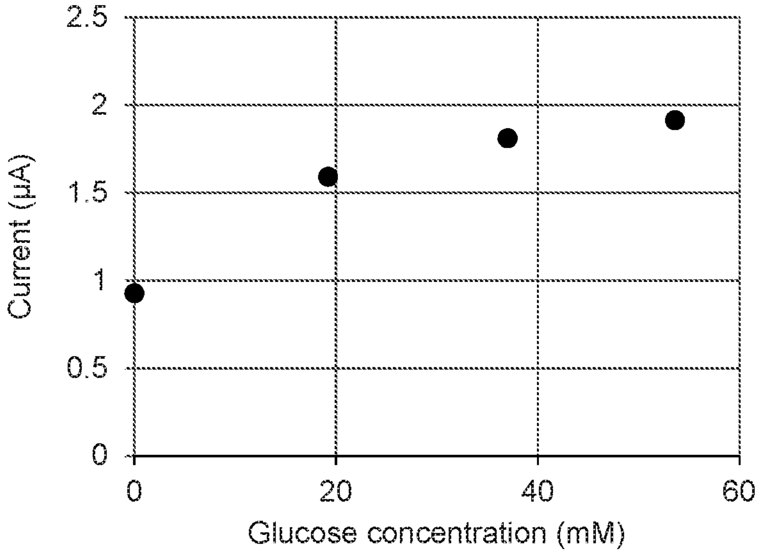
FIG. 18 shows results of plotting the relationship between the final glucose concentration and the oxidation current value at +300 mV using IPPD with PQQ-GDH.
Figure 19:
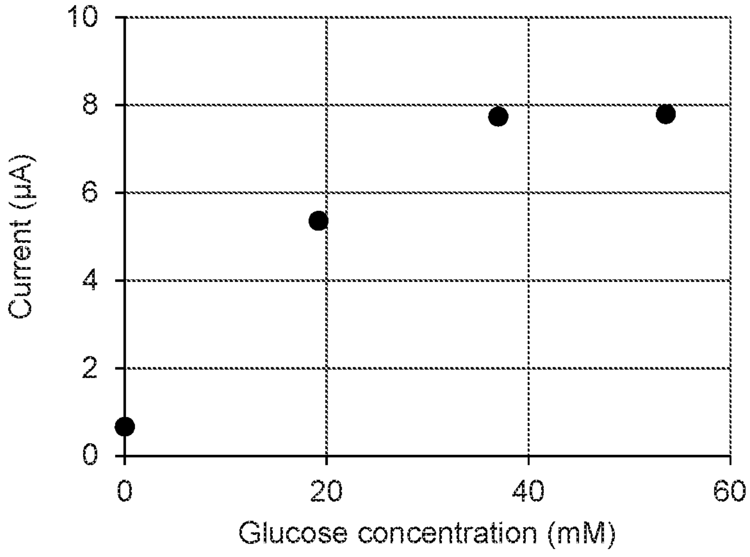
FIG. 19 shows results of plotting the relationship between the final glucose concentration and the oxidation current value at +300 mV using BGLB with PQQ-GDH.

A plot of the relationship between the final glucose concentration and the oxidation current value at +300 mV is shown in FIGS. 18 and 19. When any of the compounds IPPD and BGLB were used, a glucose concentration-dependent current was observed, indicating that these compounds function as mediators for PQQ-dependent GDH.

Subsequently, chronoamperometry was carried out using NAD-dependent GDH and DPPD. More specifically, printed electrode DRP-C110 was connected to ALS electrochemical analyzer 814D using a dedicated connector (DRP-CAC) and 5 μl of a 5 mg/ml Glucose dehydrogenase (NAD(P)-dependent) (manufactured by Toyobo Co., Ltd., product code: GLD-311) solution, 15 μl of a 150 mM potassium phosphate buffer solution (pH 8.0) containing 1.5 M potassium chloride, 5 μl of a 50 mM aqueous NAD solution, and 25 μl of a solution containing 5 M DPPD in 10% ethanol were added dropwise onto the electrode. The solution used for dissolving the enzyme was a 150 mM potassium phosphate buffer solution (pH 8.0). A potential of +150 mV (vs. Ag/AgCl) was applied thereto. After 60 seconds from the start of measurement, 5 μl of a 500 mM glucose solution was added, and change in current was measured. Further, a similar test was conducted as a control experiment using a measurement solution containing no DPPD.

Figure 20:
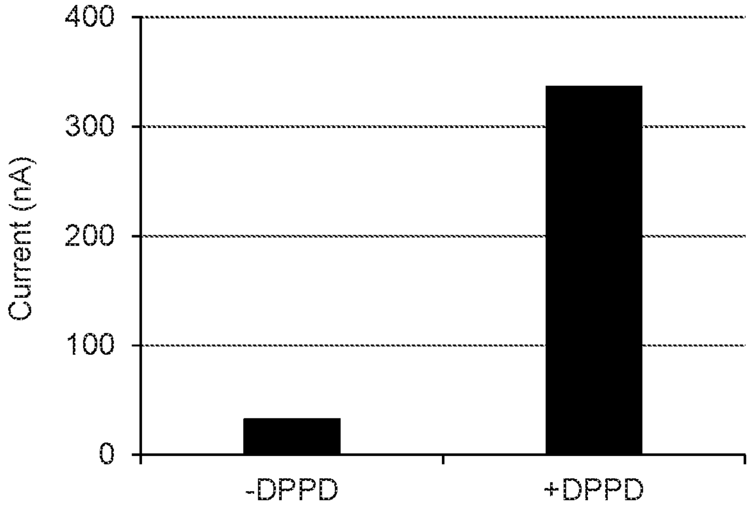
FIG. 20 shows response current between before and after addition of glucose when NAD-GDH was used in the presence or absence of DPPD.

Difference in response current between before and after addition of glucose at the point in time when the current value became constant after addition of the glucose solution is shown in FIG. 20. The current value increased largely by the addition of glucose in the presence of DPPD, whereas response to glucose was hardly observed in the absence of DPPD. This demonstrated that DPPD also functions as a mediator for NAD-dependent GDH.

Subsequently, CV was carried out using lactate oxidase (LOD) and IPPD. More specifically, printed electrode DRP-C110 was connected to ALS electrochemical analyzer 814D using a dedicated connector (DRP-CAC) and 5 μl of a 5 mg/ml Lactate Oxidase (manufactured by Toyobo Co., Ltd., product code: LCO-301) solution, 20 μl of a 1 M potassium phosphate buffer solution (pH 7.0) containing 1.5 M potassium chloride, and 25 μl of a solution containing 5 M IPPD in 10% ethanol were added dropwise onto the electrode. The solution used for dissolving the enzyme was a 1 M potassium phosphate buffer solution (pH 7.0). Then, CV was carried out by sweeping voltage in the range from −200 mV to +400 mV (vs. Ag/AgCl). The sweep rate was set to 30 mV/sec. Subsequently, a lactic acid solution was added with various final concentrations, and CV was carried out in the same manner.

Figure 21:
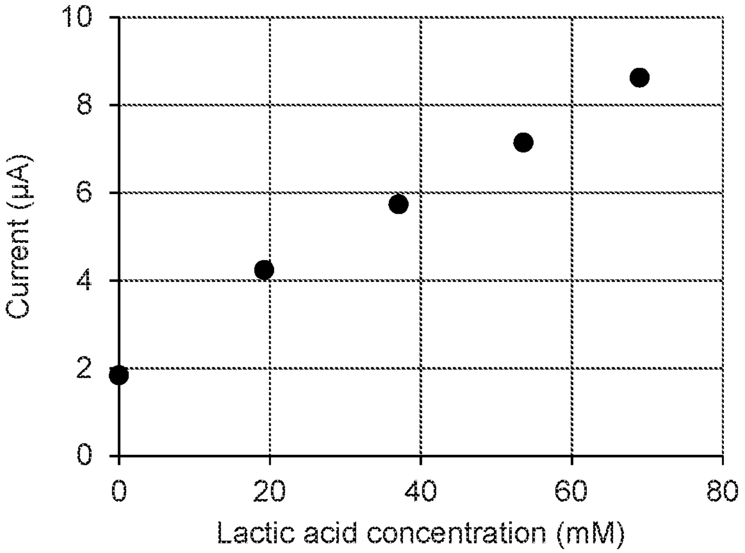
FIG. 21 shows results of plotting the relationship between a final concentration of lactic acid and the oxidation current value at +150 mV using IPPD with LOD.

A plot of the relationship between a final concentration of lactic acid and the oxidation current value at +150 mV is shown in FIG. 21. Increase in lactic acid concentration-dependent response current was seen, indicating that IPPD functions as a mediator for LOD.

Subsequently, CV was carried out using fructose dehydrogenase (FDH) and IPPD. FDH is an enzyme known to be able to transfer electrons directly to an electrode even in the absence of a mediator (i.e., to have the ability to directly transfer electrons) and to allow substrate-dependent response current to be observed even in the absence of a mediator. More specifically, printed electrode DRP-C110 was connected to ALS electrochemical analyzer 814D using a dedicated connector (DRP-CAC) and 5 μl of a 10 mg/ml D-Fructose dehydrogenase (manufactured by Toyobo Co., Ltd., product code: FCD-302) solution, 20 μl of a 150 mM sodium acetate buffer solution (pH 4.5) containing 1.5 M potassium chloride, and 25 μl of a solution containing 5 μM IPPD in 10% ethanol were added dropwise onto the electrode. A solution used for dissolving the enzyme was a 150 mM sodium acetate buffer solution (pH 4.5) containing 0.1% polyoxyethylene (10) octylphenylether. Then, CV was carried out by sweeping voltage in the range from −200 mV to +400 mV (vs. Ag/AgC). The sweep rate was set to 30 mV/sec. Subsequently, a fructose solution was added with various final concentrations, and CV was carried out in the same manner.

Figure 22:
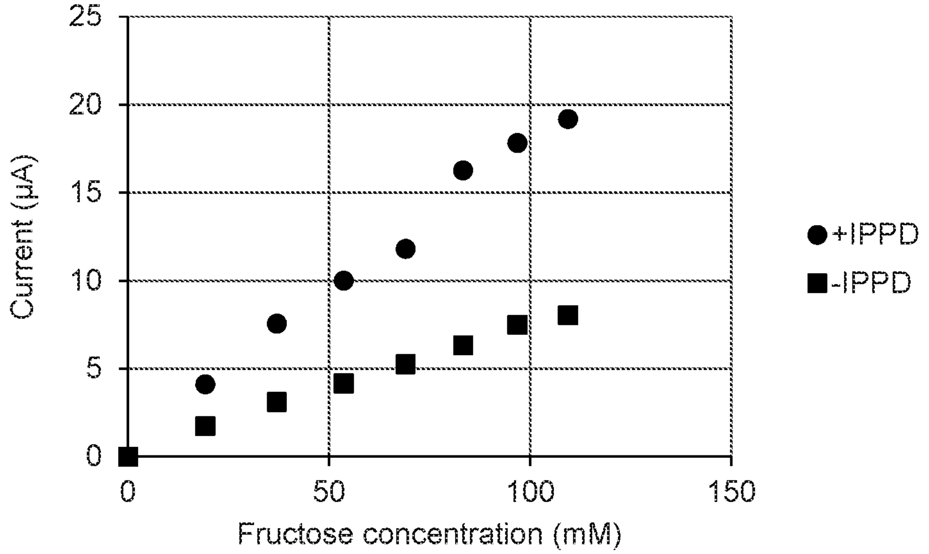
FIG. 22 shows results of plotting the relationship between a final concentration of fructose and the oxidation current value at +100 mV when FDH was used in the presence or absence of IPPD. The current without the addition of fructose was defined as 0.

A plot of the relationship between a final fructose concentration and the oxidation current value at +100 mV is shown in FIG. 22 when current without the addition of fructose was defined as 0. Since FDH has the ability to directly transfer electrons, a fructose-dependent response current is observed even in the absence of IPPD. However, a larger current was observed in the presence of IPPD as compared with in the case where IPPD was non-existent. This indicated that IPPD functions as a mediator even for FDH which has having the ability to directly transfer electrons.

Figure 23:
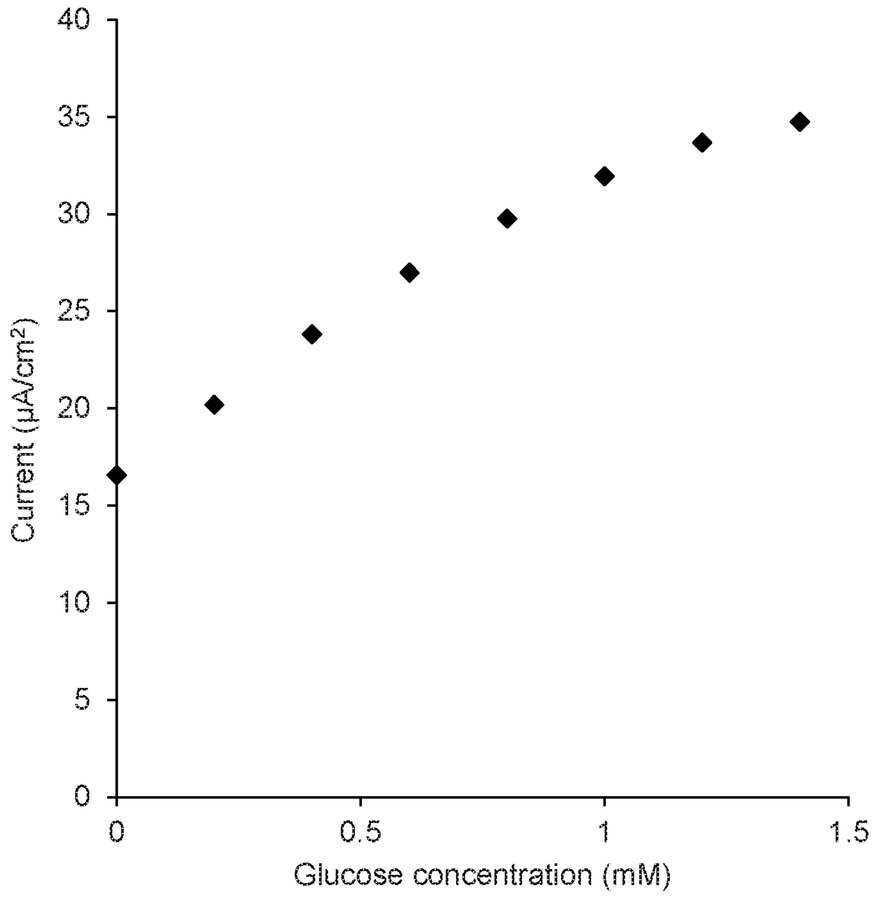
FIG. 23 shows the relationship between the final glucose concentration and the oxidation current value at 200 mV when an electrode onto which IPPD was adsorbed and GDH was immobilized was used.

Example 7. Glucose Measurement Using the Phenylenediamine Type Compound/GDH-Immobilized Sensor SCREEN-PRINTED ELECTRODES (manufactured by Metrohm Dropsens, S.L., product No. DRP-C110) were coated with 3 of 5% polyethylenimine (average molecular weight: 10000) and dried at room temperature. Subsequently, the electrode was coated with 3 of IPPD (dissolved in 10% ethanol) and 30 U of GDH-M2 and dried at room temperature. Finally, the electrode was coated with 1 of 2.5 mg/dl polyethylene glycol diglycidyl ether (average molecular weight: 500) and left standing overnight at 4° C. The obtained electrode was washed with pure water to prepare an IPPD/GDH-immobilized electrode. Next, the IPPD/GDH-immobilized electrode, an Ag/AgCl reference electrode, and a platinum counter electrode were dipped in a 100 mM potassium phosphate buffer solution (pH 7), and CV measurements were performed. The sweep rate was set to 10 mV/sec. 2 M glucose was appropriately added, and the oxidation current value at +200 mV was calculated for each glucose concentration. The results are shown in FIG. 23. The response current value was found to increase as glucose concentration increased. Thus, it is concluded that the glucose concentration can be quantified by measuring glucose having a known concentration and preparing a calibration curve. This also indicated that the compound can be utilized as an anode electrode.

Example 8. Adsorption Confirmation Test Using Electrode Material Other than Carbon A gold electrode (manufactured by BAS Inc., Cat No. 002421), an Ag/AgCl reference electrode, and a platinum counter electrode were dipped in a phosphate buffer solution of pH 7 containing IPPD and GDH-M2, and CV measurement was performed. The sweep rate was set to 10 to 100 mV/sec, and the sweep rate and $I_{Omax}$ and $I_{Rmax}$ were plotted. As a result, the sweep rate and $I_{Omax}$ and $I_{Rmax}$ were confirmed to have a proportional relationship, indicating that IPPD is adsorbed onto a gold electrode.

Similarly, when a platinum electrode (manufactured by BAS Inc., Cat No. 002422) was used instead of the gold electrode, the sweep rate and $I_{Omax}$ and $I_{Rmax}$ were also confirmed to have a proportional relationship, indicating that IPPD is adsorbed onto a platinum electrode.

Example 9. Electrochemical Detection of Compound of Present Invention at Low Concentration Printed electrode DRP-C110 was left standing in a 50 mM potassium phosphate buffer solution containing DPPD diluted into each concentration from 10 pM to 100 nM. A control experiment was also carried out using a solution not comprising any DPPD. The electrode was appropriately left standing for 1 hour to 5 days and then connected to ALS electrochemical analyzer 814D using a dedicated connector (DRP-CAC) and CV was carried out by sweeping voltage in the range from −400 mV to +200 mV (vs. Ag/Ag+) in 10 ml of a 50 mM potassium phosphate buffer solution (pH 6.8)

containing no DPPD and containing FADGDH-AA having a final concentration of 4 mg/ml. The sweep rate was set to 30 mV/sec. Then, 1 ml of a 1 M glucose solution was added, and CV was carried out in the same manner. A value was calculated by subtracting the oxidation current value at +100 mV without the addition of glucose from the oxidation current value at +100 mV.

Figure 24:
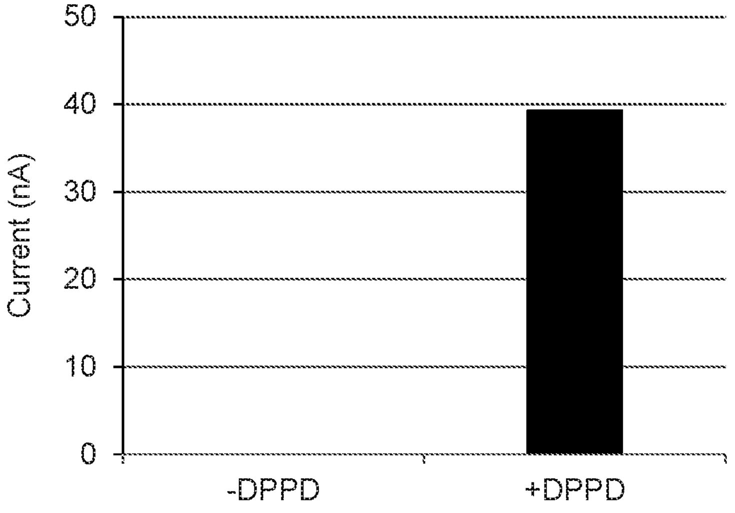
FIG. 24 shows the oxidation current value at +100 mV when an electrode modified using DPPD having a final concentration of 10 pM was placed in a solution containing FADGDH-AA and glucose. The current without the addition of glucose was defined as 0.

The results obtained using the 10 pM DPPD solution are shown in FIG. 24. The current value increased by the addition of glucose, suggesting that the compound is useful as a sensor that can detect DPPD at a concentration as low as 10 pM in this system. No increase in response current was seen by the addition of glucose when the solution containing no DPPD was used. Significant increase in response current was also confirmed by the addition of glucose as compared with without the addition of glucose when 100 pM, 1 nM, 10 nM, or 100 nM DPPD was used in the same manner.

Example 10. Construction of a Fuel Cell

A 5 mm×5 mm carbon cloth (manufactured by TOYO Corp.) was coated with 80 μl of a multilayered carbon nanotube solution in several divided portions and dried at 60° C. The carbon cloth was washed with pure water and then further dried, followed by the adsorptive fixation of IPPD thereto. Subsequently, the carbon cloth was coated with 20 μl of 12 mg/ml FAD-dependent glucose dehydrogenase (GLD1, manufactured by Funakoshi Co., Ltd.) and dried at 25° C. The carbon cloth was exposed to steam of 25% glutaraldehyde for 30 minutes so that GLD1 was immobilized by cross-linking to prepare an anode electrode. Platinum (manufactured by BAS Inc.) was used as a cathode electrode, and dipped, together with the anode electrode and an Ag/AgCl reference electrode, in PBS containing 100 mM D-glucose, and connected to variable resistance and a potentiostat. As a result of performing measurement at an open circuit potential, current of 60 μA/cm2 was observed when connecting 10 kΩ. No current could be observed at the time of connection of 10 kΩ when an electrode without the adsorptive fixation of IPPD was used. Thus, a battery that can generate electricity without the addition of a mediator into a fuel tank can be prepared by using an electrode onto which the phenylenediamine type compound of the present invention is immobilized.

Similarly, a current was generated when a single-layered carbon nanotube was used instead of the multilayered carbon nanotube.

Example 11. Construction of Glucose Sensor Using Compound of Present Invention

Adsorptive fixation was performed to a single-layered carbon nanotube using 1 mg/ml IPPD to prepare a solution. The working electrode of the printed electrode used in Example 2 was coated with 3 μL of this solution, dried, and thoroughly washed with ultrapure water. Subsequently, the electrode was coated with 4 mg/ml GLD1 and dried, and GLD1 was immobilized by cross-linking using glutaraldehyde in the same manner as above. The electrode was washed with ultrapure water and then dipped in PBS. A silver/silver chloride reference electrode and a platinum counter electrode were also dipped therein and chronoamperometry measurement was performed by the application of +250 mV. As a result, a response current of 1.3 μA was observed by the addition of 100 M glucose as compared to the case without the addition of glucose. This suggested that an enzyme sensor can be prepared in the same manner by coating a printed electrode with a carbon-adsorbed solution in advance. A similar enzyme sensor was prepared using ketjen black instead of the single-layered carbon nanotube.

INDUSTRIAL APPLICABILITY

Various electrochemical measurements of batteries, etc. can be performed by using an electrode modifying agent comprising the phenylenediamine type compound of the present invention or an electrode onto which the electrode modifying agent is adsorbed.

All publications, patents and patent applications cited herein are incorporated herein by reference in their entirety.

BRIEF DESCRIPTION OF SEQUENCES

SEQ ID NO: 1: *Mucor prainii*-derived GDH (aa)
SEQ ID NO: 2: *Mucor prainii*-derived GDH (DNA)
SEQ ID NO: 3: MpGDH-M2 (aa)
SEQ ID NO: 4: MpGDH-M2 (DNA)

The invention claimed is:

1. A composition comprising:

an enzyme; and an electrode modifying agent or an electron transfer promoting agent comprising a compound having a property of being adsorbed, without being bound to a polymer or without being polymerized, onto an electrode untreated with an acid, wherein the compound is a compound having a structure of formula I or formula II:

[Formula 1]

(I)

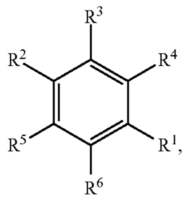

or (II)

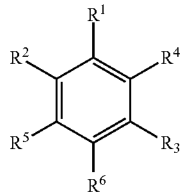

wherein $R^1$ is —$NR^7R^8$, —N═N—$R^9$, or —$N^+$≡N, $R^2$ is —$NR^{10}R^{11}$ or —N═N—$R^{12}$, $R^7$ and $R^8$ are each independently hydrogen, or linear or branched $C_{1-7}$ alkyl, $C_{1-7}$ alkenyl, $C_{1-7}$ alkynyl, $C_{3-9}$ cycloalkyl, phenyl, 1-naphthyl, 2-naphthyl, anthracenyl, phenanthrenyl, acetyl, carboxy, furanylformyl, pyrazolylformyl, 1-methyl-1H-pyrazol-5-ylformyl, 9,9-dimethylfluoren-2-yl, —$N^+$≡N, —N═N-phenyl, benzyl,

[Formula 2]

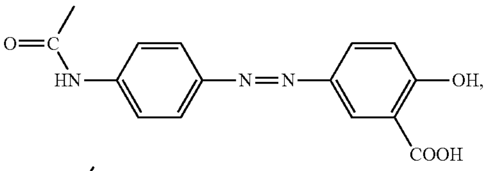

or

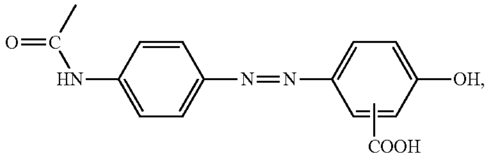

which may optionally be substituted with one or more X or V, $R^{10}$ is hydrogen, or linear or branched $C_{1-7}$ alkyl, $C_{1-7}$ alkenyl, $C_{1-7}$ alkynyl, $C_{3-9}$ cycloalkyl, phenyl, 1-naphthyl, 2-naphthyl, anthracenyl or phenanthrenyl, which may optionally be substituted with one or more X or V, $R^3$, $R^4$, $R^5$ and Re are each independently hydrogen, or linear or branched $C_{1-7}$ alkyl, $C_{1-7}$ alkenyl, $C_{1-7}$ alkynyl, $C_{1-7}$ alkoxy, halo, nitro, cyano, carboxy, sulfo, hydroxy or amino, which may optionally be substituted with one or more Y, or $R^3$ and $R^4$, or $R^5$ and Re, together with the benzene ring containing these moieties, form a benzene ring, or

[Formula 3]

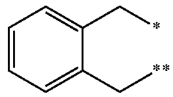

or

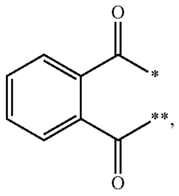

which may optionally be substituted with one or more oxo, X or W, wherein * is bonded to the carbon atom bonded to $R^3$, and ** is bonded to the carbon atom bonded to $R^4$, or * is bonded to the carbon atom bonded to $R^5$, and ** is bonded to the carbon atom bonded to $R^6$, $R^{11}$ is selected from the group consisting of phenyl, 1-naphthyl, 2-naphthyl, anthracenyl and phenanthrenyl, which may optionally be substituted with one or more X or Z, $R^9$ is selected from the group consisting of hydrogen, and phenyl, 1-naphthyl, 2-naphthyl, anthracenyl and phenanthrenyl, which may optionally be substituted with one or more X, $R^{12}$ is selected from the group consisting of phenyl, 1-naphthyl, 2-naphthyl, anthracenyl, phenanthrenyl, and

[Formula 4]

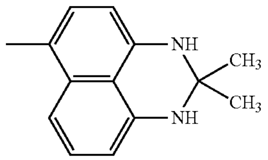

which may optionally be substituted with one or more X, W, isothiocyanate, or halosulfonyl, wherein V is —O-acryloyl, acetylamino, or phenyl, which may optionally be substituted with $C_{1-7}$ alkyl, W is D- or L-alanylsulfonyl, D- or L-valylsulfonyl, D- or L-leucylsulfonyl, D- or L-methionylsulfonyl, D- or L-prolylsulfonyl, D- or L-tryptophylsulfonyl, D- or L-glycylsulfonyl, D- or L-cysteinylsulfonyl, D- or L-isoleucylsulfonyl, D- or L-phenylalanylsulfonyl, D- or L-tyrosylsulfonyl, D- or L-serylsulfonyl, D- or L-threonylsulfonyl, D- or L-asparaginylsulfonyl, D- or L-glutamylsulfonyl, D- or L-arginylsulfonyl, D- or L-histidylsulfonyl, D- or L-lysylsulfonyl, D- or L-aspartylsulfonyl, D- or L-glutaminylsulfonyl, -C(═O)—O-succinimidyl, acetyl, trifluoroacetyl, benzoylamino, —N═N-phenyl, phenylamino, or diaminophenylazophenyl, which may optionally be substituted with one or more amino, C1-7 alkyl, or aminoalkyl, or phenylazo, which may optionally be substituted with one or more X, naphthylazo, which may optionally be substituted with one or more Y, acetylamino,

[Formula 5]

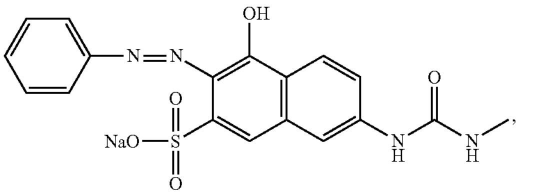

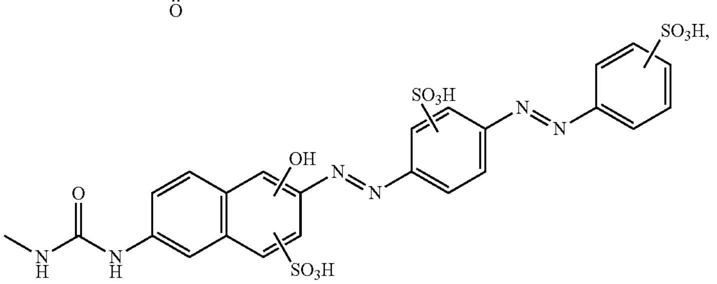

or

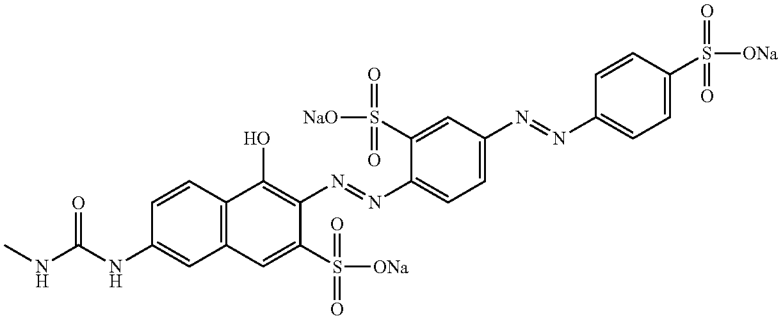

X is linear or branched $C_{1-7}$ alkyl, $C_{1-7}$ alkenyl, $C_{1-7}$ alkynyl, $C_{1-7}$ alkoxy, halo, hydroxy, nitro, carboxy, cyano, sulfo, amino or alkylamino, which may optionally be substituted with one or more substituents selected from the group consisting of halo, amino, cyano, carboxy, carbonyl, alkoxy, alkylamino, nitroso, nitro and sulfo, Y is selected from the group consisting of halo, amino, cyano, carboxy, carbonyl, hydroxy, alkoxy and sulfo, and Z is $—SO_2—CH═CH_2$, $—SO_2—C_2H_4—O—SO_3H$, or 4,6-dichlorotriazin-2-ylamino, or a salt, an anhydride or a solvate thereof, wherein the compound is neither N-methyl-N-phenyl-1,4-phenylenediamine nor N-methyl-N-(3-methoxyphenyl)-1,4-phenylenediamine, and wherein the compound is neither

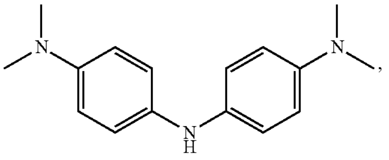

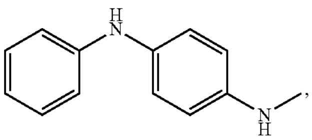

nor

-continued

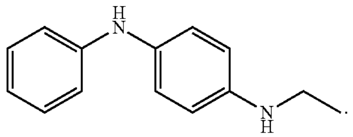

2. The composition according to claim 1, wherein the compound is selected from the group consisting of

[Formula 9]

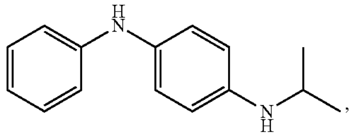

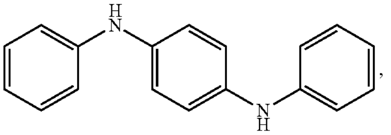

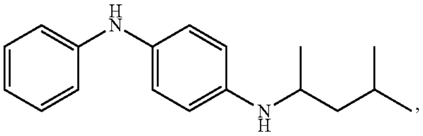

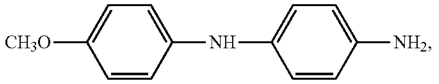

-continued
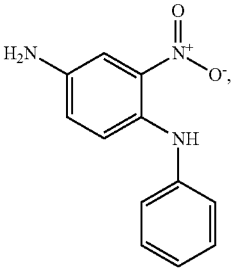
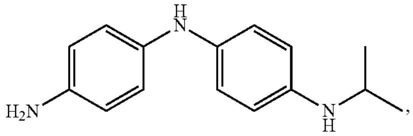
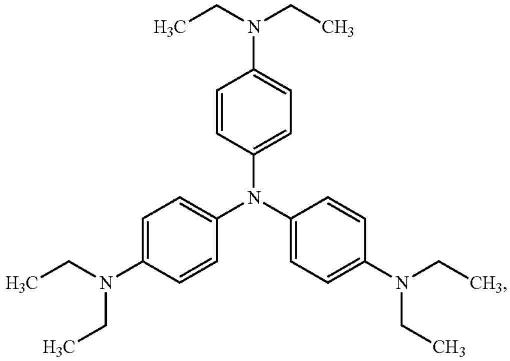
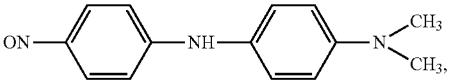
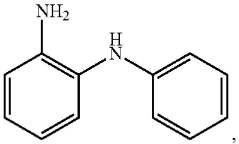
,
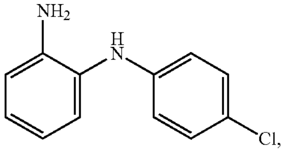
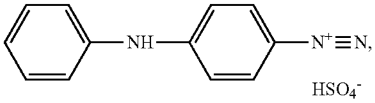
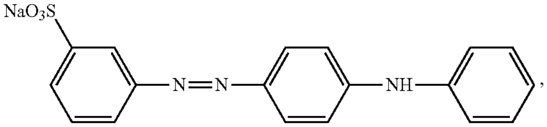
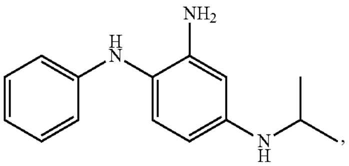
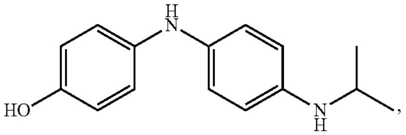
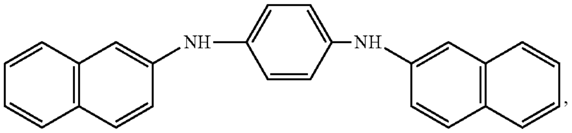
-continued
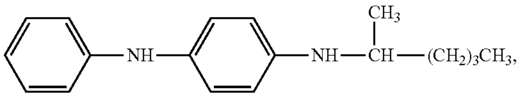
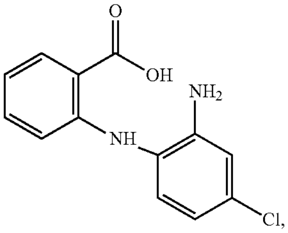
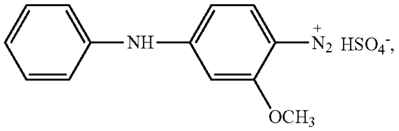
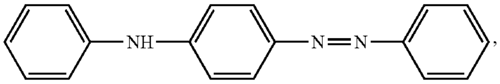
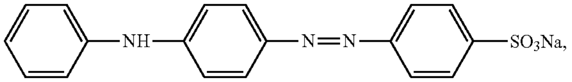
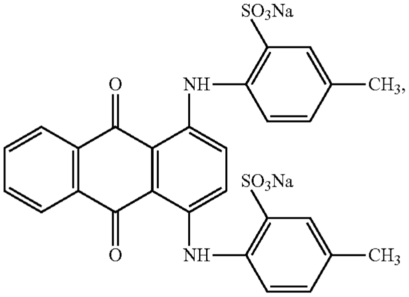
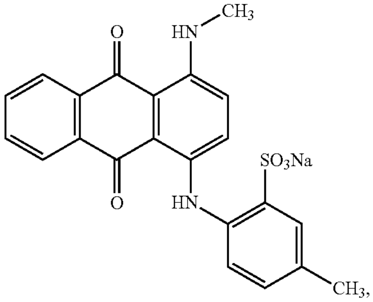
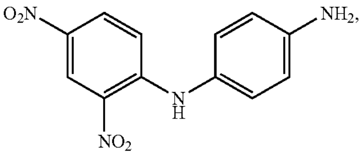
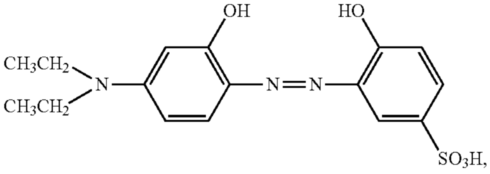
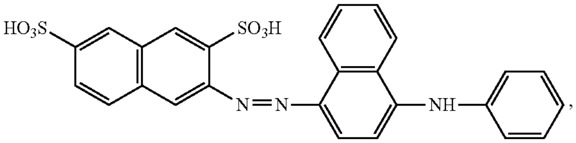

-continued

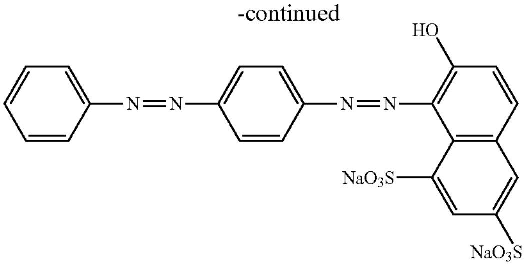

and

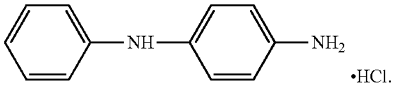

3. The composition according to claim 1, wherein the enzyme is an oxidoreductase.

4. A composition comprising:

an enzyme; and an electrode modifying agent or an electron transfer promoting agent comprising a compound having a property of being adsorbed, without being bound to a polymer or without being polymerized, onto an electrode untreated with an acid, wherein the compound is a compound having a structure of formula Ia or IIa:

[Formula 6]

(Ia))

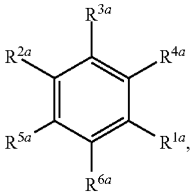

or (IIa)

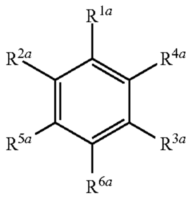

wherein $R^{1a}$ is —$NR^{7a}R^{8a}$, —N═N—$R^{9a}$, or —$N^{+}$≡N, $R^{2a}$ is —$NR^{10a}R^{11a}$, or —N═N—$R^{12a}$, $R^{7a}$ and $R^{8a}$ are each independently hydrogen, or linear or branched $C_{1-6}$ alkyl, $C_{1-6}$ alkenyl, $C_{1-6}$ alkynyl, $C_{3-9}$ cycloalkyl, phenyl, 1-naphthyl, 2-naphthyl, anthracenyl, or phenanthrenyl, which may optionally be substituted with one or more Xa, $R^{10}$ is hydrogen, or linear or branched $C_{1-6}$ alkyl, $C_{1-6}$ alkenyl, $C_{1-6}$ alkynyl, $C_{3-9}$ cycloalkyl, phenyl, 1-naphthyl, 2-naphthyl, anthracenyl or phenanthrenyl, which may optionally be substituted with one or more Xa, $R^{3a}$, $R^{4a}$, $R^{5a}$ and $R^{6a}$ are each independently hydrogen, or linear or branched $C_{1-6}$ alkyl, $C_{1-6}$ alkenyl, $C_{1-6}$ alkynyl, $C_{1-6}$ alkoxy, halo, nitro, cyano, carboxy, sulfo, hydroxy or amino, which may optionally be substituted with one or more Y, or $R^{3a}$ and $R^{4a}$, or $R^{5a}$ and $R^{6a}$ form a benzene ring, or

[Formula 7]

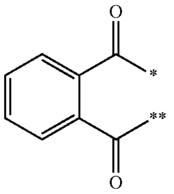

wherein * is bonded to the carbon atom bonded to $R^{3a}$, and ** is bonded to the carbon atom bonded to $R^{4a}$, or * is bonded to the carbon atom bonded to $R^{5a}$, and ** is bonded to the carbon atom bonded to $R^{6a}$, $R^{11a}$ is selected from the group consisting of phenyl, 1-naphthyl, 2-naphthyl, anthracenyl and phenanthrenyl, which may optionally be substituted with one or more Xa, $R^{9a}$ and $R^{12a}$ are each independently selected from the group consisting of hydrogen, and phenyl, 1-naphthyl, 2-naphthyl, anthracenyl and phenanthrenyl, which may optionally be substituted with one or more Xa, Xa is linear or branched $C_{1-6}$ alkyl, $C_{1-6}$ alkenyl, $C_{1-6}$ alkynyl, $C_{1-6}$ alkoxy, halo, hydroxy, nitro, carboxy, cyano, sulfo, amino or alkylamino, which may optionally be substituted with one or more substituents selected from the group consisting of halo, amino, cyano, carboxy, carbonyl, hydroxy, alkoxy, alkylamino, nitroso, nitro and sulfo, and Y is selected from the group consisting of halo, amino, cyano, carboxy, carbonyl, alkoxy and sulfo, or having a structure of formula Ib or IIb:

[Formula 8]

(Ib)

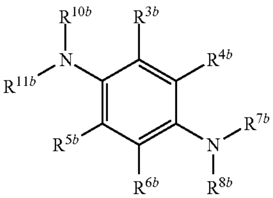

or (IIb)

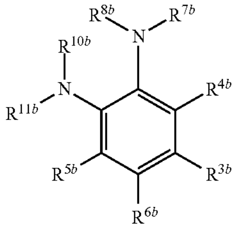

wherein $R^{7b}$, $R^{8b}$ and $R^{10b}$ are each independently hydrogen, or linear or branched $C_{1-6}$ alkyl, $C_{1-6}$ alkenyl, $C_{1-6}$ alkynyl, $C_{3-9}$ cycloalkyl, phenyl, 1-naphthyl, 2-naphthyl, anthracenyl or phenanthrenyl, which may optionally be substituted with one or more Xb, $R^{3b}$, $R^{4b}$, $R^{5b}$ and $R^{6b}$ are each independently hydrogen, or linear or branched $C_{1-6}$ alkyl, $C_{1-6}$ alkenyl, $C_{1-6}$ alkynyl, $C_{1-6}$ alkoxy, halo, nitro, cyano, carboxy, sulfo or amino, which may optionally be substituted with one or more Y, $R^{11b}$ is selected from the group consisting of phenyl, 1-naphthyl, 2-naphthyl, anthracenyl and phenanthrenyl, which may optionally be substituted with one or more Xb, wherein Xb is linear or branched $C_{1-6}$ alkyl, $C_{1-6}$ alkenyl, $C_{1-6}$ alkynyl, $C_{1-6}$ alkoxy, halo, hydroxy, nitro, carboxy, cyano, sulfo or amino, which may optionally be substituted with one or more substituents selected from the group consisting of halo, amino, cyano, carboxy, carbonyl, alkoxy and sulfo, and Y is selected from the group consisting of halo, amino, cyano, carboxy, carbonyl, alkoxy and sulfo, or a salt, an anhydride or a solvate thereof, wherein the compound is neither N-methyl-N-phenyl-1,4-phenylenediamine, nor N-methyl-N-(3-methoxyphenyl)-1,4-phenylenediamine, and wherein the compound is neither

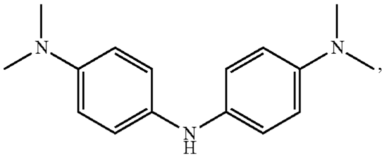

,

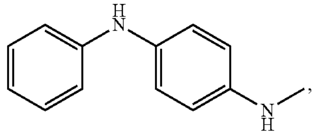

, nor

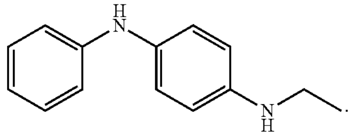

.

5. The composition according to claim 4, wherein the enzyme is an oxidoreductase.

6. An electrode comprising the electrode modifying agent or the electron transfer promoting agent according to claim 1.

7. The electrode according to claim 6, comprising the enzyme.

8. The electrode according to claim 7, wherein the enzyme is an oxidoreductase.

9. The electrode according to claim 8, wherein the oxidoreductase is fixed.

10. A sensor comprising the electrode modifying agent or the electron transfer promoting agent according to claim 1.

11. An electrochemical measurement method using the electrode according to claim 6.

12. A method for modifying or altering an electrode, comprising the step of contacting the electrode modifying agent or the electron transfer promoting agent according to claim 1 with the electrode.

13. A method for producing a battery, comprising the step of using the electrode modifying agent or the electron transfer promoting agent according to claim 1.

14. The method according to claim 13, comprising the step of contacting the electrode modifying agent or the electron transfer promoting agent with an electrode of the battery.

15. A power generation method using the battery according to claim 13.

* * * * *